(12) United States Patent
Kurata et al.

(10) Patent No.: US 10,343,438 B2
(45) Date of Patent: Jul. 9, 2019

(54) HEAT-SENSITIVE RECORDING MATERIAL

(71) Applicant: Nippon Kayaku Kabushiki Kaisha, Tokyo (JP)

(72) Inventors: Takaaki Kurata, Tokyo (JP); Kyohei Miyanaga, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 26 days.

(21) Appl. No.: 15/515,622

(22) PCT Filed: Sep. 30, 2015

(86) PCT No.: PCT/JP2015/077680
§ 371 (c)(1),
(2) Date: Mar. 30, 2017

(87) PCT Pub. No.: WO2016/052592
PCT Pub. Date: Apr. 7, 2016

(65) Prior Publication Data
US 2017/0297355 A1    Oct. 19, 2017

(30) Foreign Application Priority Data

Sep. 30, 2014 (JP) ................. 2014-200700
Oct. 17, 2014 (JP) ................. 2014-212562
Nov. 28, 2014 (JP) ................. 2014-240944
Dec. 17, 2014 (JP) ................. 2014-254793

(51) Int. Cl.
| | | |
|---|---|---|
| B41M 5/333 | (2006.01) | |
| C07D 235/30 | (2006.01) | |
| C07D 277/42 | (2006.01) | |
| C07C 275/40 | (2006.01) | |
| C07C 311/05 | (2006.01) | |
| C07C 321/30 | (2006.01) | |
| B41M 5/327 | (2006.01) | |

(52) U.S. Cl.
CPC ........ B41M 5/3333 (2013.01); B41M 5/3335 (2013.01); C07C 275/40 (2013.01); C07C 311/05 (2013.01); C07C 321/30 (2013.01); C07D 235/30 (2013.01); C07D 277/42 (2013.01); B41M 5/3275 (2013.01); B41M 5/3336 (2013.01); B41M 2205/04 (2013.01); C07C 2601/14 (2017.05)

(58) Field of Classification Search
None
See application file for complete search history.

(56) References Cited

U.S. PATENT DOCUMENTS 3,539,375 A    11/1970   Baum
3,897,493 A    7/1975    Teach

FOREIGN PATENT DOCUMENTS

JP        57-11088 A     1/1982
JP        9-193553 A     7/1997

OTHER PUBLICATIONS

STN Registry Database entry for CAS RN 1638678-88-2, Entered STN Dec. 15, 2014, Accessed Jan. 3, 2019.*
STN Registry Database entry for CAS RN 1638678-89-3, Entered STN Dec. 15, 2014, Accessed Jan. 3, 2019.*
STN Registry Database entry for CAS RN 1031495-58-5, Entered STN Jun. 29, 2008, Accessed Jan. 3, 2019.*
Gante et al., "Peptide Synthesis, A New Carboxamide Synthesis," Chemiker-Zeitung, 1985, 109(4), pp. 155-156.
International Search Report and Written Opinion dated Nov. 2, 2015 in corresponding PCT application No. PCT/JP2015/077680.
International Preliminary Report on Patentability dated Apr. 13, 2017 in corresponding PCT application No. PCT/JP2015/077680.

* cited by examiner

*Primary Examiner* — Alicia L Otton
(74) *Attorney, Agent, or Firm* — Nields, Lemack & Frame, LLC

(57) ABSTRACT

This heat-sensitive recording material is configured to contain, as a color-developing compound, at least one compound represented by one of formulas (1)-(3):

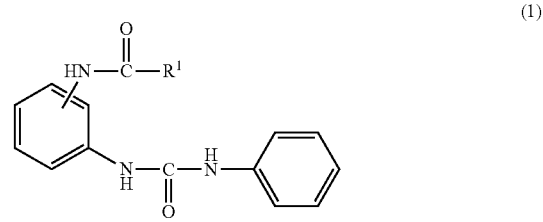

(1)

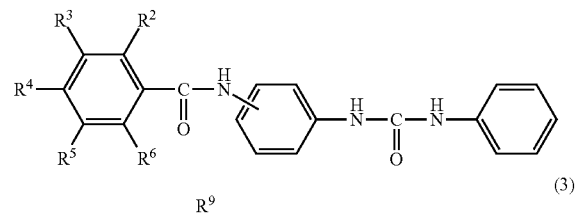

(2)

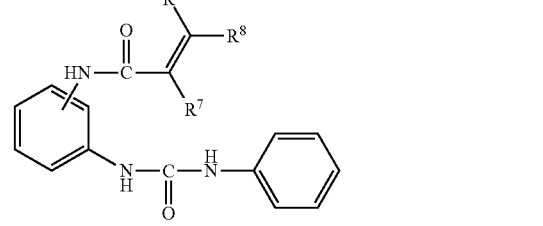

(3)

19 Claims, No Drawings

HEAT-SENSITIVE RECORDING MATERIAL

TECHNICAL FIELD

The present invention relates to a thermosensitive recording material that is excellent in water resistance or alcohol resistance and has a background excellent in heat resistance.

BACKGROUND ART

Thermosensitive recording materials are generally prepared by making dispersed fine particles of a leuco dye and fine particles of a color developer such as a phenolic compound respectively, then mixing these fine particles, adding thereto additives such as a binder, a sensitizer, a filler and a lubricant to obtain a liquid coating material, and applying the obtained coating material to paper, films, synthetic papers or the like. The recording materials produce color developments through chemical reactions that occur by melting one or both of the leuco dye and the color developer by heating to bring into contact with each other. To induce the color formation of such thermosensitive recording materials, for example, a thermal printer equipped with a thermal head is used. This thermosensitive recording method, as compared with other recording methods, is widely used in, for example, the fields of facsimiles, printers (computer output, calculators, etc.), recorders for medical measurements, automatic ticket machines and thermosensitive recording labels, because of its characteristics of: (1) no noise in recording; (2) no requirement to develop or fix an image; (3) maintenance-free; (4) a machine being relatively inexpensive; etc.

In recent years, in order to further expand applications of thermosensitive recording materials and to further increase efficiency, there have been increasing needs for high speed recording. Thus, it has been strongly desired to develop a thermosensitive recording material capable of sufficiently satisfying needs for high speed recording. In this case, a color developer needs to have a low melting point and less heat of fusion. Such properties, however, tend to cause deterioration of unrecorded parts (background fogging) of thermosensitive recording materials during production, use or storage. As a result, not only high whiteness but improvement in stability is strongly desired.

In general, a color developer having a phenolic hydroxy group has high ability to develop color. Among them, a large number of bisphenolic color developers including, for example, 2,2-bis(4-hydroxyphenylpropane) (bisphenol A) described in Patent Literature 1 and 4,4'-dihydroxydiphenylsulfone (bisphenol S) described in Patent Literature 2 have been reported because of their high coloring density. However, these color developers have disadvantages of less water and alcohol resistance, deterioration of background (background fogging) and the like.

CITATION LIST

Patent Literature

Patent Literature 1: U.S. Pat. No. 3,539,375
Patent Literature 2: JP 57-11088 A

SUMMARY OF INVENTION

Technical Problem

An object of the present invention is to solve the disadvantages with the above-mentioned state of the art. Specifically, an object of the present invention is to provide a thermosenstive recording material that is excellent in water resistance or alcohol resistance of a recorded part and has a background exhibiting high stability against heat.

Solution to Problem

The present inventor has conducted diligent studies to attain the object and newly found that a thermosenstive recording material comprising a compound having a certain structure as a color developer is excellent in water resistance or alcohol resistance and provides a background excellent in heat resistance, thereby completing the present invention.

Specifically, the present invention relates to:

[1] a thermosenstive recording material comprising at least one of compound represented by any of the following formulas (1) to (3):

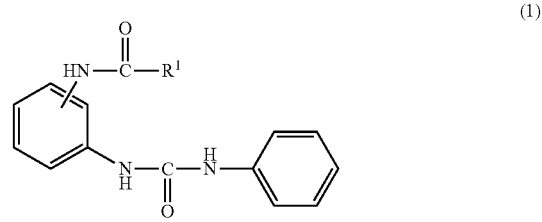

wherein $R^1$ represents an alkyl group optionally having a substituent;

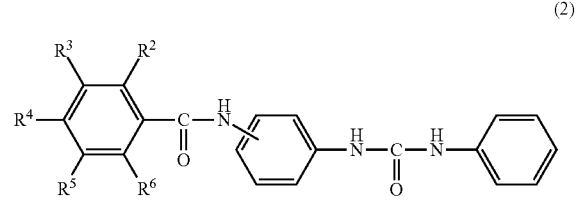

wherein $R^2$ to $R^6$ each independently represent a hydrogen atom, an alkyl group, an arylalkyl group, an aryl group, a 5- or 6-membered heterocyclic group containing 1 to 3 atoms selected from a nitrogen atom, an oxygen atom and a sulfur atom as ring-constituting atoms, a 5- or 6-membered heterocyclylamino group containing 1 to 3 atoms selected from a nitrogen atom, an oxygen atom and a sulfur atom as ring-constituting atoms, a ring-fused heterocyclylamino group in which one benzene ring is fused with a 5- or 6-membered heterocyclic group containing 1 to 3 atoms selected from a nitrogen atom, an oxygen atom and a sulfur atom as ring-constituting atoms, an alkoxy group, an aryloxy group, an alkylcarbonylamino group, an arylcarbonylamino group, an alkylcarbonyloxy group, an arylcarbonyloxy group, an alkylcarbonyl group, an arylcarbonyl group, a carbamoyl group, a monoalkylcarbamoyl group, a dialkylcarbamoyl group, a monoarylcarbamoyl group, a diarylcarbamoyl group, an alkoxycarbonyl group, an aryloxycarbonyl group, an alkylsulfonylamino group, an arylsulfonylamino group, a sulfamoyl group, a monoalkylsulfamoyl group, a dialkylsulfamoyl group, a monoarylsulfamoyl group, a diarylsulfamoyl group, a hydroxy group, an alkylsulfonyl group, an arylsulfonyl group, an alkylthio group, an arylthio group, an ureido group, a dialkylureido group, a monoarylureido group, a diarylureido group, an alkoxycarbonylamino group, a cyano group, a nitro group, an amino group, a monoalkylamino group, a dialkylamino group, an arylamino group which may be a monoarylamino group or a diarylamino group, a mercapto group, a carboxy group, a sulfone group or a halogen atom; and (3)

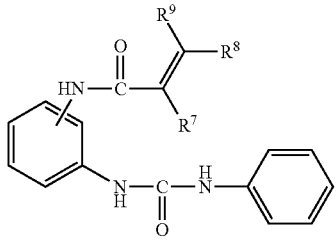

wherein $R^7$, $R^8$ and $R^9$ each represent a hydrogen atom, or an alkyl group or an aryl group optionally having a substituent;

[2] the thermosenstive recording material according to [1], wherein in the formula (1), $R^1$ is an unsubstituted alkyl group or an alkyl group substituted with an aryl group;

[3] the thermosenstive recording material according to [1] or [2], wherein in the formula (1), $R^1$ is an unsubstituted alkyl group;

[4] the thermosenstive recording material according to any one of [1] to [3], wherein in the formula (1), $R^1$ is a methyl group or an ethyl group;

[5] the thermosenstive recording material according to [1], wherein the compound of the formula (1) is a compound represented by any of the following formulas (4) to (7):

(4)

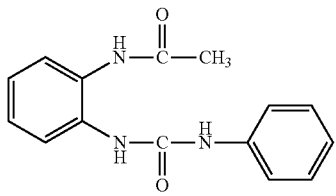

(5)

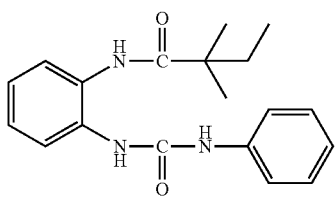

(6)

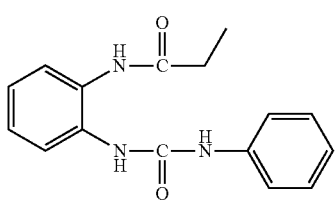

(7)

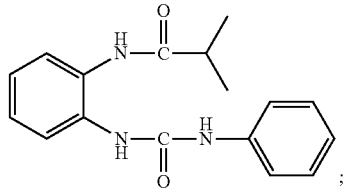

;

[6] the thermosenstive recording material according to [1], wherein in the formula (2), $R^2$ to $R^6$ are each independently a group selected from the group consisting of a hydrogen atom, an alkyl group, an arylalkyl group, a 5- or 6-membered heterocyclylamino group containing 1 to 3 atoms selected from a nitrogen atom, an oxygen atom and a sulfur atom as ring-constituting atoms, a ring-fused heterocyclylamino group in which one benzene ring is fused with a 5- or 6-membered heterocyclic group containing 1 to 3 atoms selected from a nitrogen atom, an oxygen atom and a sulfur atom as ring-constituting atoms, an alkoxy group, an aryloxy group, an alkylcarbonylamino group, a carbamoyl group, a hydroxy group, a carboxy group, an alkylsulfonyl group, an arylthio group, a cyano group, an amino group, an arylamino group, a halogen atom and a nitro group;

[7] the thermosenstive recording material according to [1] or [6], wherein in the formula (2), $R^2$ to $R^6$ are each independently a hydrogen atom or an alkyl group;

[8] the thermosenstive recording material according to [1] or [6], wherein in the formula (2), $R^2$ is a methyl group, and each of $R^3$ to $R^6$ is a hydrogen atom, or each of $R^2$, $R^3$, $R^5$ and $R^6$ is a hydrogen atom, and $R^4$ is a methyl group;

[9] the thermosenstive recording material according to [1] or [6], wherein the formula (2) is represented by any of the following formulas (8) to (11):

(8)

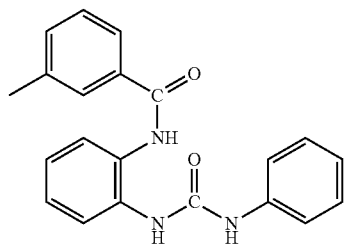

(9)

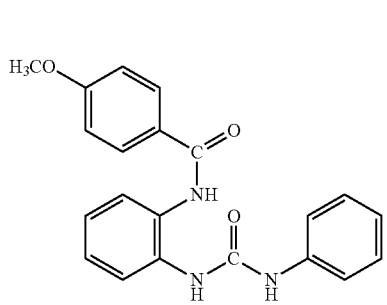

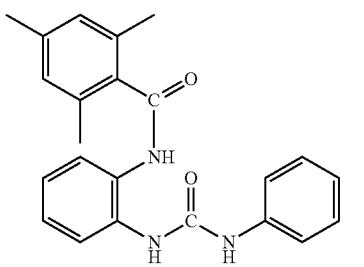

(10)

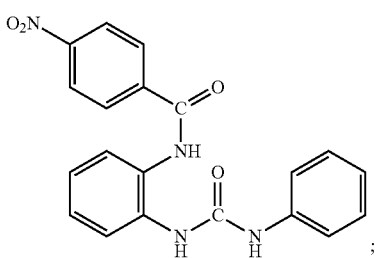

(11)

[10] the thermosenstive recording material according to [1], wherein in the formula (3), each of R⁷, R⁸ and R⁹ is a hydrogen atom, a methyl group or a phenyl group;

[11] the thermosenstive recording material according to [1] or [10], wherein in the formula (3), all of $R^7$, $R^8$ and $R^9$ are hydrogen atoms; or $R^7$ is a methyl group, and each of $R^8$ and $R^9$ is a hydrogen atom; or $R^8$ is a methyl group or a phenyl group, and each of $R^7$ and $R^9$ is a hydrogen atom;

[12] a compound represented by the following formula (3):

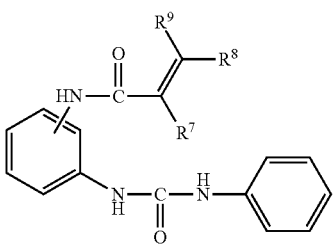

(3)

wherein $R^7$, $R^8$ and $R^9$ each represent a hydrogen atom, or an alkyl group or an aryl group optionally having a substituent;

[13] the compound according to [12], wherein the compound is represented by any of the following formulas (12) to (14):

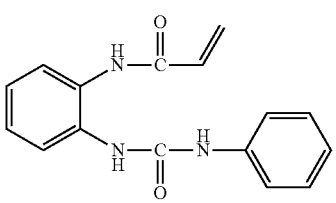

(12)

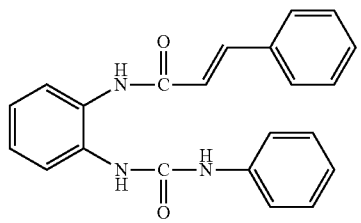

(13)

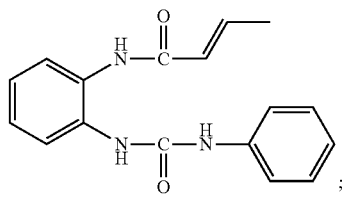

(14)

[14] a compound represented by any of the following formulas (4) to (7):

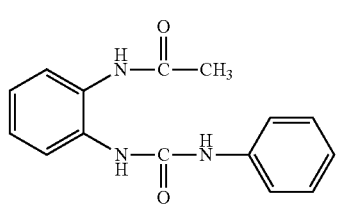 [SMILES: CC(=O)Nc1ccccc1NC(=O)Nc1ccccc1]

(4)

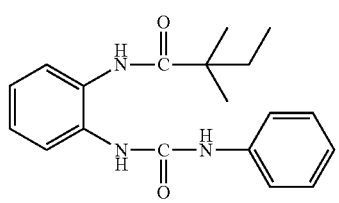

(5)

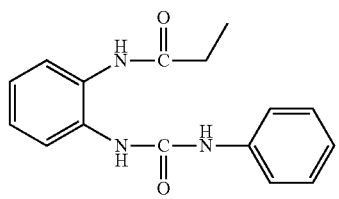

(6)

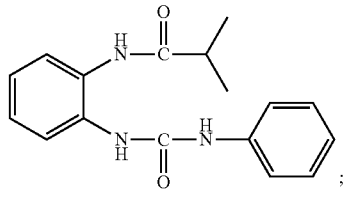

(7)

[15] a compound represented by any of the following formulas (8) to (11):

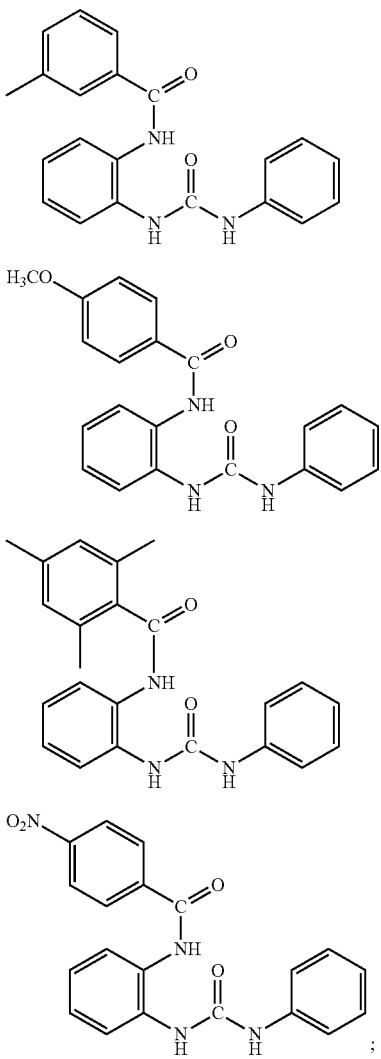

[16] a thermosenstive recording layer comprising a thermosenstive recording material according to any one of [1] to [11]; and

[17] a thermosenstive recording paper comprising a thermosenstive recording layer according to [16].

Advantageous Effects of Invention

The present invention can provide a thermosenstive recording material that has favorable water resistance or alcohol resistance and has a background exhibiting high stability against heat, because of comprising a compound represented by any of the formulas (1) to (3) as a color developer.

DESCRIPTION OF EMBODIMENTS

The present invention will be described in detail.

The present invention relates to, as mentioned above, a thermosenstive recording material comprising a compound represented by any of the formulas (1) to (3). The thermosenstive recording material according to the present invention usually contains an achromic or hypochromic color-forming compound and may optionally contain an additional color developing compound. Also, the thermosenstive recording material according to the present invention may optionally contain a sensitizer and/or a preservation stabilizer and may further contain a binder, a filler and/or other additives.

Examples of the alkyl group represented by $R^1$ in the formula (1) include a linear, branched or cyclic alkyl group. Among them, a linear or branched alkyl group is preferred, and a linear alkyl group is more preferred. The number of carbon atoms thereof is usually C1 to C12, preferably C1 to C8, more preferably C1 to C6, further preferably C1 to C4. Specific examples of the alkyl group include: a linear alkyl group such as methyl, ethyl, n-propyl, n-butyl, n-pentyl, n-hexyl, n-octyl, n-nonyl, n-decyl, n-undecyl and n-dodecyl; a branched alkyl group such as isopropyl, isobutyl, sec-butyl, t-butyl, isopentyl, isohexyl and isooctyl; and a cyclic alkyl group such as cyclopropyl, cyclobutyl, cyclopentyl and cyclohexyl. Methyl and ethyl are particularly preferred.

Examples of the substituent that the alkyl group represented by $R^1$ may have, include, but are not limited to, an aryl group, a 5- or 6-membered heterocyclic group containing 1 to 3 atoms selected from a nitrogen atom, an oxygen atom and a sulfur atom as ring-constituting atoms, a 5- or 6-membered heterocyclylamino group containing 1 to 3 atoms selected from a nitrogen atom, an oxygen atom and a sulfur atom as ring-constituting atoms, a ring-fused heterocyclylamino group in which one benzene ring is fused with a 5- or 6-membered heterocyclic ring containing 1 to 3 atoms selected from a nitrogen atom, an oxygen atom and a sulfur atom as ring-constituting atoms, a linear, branched or cyclic alkoxy group, an aryloxy group, a linear, branched or cyclic alkylcarbonylamino group, an arylcarbonylamino group, a linear, branched or cyclic alkylcarbonyloxy group, an arylcarbonyloxy group, a linear, branched or cyclic alkylcarbonyl group, an arylcarbonyl group, a carbamoyl group, a linear, branched or cyclic monoalkylcarbamoyl group, a linear, branched or cyclic dialkylcarbamoyl group, a monoarylcarbamoyl group, a diarylcarbamoyl group, a linear, branched or cyclic alkoxycarbonyl group, an aryloxycarbonyl group, a linear, branched or cyclic alkylsulfonylamino group, an arylsulfonylamino group, a sulfamoyl group, a linear, branched or cyclic monoalkylsulfamoyl group, a linear, branched or cyclic dialkylsulfamoyl group, a monoarylsulfamoyl group, a diarylsulfamoyl group, a linear, branched or cyclic alkylsulfonyl group, an arylsulfonyl group, a linear, branched or cyclic alkylthio group, an arylthio group, an ureido group, a linear, branched or cyclic monoalkylureido group, a linear, branched or cyclic dialkylureido group, a monoarylureido group, a diarylureido group, a linear, branched or cyclic alkoxycarbonylamino group, an aryloxycarbonylamino group, a linear, branched or cyclic monoalkylamino group, a linear, branched or cyclic dialkylamino group, an arylamino group, a mercapto group which means a group represented by "—SH" as used herein, a halogen atom, a hydroxy group, a cyano group, a nitro group, an amino group and a carboxy group.

Examples of the aryl group preferably include a C6-C12 aryl group. Specific examples thereof include phenyl, naphthyl and biphenyl.

Examples of the 5- or 6-membered heterocyclic group containing 1 to 3 atoms selected from a nitrogen atom, an oxygen atom and a sulfur atom as ring-constituting atoms preferably include an aromatic heterocyclic group. Specific examples thereof include: a 5-membered alicyclic heterocyclic ring such as pyrrolidinyl, tetrahydrofuryl, tetrahydrothiophen-2-yl and tetrahydrothiophen-3-yl; a 6-membered alicyclic heterocyclic group such as piperidinyl, piperazinyl, dioxan-2-yl, morpholinyl and thiomorpholinyl; a 5-membered aromatic heterocyclic group such as pyrrole, pyrazole, imidazole, triazole, furyl, thiophen-2-yl, thiophen-3-yl, oxazole and thiazole; and a 6-membered aromatic heterocyclic group such as pyridine, pyrazine, pyridazine and triazine. The ring-constituting atom is preferably selected from a nitrogen atom and a sulfur atom.

The 5- or 6-membered heterocyclylamino group containing 1 to 3 atoms selected from a nitrogen atom, an oxygen atom and a sulfur atom as ring-constituting atoms preferably has an aromatic ring as its heterocyclic moiety. Specific examples thereof include: a 5-membered alicyclic heterocyclylamino group such as pyrrolidinylamino, tetrahydrofurylamino, tetrahydrothiophen-2-yl amino and tetrahydrothiophen-3-yl amino; a 6-membered alicyclic heterocyclylamino group such as piperidinylamino, piperazinylamino, dioxan-2-yl amino, morpholinylamino and thiomorpholinylamino; a 5-membered aromatic heterocyclylamino group such as pyrrolamino, pyrazolamino, imidazolamino, triazolamino, furylamino, thiophen-2-yl amino, thiophen-3-yl amino, oxazolamino and thiazolamino; and a 6-membered aromatic heterocyclylamino group such as pyridylamino, pyrazylamino, pyridazinylamino and triazinylamino. The ring-constituting atom is preferably selected from a nitrogen atom and a sulfur atom.

The ring-fused heterocyclylamino group in which one benzene ring is fused with a 5- or 6-membered heterocyclic ring containing 1 to 3 atoms selected from a nitrogen atom, an oxygen atom and a sulfur atom as ring-constituting atoms preferably has an aromatic ring as its heterocyclic moiety. Specific examples thereof include: a heterocyclylamino group having a 5-membered alicyclic heterocyclic ring as its heterocyclic moiety, such as phthalanylamino; a heterocyclylamino group having a 6-membered alicyclic heterocyclic ring as its heterocyclic moiety, such as benzopyranylamino; a heterocyclylamino group having a 5-membered aromatic heterocyclic ring as its heterocyclic moiety, such as benzopyrrolamino, benzopyrazolamino, benzimidazolamino, benzotriazolamino, benzofuranylamino, benzothiophen-2-yl amino, benzothiophen-3-yl amino, benzoxazolamino and benzothiazolamino; and a heterocyclylamino group having a 6-membered aromatic heterocyclic ring as its heterocyclic moiety, such as quinolinylamino, cinnolinylamino, phthalazinylamino, quinazolinylamino and quinoxalinylamino. The ring-constituting atom is preferably selected from a nitrogen atom and a sulfur atom.

Examples of the linear, branched or cyclic alkoxy group preferably include a C1-C10 alkoxy group. Specific examples thereof include: a linear alkoxy group such as methoxy, ethoxy, n-propoxy, n-butoxy, n-pentoxy, n-hexyloxy, n-heptoxy, n-octyloxy, n-nonyloxy and n-decyloxy; a branched alkoxy group such as isopropoxy, isobutoxy, sec-butoxy, t-butoxy, isoamyloxy, t-amyloxy, isohexyloxy, t-hexyloxy, isoheptoxy, t-heptoxy, isooctyloxy, t-octyloxy, 2-ethylhexyloxy, isononyloxy and isodecyloxy, preferably a C3-C10 branched alkoxy group; and a cyclic alkoxy group such as cyclopropoxy, cyclobutoxy, cyclopentoxy, cyclohexyloxy and cycloheptoxy, preferably a C3-C7 cyclic alkoxy group. Preferred examples thereof include a linear or branched alkoxy group.

Examples of the aryloxy group preferably include a C6-C12 aryloxy group. Specific examples thereof include phenoxy, naphthyloxy and biphenyloxy.

Examples of the linear, branched or cyclic alkylcarbonylamino group preferably include a C1-C10 alkylcarbonylamino group. Specific examples thereof include: a linear alkylcarbonylamino group such as methylcarbonylamino, ethylcarbonylamino, n-propylcarbonylamino, n-butylcarbonylamino, n-pentylcarbonylamino, n-hexylcarbonylamino, n-heptylcarbonylamino, n-octylcarbonylamino, n-nonylcarbonylamino and n-decylcarbonylamino; a branched alkylcarbonylamino group such as isopropylcarbonylamino, isobutylcarbonylamino, sec-butylcarbonylamino, t-butylcarbonylamino, isoamylcarbonylamino, t-amylcarbonylamino, isohexylcarbonylamino, t-hexylcarbonylamino, isoheptylcarbonylamino, t-heptylcarbonylamino, isooctylcarbonylamino, t-octylcarbonylamino, 2-ethylhexylcarbonylamino, isononylcarbonylamino and isodecylcarbonylamino, preferably a C3-C10 branched alkylcarbonylamino group; and a cyclic alkylcarbonylamino group such as cyclopropylcarbonylamino, cyclobutylcarbonylamino, cyclopentylcarbonylamino, cyclohexylcarbonylamino and cycloheptylcarbonylamino, preferably a C3-C7 cyclic alkylcarbonylamino group. Preferred examples thereof include a linear or branched alkylcarbonylamino group, more preferably a linear alkylcarbonylamino group.

Examples of the arylcarbonylamino group preferably include a C6-C12 arylcarbonylamino group. Specific examples thereof include phenylcarbonylamino, naphthylcarbonylamino and biphenylcarbonylamino.

Examples of the linear, branched or cyclic alkylcarbonyloxy group preferably include a C1-C10 alkylcarbonyloxy group. Specific examples thereof include: a linear alkylcarbonyloxy group such as methylcarbonyloxy, ethylcarbonyloxy, n-propylcarbonyloxy, n-butylcarbonyloxy, n-pentylcarbonyloxy, n-hexylcarbonyloxy, n-heptylcarbonyloxy, n-octylcarbonyloxy, n-nonylcarbonyloxy and n-decylcarbonyloxy; a branched alkylcarbonyloxy group such as isopropylcarbonyloxy, isobutylcarbonyloxy, sec-butylcarbonyloxy, t-butylcarbonyloxy, isoamylcarbonyloxy, t-amylcarbonyloxy, isohexylcarbonyloxy, t-hexylcarbonyloxy, isoheptylcarbonyloxy, t-heptylcarbonyloxy, isooctylcarbonyloxy, t-octylcarbonyloxy, 2-ethylhexylcarbonyloxy, isononylcarbonyloxy and isodecylcarbonyloxy, preferably a C3-C10 branched alkylcarbonyloxy group; and a cyclic alkylcarbonyloxy group such as cyclopropylcarbonyloxy, cyclobutylcarbonyloxy, cyclopentylcarbonyloxy, cyclohexylcarbonyloxy and cycloheptylcarbonyloxy, preferably a C3-C7 cyclic alkylcarbonyloxy group. Among them, a linear or branched alkylcarbonyloxy group is preferred, and a linear alkylcarbonyloxy group is more preferred.

Examples of the arylcarbonyloxy group preferably include a C6-C12 arylcarbonyloxy group. Specific examples thereof include phenylcarbonyloxy, naphthylcarbonyloxy and biphenylcarbonyloxy.

Examples of the linear, branched or cyclic alkylcarbonyl group preferably include a C1-C10 alkylcarbonyl group. Specific examples thereof include: a linear alkylcarbonyl group such as methylcarbonyl, ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl and n-decylcarbonyl; a branched alkylcarbonyl group such as isopropylcarbonyl, isobutylcarbonyl, sec-butylcarbonyl, t-butylcarbonyl, isoamylcarbonyl, t-amylcarbonyl, isohexylcarbonyl, t-hexylcarbonyl, isoheptylcarbonyl, t-heptylcarbonyl, isooctylcarbonyl, t-octylcarbonyl, 2-ethylhexylcarbonyl, isononylcarbonyl and isodecylcarbonyl, preferably a C3-C10 branched alkylcarbonyl group; and a cyclic alkylcarbonyl group such as cyclopropylcarbonyl, cyclobutylcarbonyl, cyclopentylcarbonyl, cyclohexylcarbonyl and cycloheptylcarbonyl, preferably a C3-C7 cyclic alkylcarbonyl group. Among them, a linear or branched alkylcarbonyl group is preferred, and a linear alkylcarbonyl group is more preferred.

Examples of the arylcarbonyl group preferably include a C6-C12 arylcarbonyl group. Specific examples thereof include phenylcarbonyl (benzoyl), naphthylcarbonyl and biphenylcarbonyl.

Examples of the linear, branched or cyclic monoalkylcarbamoyl group preferably include a mono-C1-C10 alkylcarbamoyl group. Specific examples thereof include: a linear monoalkylcarbamoyl group such as methylcarbamoyl, ethylcarbamoyl, n-propylcarbamoyl, n-butylcarbamoyl, n-pentylcarbamoyl, n-hexylcarbamoyl, n-heptylcarbamoyl, n-octylcarbamoyl, n-nonylcarbamoyl and n-decylcarbamoyl; a branched monoalkylcarbamoyl group such as isopropylcarbamoyl, isobutylcarbamoyl, sec-butylcarbamoyl, t-butylcarbamoyl, isoamylcarbamoyl, t-amylcarbamoyl, isohexylcarbamoyl, t-hexylcarbamoyl, isoheptylcarbamoyl, t-heptylcarbamoyl, isooctylcarbamoyl, t-octylcarbamoyl, 2-ethylhexylcarbamoyl, isononylcarbamoyl and isodecylcarbamoyl, preferably a C3-C10 branched monoalkylcarbamoyl group; and a cyclic monoalkylcarbamoyl group such as cyclopropylcarbamoyl, cyclobutylcarbamoyl, cyclopentylcarbamoyl, cyclohexylcarbamoyl and cycloheptylcarbamoyl, preferably a C3-C7 cyclic monoalkylcarbamoyl group. Preferred examples thereof include a linear or branched monoalkylcarbamoyl group, more preferably a linear monoalkylcarbamoyl group.

Examples of the linear, branched or cyclic dialkylcarbamoyl group preferably include a di-C1-C10 alkylcarbamoyl group. Specific examples thereof include: a linear dialkylcarbamoyl group such as dimethylcarbamoyl, diethylcarbamoyl, di-n-propylcarbamoyl, di-n-butylcarbamoyl, di-n-pentylcarbamoyl, di-n-hexylcarbamoyl, di-n-heptylcarbamoyl, di-n-octylcarbamoyl, di-n-nonylcarbamoyl and di-n-decylcarbamoyl; a branched dialkylcarbamoyl group such as diisopropylcarbamoyl, diisobutylcarbamoyl, di-sec-butylcarbamoyl, di-t-butylcarbamoyl, diisoamylcarbamoyl, di-t-amylcarbamoyl, diisohexylcarbamoyl, di-t-hexylcarbamoyl, diisoheptylcarbamoyl, di-t-heptylcarbamoyl, diisooctylcarbamoyl, di-t-octylcarbamoyl, di-(2-ethylhexyl)carbamoyl, diisononylcarbamoyl and diisodecylcarbamoyl, preferably a carbamoyl group having two C3-C10 branched groups; and a cyclic dialkylcarbamoyl group such as dicyclopropylcarbamoyl, dicyclobutylcarbamoyl, dicyclopentylcarbamoyl, dicyclohexylcarbamoyl and dicycloheptylcarbamoyl, preferably a carbamoyl group having two C3-C7 cyclic alkyl groups. Preferred examples thereof include a linear or branched dialkylcarbamoyl group, more preferably a linear dialkylcarbamoyl group.

Examples of the monoarylcarbamoyl group preferably include a mono-C6-C12 arylcarbamoyl group. Specific examples thereof include phenylcarbamoyl, naphthylcarbamoyl and biphenylcarbamoyl.

Examples of the diarylcarbamoyl group preferably include a di-C6-C12 arylcarbamoyl group. Specific examples thereof include diphenylcarbamoyl, dinaphthylcarbamoyl and di(biphenyl)carbamoyl.

Examples of the linear, branched or cyclic alkoxycarbonyl group preferably include a C1-C10 alkoxycarbonyl group. Specific examples thereof include: a linear alkoxycarbonyl group such as methoxycarbonyl, ethoxycarbonyl, n-propoxycarbonyl, n-butoxycarbonyl, n-pentoxycarbonyl, n-hexyloxycarbonyl, n-heptoxycarbonyl, n-octyloxycarbonyl, n-nonyloxycarbonyl and n-decyloxycarbonyl; a branched alkoxycarbonyl group such as isopropoxycarbonyl, isobutoxycarbonyl, sec-butoxycarbonyl, t-butoxycarbonyl, isoamyloxycarbonyl, t-amyloxycarbonyl, isohexyloxycarbonyl, t-hexyloxycarbonyl, isoheptoxycarbonyl, t-heptoxycarbonyl, isooctyloxycarbonyl, t-octyloxycarbonyl, 2-ethylhexyloxycarbonyl, isononyloxycarbonyl and isodecyloxycarbonyl, preferably a C3-C10 branched alkoxycarbonyl group; and a cyclic alkoxycarbonyl group such as cyclopropoxycarbonyl, cyclobutoxycarbonyl, cyclopentoxycarbonyl, cyclohexyloxycarbonyl and cycloheptoxycarbonyl, preferably a C3-C7 cyclic alkoxycarbonyl group. Preferred examples thereof include a linear or branched alkoxycarbonyl group, more preferably a linear alkoxycarbonyl group.

Examples of the aryloxycarbonyl group preferably include a C6-C12 aryloxycarbonyl group. Specific examples thereof include phenoxycarbonyl, naphthyloxycarbonyl and biphenyloxycarbonyl.

Examples of the linear, branched or cyclic alkylsulfonylamino group preferably include a C1-C10 alkylsulfonylamino group. Specific examples thereof include: a linear alkylsulfonylamino group such as methylsulfonylamino, ethylsulfonylamino, n-propylsulfonylamino, n-butylsulfonylamino, n-pentylsulfonylamino, n-hexylsulfonylamino, n-heptylsulfonylamino, n-octylsulfonylamino, n-nonylsulfonylamino and n-decylsulfonylamino; a branched alkylsulfonylamino group such as isopropylsulfonylamino, isobutylsulfonylamino, sec-butylsulfonylamino, t-butylsulfonylamino, isoamylsulfonylamino, t-amylsulfonylamino, isohexylsulfonylamino, t-hexylsulfonylamino, isoheptylsulfonylamino, t-heptylsulfonylamino, isooctylsulfonylamino, t-octylsulfonylamino, 2-ethylhexylsulfonylamino, isononylsulfonylamino and isodecylsulfonylamino, preferably a C3-C10 branched alkylsulfonylamino group; and a cyclic alkylsulfonylamino group such as cyclopropylsulfonylamino, cyclobutylsulfonylamino, cyclopentylsulfonylamino, cyclohexylsulfonylamino and cycloheptylsulfonylamino, preferably a C3-C7 cyclic alkylsulfonylamino group. Preferred examples thereof include a linear or branched alkylsulfonylamino group, more preferably a linear alkylsulfonylamino group.

Examples of the arylsulfonylamino group preferably include a C6-C12 arylsulfonylamino group. Specific examples thereof include phenylsulfonylamino, toluenesulfonylamino, naphthylsulfonylamino and biphenylsulfonylamino.

Examples of the linear, branched or cyclic monoalkylsulfamoyl group preferably include a mono-C1-C10 alkylsulfamoyl group. Specific examples thereof include: a linear monoalkylsulfamoyl group such as methylsulfamoyl, ethylsulfamoyl, n-propylsulfamoyl, n-butylsulfamoyl, n-pentylsulfamoyl, n-hexylsulfamoyl, n-heptylsulfamoyl, n-octylsulfamoyl, n-nonylsulfamoyl and n-decylsulfamoyl; a branched monoalkylsulfamoyl group such as isopropylsulfamoyl, isobutylsulfamoyl, sec-butylsulfamoyl, t-butylsulfamoyl, isoamylsulfamoyl, t-amylsulfamoyl, isohexylsulfamoyl, t-hexylsulfamoyl, isoheptylsulfamoyl, t-heptylsulfamoyl, isooctylsulfamoyl, t-octylsulfamoyl, 2-ethylhexylsulfamoyl, isononylsulfamoyl and isodecylsulfamoyl, preferably a C3-C10 branched monoalkylsulfamoyl group; and a cyclic monoalkylsulfamoyl group such as cyclopropylsulfamoyl, cyclobutylsulfamoyl, cyclopentylsulfamoyl, cyclohexylsulfamoyl and cycloheptylsulfamoyl, preferably a C3-C7 cyclic monoalkylsulfamoyl group. Preferred examples thereof include a linear or branched monoalkylsulfamoyl group, more preferably a linear monoalkylsulfamoyl group.

Examples of the linear, branched or cyclic dialkylsulfamoyl group preferably include a di-C1-C10 alkylsulfamoyl group. Specific examples thereof include: a linear dialkylsulfamoyl group such as dimethylsulfamoyl, diethylsulfamoyl, di-n-propylsulfamoyl, di-n-butylsulfamoyl, di-n-pentylsulfamoyl, di-n-hexylsulfamoyl, di-n-heptylsulfamoyl, di-n-octylsulfamoyl, di-n-nonylsulfamoyl and di-n-decylsulfamoyl; a branched dialkylsulfamoyl group such as diisopropylsulfamoyl, diisobutylsulfamoyl, di-sec-butylsulfamoyl, di-t-butylsulfamoyl, diisoamylsulfamoyl, di-t-amylsulfamoyl, diisohexylsulfamoyl, di-t-hexylsulfamoyl, diisoheptylsulfamoyl, di-t-heptylsulfamoyl, diisooctylsulfamoyl, di-t-octylsulfamoyl, di-(2-ethylhexyl)sulfamoyl, diisononylsulfamoyl and diisodecylsulfamoyl, preferably a sulfamoyl group having two C3-C10 branched alkyl groups; and a cyclic dialkylsulfamoyl group such as dicyclopropylsulfamoyl, dicyclobutylsulfamoyl, dicyclopentylsulfamoyl, dicyclohexylsulfamoyl and dicycloheptylsulfamoyl, preferably a sulfamoyl group having two C3-C7 cyclic alkyl groups. Preferred examples thereof include a linear or branched dialkylsulfamoyl group, more preferably a linear dialkylsulfamoyl group.

Examples of the monoarylsulfamoyl group preferably include a mono-C6-C12 arylsulfamoyl group. Specific examples thereof include phenylsulfamoyl, naphthylsulfamoyl and biphenylsulfamoyl.

Examples of the diarylsulfamoyl group preferably include a di-C6-C12 arylsulfamoyl group. Specific examples thereof include diphenylsulfamoyl, dinaphthylsulfamoyl and di(biphenyl)sulfamoyl.

Examples of the linear, branched or cyclic alkylsulfonyl group preferably include a C1-C12 alkylsulfonyl group. Specific examples thereof include: a linear alkylsulfonyl group such as methylsulfonyl, ethylsulfonyl, n-propylsulfonyl, n-butylsulfonyl, n-pentylsulfonyl, n-hexylsulfonyl, n-heptylsulfonyl, n-octylsulfonyl, n-nonylsulfonyl, n-decylsulfonyl, n-undecylsulfonyl and n-dodecylsulfonyl; a branched alkylsulfonyl group such as isopropylsulfonyl, isobutylsulfonyl, sec-butylsulfonyl, t-butylsulfonyl, isoamylsulfonyl, t-amylsulfonyl, isohexylsulfonyl, t-hexylsulfonyl, isoheptylsulfonyl, t-heptylsulfonyl, isooctylsulfonyl, t-octylsulfonyl, 2-ethylhexylsulfonyl, isononylsulfonyl, isodecylsulfonyl, isoundecylsulfonyl, t-undecylsulfonyl, isododecylsulfonyl and t-dodecylsulfonyl, preferably a C3-C12 branched alkylsulfonyl group; and a cyclic alkylsulfonyl group such as cyclopropylsulfonyl, cyclobutylsulfonyl, cyclopentylsulfonyl, cyclohexylsulfonyl and cycloheptylsulfonyl, preferably a C3-C7 cyclic alkylsulfonyl group. Preferred examples thereof include a linear or branched alkylsulfonyl group, more preferably a linear alkylsulfonyl group.

Examples of the arylsulfonyl group preferably include a C6-C12 arylsulfonyl group. Specific examples thereof include phenylsulfonyl, naphthylsulfonyl and biphenylsulfonyl.

Examples of the linear, branched or cyclic alkylthio group preferably include a C1-C10 alkylthio group. Specific examples thereof include: a linear alkylthio group such as methylthio, ethylthio, n-propylthio, n-butylthio, n-pentylthio, n-hexylthio, n-heptylthio, n-octylthio, n-nonylthio and n-decylthio; a branched alkylthio group such as isopropylthio, isobutylthio, sec-butylthio, t-butylthio, isoamylthio, t-amylthio, isohexylthio, t-hexylthio, isoheptylthio, t-heptylthio, isooctylthio, t-octylthio, 2-ethylhexylthio, isononylthio and isodecylthio, preferably a C3-C10 branched alkylthio group; and a cyclic alkylthio group such as cyclopropylthio, cyclobutylthio, cyclopentylthio, cyclohexylthio and cycloheptylthio, preferably a C3-C7 cyclic alkylthio group. Preferred examples thereof include a linear or branched alkylthio group, more preferably a linear alkylthio group.

Examples of the arylthio group preferably include a C6-C12 arylthio group. Specific examples thereof include phenylthio, naphthylthio and biphenylthio.

Examples of the linear, branched or cyclic monoalkylureido group preferably include a mono-C1-C10 alkylureido group. Specific examples thereof include: a linear monoalkylureido group such as methylureido, ethylureido, n-propylureido, n-butylureido, n-pentylureido, n-hexylureido, n-heptylureido, n-octylureido, n-nonylureido and n-decylureido; a branched monoalkylureido group such as isopropylureido, isobutylureido, sec-butylureido, t-butylureido, isoamylureido, t-amylureido, isohexylureido, t-hexylureido, isoheptylureido, t-heptylureido, isooctylureido, t-octylureido, 2-ethylhexylureido, isononylureido and isodecylureido, preferably a C3-C10 branched monoalkylureido group; and a cyclic monoalkylureido group such as cyclopropylureido, cyclobutylureido, cyclopentylureido, cyclohexylureido and cycloheptylureido, preferably a C3-C7 cyclic monoalkylureido group. Preferred examples thereof include a linear or branched monoalkylureido group, more preferably a linear monoalkylureido group.

Examples of the linear, branched or cyclic dialkylureido group preferably include a di-C1-C10 alkylureido group. Specific examples thereof include: a linear dialkylureido group such as dimethylureido, diethylureido, di-n-propylureido, di-n-butylureido, di-n-pentylureido, di-n-hexylureido, di-n-heptylureido, di-n-octylureido, di-n-nonylureido and di-n-decylureido; a branched dialkylureido group such as diisopropylureido, diisobutylureido, di-sec-butylureido, di-t-butylureido, diisoamylureido, di-t-amylureido, diisohexylureido, di-t-hexylureido, diisoheptylureido, di-t-heptylureido, diisooctylureido, di-t-octylureido, di-(2-ethylhexyl)ureido, diisononylureido and diisodecylureido, preferably an ureido group having two C3-C10 branched alkyl groups; and a cyclic dialkylureido group such as dicyclopropylureido, dicyclobutylureido, dicyclopentylureido, dicyclohexylureido and dicycloheptylureido, preferably an ureido group having two C3-C7 cyclic alkyl groups. Preferred examples thereof include a linear or branched dialkylureido group, more preferably a linear dialkylureido group.

Examples of the monoarylureido group preferably include a mono-C6-C12 arylureido group. Specific examples thereof include phenylureido, naphthylureido and biphenylureido.

Examples of the diarylureido group preferably include a di-C6-C12 arylureido group. Specific examples thereof include diphenylureido, dinaphthylureido and di(biphenyl)ureido.

Examples of the linear, branched or cyclic alkoxycarbonylamino group preferably include a C1-C10 alkoxycarbonylamino group. Specific examples thereof include: a linear alkoxycarbonylamino group such as methoxycarbonylamino, ethoxycarbonylamino, n-propoxycarbonylamino, n-butoxycarbonylamino, n-pentoxycarbonylamino, n-hexyloxycarbonylamino, n-heptoxycarbonylamino, n-octyloxycarbonylamino, n-nonyloxycarbonylamino and n-decyloxycarbonylamino; a branched alkoxycarbonylamino group such as isopropoxycarbonylamino, isobutoxycarbonylamino, sec-butoxycarbonylamino, t-butoxycarbonylamino, isoamyloxycarbonylamino, t-amyloxycarbonylamino, isohexyloxycarbonylamino, t-hexyloxycarbonylamino, isoheptoxycarbonylamino, t-heptoxycarbonylamino, isooctyloxycarbonylamino, t-octyloxycarbonylamino, 2-ethylhexyloxycarbonylamino, isononyloxycarbonylamino and isodecyloxycarbonylamino, preferably a C3-C10 branched alkoxycarbonylamino group; and a cyclic alkoxycarbonylamino group such as cyclopropoxycarbonylamino, cyclobutoxycarbonylamino, cyclopentoxycarbonylamino, cyclohexyloxycarbonylamino and cycloheptoxycarbonylamino, preferably a C3-C7 cyclic alkoxycarbonylamino group. Preferred examples thereof include a linear or branched alkoxycarbonylamino group, more preferably a linear alkoxycarbonylamino group.

Examples of the aryloxycarbonylamino group preferably include a C6-C12 aryloxycarbonylamino group. Specific examples thereof include phenylcarbonylamino, naphthylcarbonylamino and biphenylcarbonylamino.

Examples of the linear, branched or cyclic monoalkylamino group preferably include a mono-C1-C10 alkylamino group. Specific examples thereof include: a linear monoalkylamino group such as methylamino, ethylamino, n-propylamino, n-butylamino, n-pentylamino, n-hexylamino, n-heptylamino, n-octylamino, n-nonylamino and n-decylamino; a branched monoalkylamino group such as isopropylamino, isobutylamino, sec-butylamino, t-butylamino, isoamylamino, t-amylamino, isohexylamino, t-hexylamino, isoheptylamino, t-heptylamino, isooctylamino, t-octylamino, 2-ethylhexylamino, isononylamino and isodecylamino, preferably a C3-C10 branched monoalkylamino group; and a cyclic monoalkylamino group such as cyclopropylamino, cyclobutylamino, cyclopentylamino, cyclohexylamino and cycloheptylamino, preferably a C3-C7 cyclic monoalkylamino group. Preferred examples thereof include a linear or branched monoalkylamino group, more preferably a linear monoalkylamino group.

Examples of the linear, branched or cyclic dialkylamino group preferably include a di-C1-C10 alkylamino group. Specific examples thereof include: a linear dialkylamino group such as dimethylamino, diethylamino, di-n-propylamino, di-n-butylamino, di-n-pentylamino, di-n-hexylamino, di-n-heptylamino, di-n-octylamino, di-n-nonylamino and di-n-decylamino; a branched dialkylamino group such as diisopropylamino, diisobutylamino, di-sec-butylamino, di-t-butylamino, diisoamylamino, di-t-amylamino, diisohexylamino, di-t-hexylamino, diisoheptylamino, di-t-heptylamino, diisooctylamino, di-t-octylamino, di-(2-ethylhexyl)amino, diisononylamino and diisodecylamino, preferably an amino group having two C3-C10 branched alkyl groups; and a cyclic dialkylamino group such as dicyclopropylamino, dicyclobutylamino, dicyclopentylamino, dicyclohexylamino and dicycloheptylamino, preferably an amino group having two C3-C7 cyclic alkyl groups. Preferred examples thereof include a linear or branched dialkylamino group, more preferably a linear dialkylamino group.

Examples of the arylamino group preferably include a monoarylamino group and a diarylamino group. Examples of the monoarylamino group preferably include a mono-C6-C12 arylamino group. Specific examples thereof include phenylamino (anilino), naphthylamino and biphenylamino. Likewise, examples of the diarylamino group preferably include a di-C6-C12 arylamino group. Specific examples thereof include diphenylamino, dinaphthylamino and di(biphenyl)amino.

Examples of the halogen atom include a fluorine atom, a chlorine atom, a bromine atom and an iodine atom and preferably include a fluorine atom, a chlorine atom and a bromine atom.

These substituents on the alkyl group of $R^1$ may each be further substituted, and the substituent therefor may be also one or two, preferably one, of the aforementioned groups.

The alkyl group optionally having a substituent, represented by $R^1$ is preferably an unsubstituted alkyl group or an alkyl group substituted with an aryl group, particularly preferably an unsubstituted alkyl group.

In the formula (1), examples of the position of substitution with the substituent —HNCOR$^1$ include an ortho position, a meta position and a para position. An ortho position or a meta position is preferred.

Specific examples of the compound of the formula (1) can include, but are not limited to, compounds described in Table 1 below.

TABLE 1

| Compound No. | Structural formula |
| --- | --- |
| 1 | |
| 2 | |
| 3 | |

TABLE 1-continued

| Compound No. | Structural formula |
| --- | --- |
| 4 | *3-acetamidophenyl phenylurea structure* |
| 5 | *3-pentanamidophenyl phenylurea structure* |
| 6 | *3-pivalamidophenyl phenylurea structure* |
| 7 | *4-acetamidophenyl phenylurea structure* |
| 8 | *2-(cyclohexanecarboxamido)phenyl phenylurea structure* |
| 9 | *2-(3-phenylpropanamido)phenyl phenylurea structure* |

TABLE 1-continued
| Compound No. | Structural formula |
| --- | --- |
| 10 | 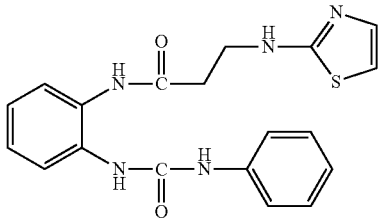 [SMILES: O=C(CCNc1nccs1)Nc1ccccc1NC(=O)Nc1ccccc1] |
| 11 | 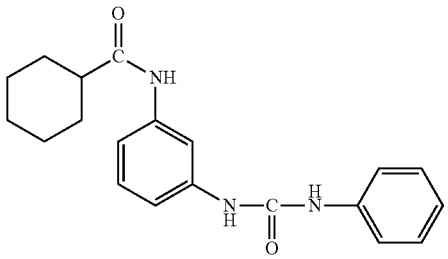 [SMILES: O=C(Nc1ccccc1)Nc1cccc(NC(=O)C2CCCCC2)c1] |
| 12 | 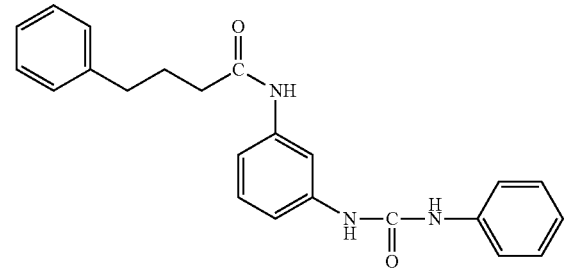 [SMILES: O=C(CCCc1ccccc1)Nc1cccc(NC(=O)Nc2ccccc2)c1] |
| 13 | 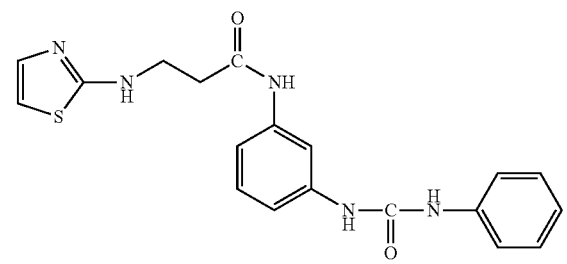 [SMILES: O=C(CCNc1nccs1)Nc1cccc(NC(=O)Nc2ccccc2)c1] |
| 14 | 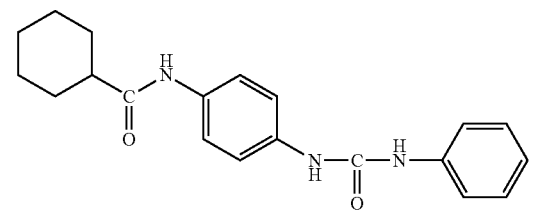 [SMILES: O=C(Nc1ccccc1)Nc1ccc(NC(=O)C2CCCCC2)cc1] |
| 15 | 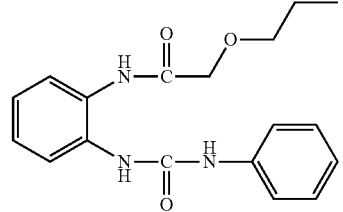 [SMILES: CCCOCC(=O)Nc1ccccc1NC(=O)Nc1ccccc1] |

TABLE 1-continued
| Compound No. | Structural formula |
|---|---|
| 16 | 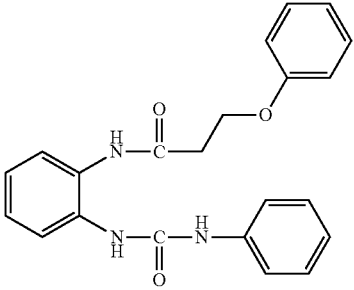 [SMILES: O=C(CCOc1ccccc1)Nc1ccccc1NC(=O)Nc1ccccc1] |
| 17 | 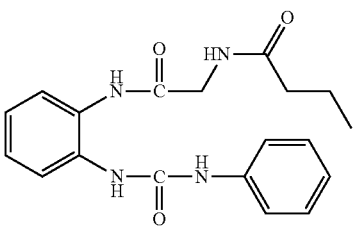 [SMILES: CCCC(=O)NCC(=O)Nc1ccccc1NC(=O)Nc1ccccc1] |
| 18 | 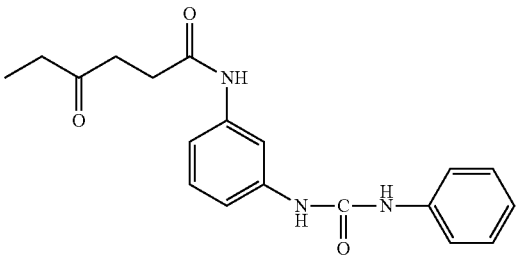 [SMILES: CCC(=O)CCC(=O)Nc1cccc(NC(=O)Nc2ccccc2)c1] |
| 19 | 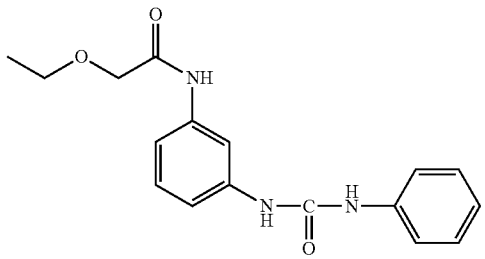 [SMILES: CCOCC(=O)Nc1cccc(NC(=O)Nc2ccccc2)c1] |
| 20 | 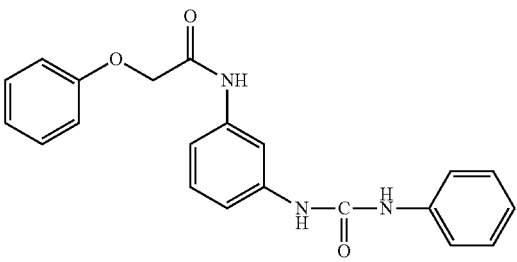 [SMILES: O=C(COc1ccccc1)Nc1cccc(NC(=O)Nc2ccccc2)c1] |
| 21 | 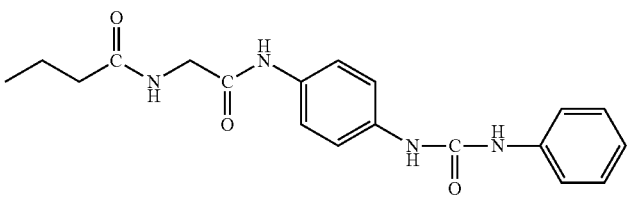 [SMILES: CCCC(=O)CCC(=O)Nc1ccc(NC(=O)Nc2ccccc2)cc1] |

TABLE 1-continued

| Compound No. | Structural formula |
| --- | --- |
| 22 | |
| 23 | |
| 24 | |
| 25 | |
| 26 | |
| 27 | |
| 28 | |

TABLE 1-continued

| Compound No. | Structural formula |
|---|---|
| 29 | butyl-SO2-NH-CH2-C(=O)-NH-[3-(PhNHC(=O)NH)-phenyl] |
| 30 | HO-(CH2)3-C(=O)-NH-[3-(PhNHC(=O)NH)-phenyl] |
| 31 | EtNH-C(=O)-NH-CH2-C(=O)-NH-[3-(PhNHC(=O)NH)-phenyl] |
| 32 | H2N-(CH2)3-C(=O)-NH-[3-(PhNHC(=O)NH)-phenyl] |
| 33 | Cl-(CH2)3-C(=O)-NH-[3-(PhNHC(=O)NH)-phenyl] |
| 34 | HO-(CH2)2-C(=O)-NH-[4-(PhNHC(=O)NH)-phenyl] |

TABLE 1-continued

| Compound No. | Structural formula |
|---|---|
| 35 | |
| 36 | |
| 37 | |
| 38 | |
| 39 | |
| 40 | |

TABLE 1-continued
| Compound No. | Structural formula |
| --- | --- |
| 41 | 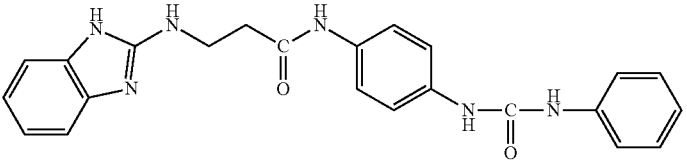 [SMILES: O=C(CCNc1nc2ccccc2[nH]1)Nc1ccc(NC(=O)Nc2ccccc2)cc1] |
| 42 | 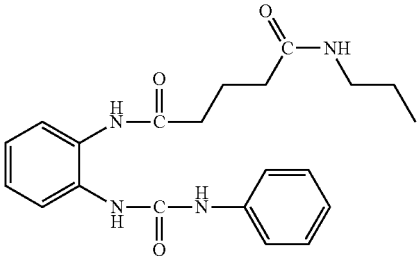 [SMILES: CCCNC(=O)CCCC(=O)Nc1ccccc1NC(=O)Nc1ccccc1] |
| 43 | 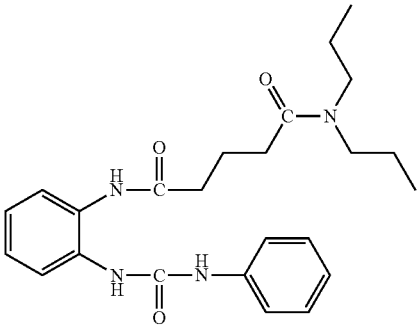 [SMILES: CCCN(CCC)C(=O)CCCC(=O)Nc1ccccc1NC(=O)Nc1ccccc1] |
| 44 | 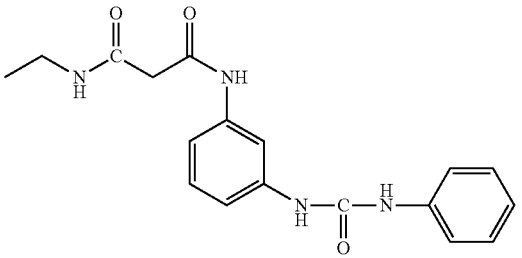 [SMILES: CCNC(=O)CC(=O)Nc1cccc(NC(=O)Nc2ccccc2)c1] |
| 45 | 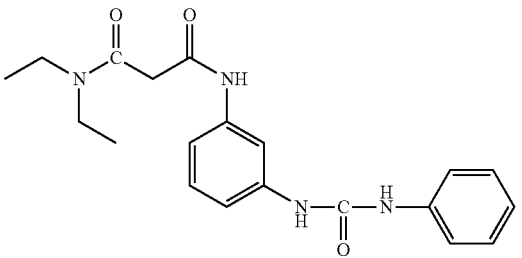 [SMILES: CCN(CC)C(=O)CC(=O)Nc1cccc(NC(=O)Nc2ccccc2)c1] |
| 46 | 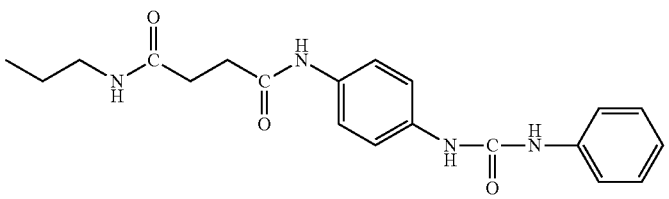 [SMILES: CCCNC(=O)CCC(=O)Nc1ccc(NC(=O)Nc2ccccc2)cc1] |

TABLE 1-continued

| Compound No. | Structural formula |
|---|---|
| 47 | |
| 48 | |
| 49 | |
| 50 | |
| 51 | |
| 52 | |
| 53 | |

TABLE 1-continued

| Compound No. | Structural formula |
| --- | --- |
| 54 | |
| 55 | |
| 56 | |
| 57 | |
| 58 | |
| 59 | |

TABLE 1-continued

| Compound No. | Structural formula |
|---|---|
| 60 | |
| 61 | |
| 62 | |
| 63 | |

Examples of $R^2$ to $R^6$ described in the formula (2) include a linear, branched or cyclic alkyl group, an arylalkyl group, an aryl group, a 5- or 6-membered heterocyclic group containing 1 to 3 atoms selected from a nitrogen atom, an oxygen atom and a sulfur atom as ring-constituting atoms, a 5- or 6-membered heterocyclylamino group containing 1 to 3 atoms selected from a nitrogen atom, an oxygen atom and a sulfur atom as ring-constituting atoms, a ring-fused heterocyclylamino group in which one benzene ring is fused with a 5- or 6-membered heterocyclic group containing 1 to 3 atoms selected from a nitrogen atom, an oxygen atom and a sulfur atom as ring-constituting atoms, a linear, branched or cyclic alkoxy group, an aryloxy group, a linear, branched or cyclic alkylcarbonylamino group, an arylcarbonylamino group, a linear, branched or cyclic alkylcarbonyloxy group, an arylcarbonyloxy group, a linear, branched or cyclic alkylcarbonyl group, an arylcarbonyl group, a carbamoyl group, a linear, branched or cyclic monoalkylcarbamoyl group, a linear, branched or cyclic dialkylcarbamoyl group, a monoarylcarbamoyl group, a diarylcarbamoyl group, a linear, branched or cyclic alkoxycarbonyl group, an aryloxycarbonyl group, a linear, branched or cyclic alkylsulfonylamino group, an arylsulfonylamino group, a sulfamoyl group, a linear, branched or cyclic monoalkylsulfamoyl group, a linear, branched or cyclic dialkylsulfamoyl group, a monoarylsulfamoyl group, a diarylsulfamoyl group, a hydroxy group, a linear, branched or cyclic alkylsulfonyl group, an arylsulfonyl group, a linear, branched or cyclic alkylthio group, an arylthio group, an ureido group, a linear, branched or cyclic monoalkylureido group, a linear, branched or cyclic dialkylureido group, a monoarylureido group, a linear, branched or cyclic alkoxycarbonylamino group, an aryloxycarbonylamino group, a cyano group, a nitro group, an amino group, a linear, branched or cyclic monoalkylamino group, a linear, branched or cyclic dialkylamino group, an arylamino group, a mercapto group which means a group represented by "—SH" in the present specification, a carboxy group, a sulfone group and a halogen atom.

Examples of the linear, branched or cyclic alkyl group preferably include a C1-C10 alkyl group. Specific examples thereof include: a linear alkyl group such as methyl, ethyl, n-propyl, n-butyl, n-pentyl, n-hexyl, n-heptyl, n-octyl, n-nonyl, and n-decyl, vinyl; allyl; a branched alkyl group such as isopropyl, isobutyl, sec-butyl, t-butyl, isoamyl, t-amyl, isohexyl, t-hexyl, isoheptyl, t-heptyl, isooctyl, t-octyl, 2-ethylhexyl, isononyl and isodecyl, preferably a C3-C10 branched alkyl group; and a cyclic alkyl group such as cyclopropyl, cyclobutyl, cyclopentyl, cyclohexyl and cycloheptyl, preferably a C3-C7 cyclic alkyl group. Preferred examples thereof include a linear or branched alkyl group, more preferably a linear alkyl group.

Examples of the arylalkyl group preferably include a C6-C12 aryl-C1-C10 alkyl group, more preferably a phenyl-C1-C6 alkyl group, further preferably a phenyl-C1-C4 alkyl group. Specific examples thereof include: an arylalkyl group having a linear alkyl moiety, such as phenylmethyl, 2-phenylethyl, 3-phenylpropyl, 4-phenylbutyl, 5-phenylpentyl and 5-phenylhexyl; and an arylalkyl group having a branched alkyl moiety, such as α-methylbenzyl.

Examples of the aryl group preferably include a C6-C12 aryl group. Specific examples thereof include phenyl, naphthyl and biphenyl.

The 5- or 6-membered heterocyclic group containing 1 to 3 atoms selected from a nitrogen atom, an oxygen atom and a sulfur atom as ring-constituting atoms preferably has an aromatic ring as its heterocyclic moiety. Specific examples thereof include: a 5-membered alicyclic heterocyclic group such as pyrrolidinyl, tetrahydrofuryl, tetrahydrothiophen-2-yl and tetrahydrothiophen-3-yl; a 6-membered alicyclic heterocyclic group such as piperidinyl, piperazinyl, dioxan-2-yl, morpholinyl and thiomorpholinyl; a 5-membered aromatic heterocyclic group such as pyrrole, pyrazole, imidazole, triazole, furyl, thiophen-2-yl, thiophen-3-yl, oxazole and thiazole; and an aromatic 6-membered heterocyclic group such as pyridine, pyrazine, pyridazine and triazine. The ring-constituting atom is preferably selected from a nitrogen atom and a sulfur atom.

The 5- or 6-membered heterocyclylamino group containing 1 to 3 atoms selected from a nitrogen atom, an oxygen atom and a sulfur atom as ring-constituting atoms preferably has an aromatic ring as its heterocyclic moiety. Specific examples thereof include: a 5-membered alicyclic heterocyclylamino group such as pyrrolidinylamino, tetrahydrofurylamino, tetrahydrothiophen-2-yl amino and tetrahydrothiophen-3-yl amino; a 6-membered alicyclic heterocyclylamino group such as piperidinylamino, piperazinylamino, dioxan-2-yl amino, morpholinylamino, and thiomorpholinylamino; a 5-membered aromatic heterocyclylamino group such as pyrrolamino, pyrazolamino, imidazolamino, triazolamino, furylamino, thiophen-2-yl amino, thiophen-3-yl amino, oxazolamino and thiazolamino; and a 6-membered aromatic heterocyclylamino group such as pyridylamino, pyrazylamino, pyridazinylamino and triazinylamino. The ring-constituting atom is preferably selected from a nitrogen atom and a sulfur atom.

The ring-fused heterocyclylamino group in which one benzene ring is fused with a 5- or 6-membered heterocyclic group containing 1 to 3 atoms selected from a nitrogen atom, an oxygen atom and a sulfur atom as ring-constituting atoms preferably has an aromatic ring as its heterocyclic moiety. Specific examples thereof include: a ring-fused heterocyclylamino group having a 5-membered alicyclic heterocyclic ring as its heterocyclic moiety, such as phthalanylamino; a ring-fused heterocyclylamino group having a 6-membered alicyclic heterocyclic ring as its heterocyclic moiety, such as benzopyranylamino; a ring-fused heterocyclylamino group having a 5-membered aromatic heterocyclic ring as its heterocyclic moiety, such as benzopyrrolamino, benzopyrazolamino, benzimidazolamino, benzotriazolamino, benzofuranylamino, benzothiophen-2-yl amino, benzothiophen-3-yl amino, benzoxazolamino and benzothiazolamino; and a ring-fused heterocyclylamino group having a 6-membered aromatic heterocyclic ring as its heterocyclic moiety, such as quinolinylamino, cinnolinylamino, phthalazinylamino, quinazolinylamino and quinoxalinylamino. The ring-constituting atom is preferably selected from a nitrogen atom and a sulfur atom.

Examples of the linear, branched or cyclic alkoxy group preferably include a C1-C10 alkoxy group. Specific examples thereof include: a linear alkoxy group such as methoxy, ethoxy, n-propoxy, n-butoxy, n-pentoxy, n-hexyloxy, n-heptoxy, n-octyloxy, n-nonyloxy and n-decyloxy; a branched alkoxy group such as isopropoxy, isobutoxy, sec-butoxy, t-butoxy, isoamyloxy, t-amyloxy, isohexyloxy, t-hexyloxy, isoheptoxy, t-heptoxy, isooctyloxy, t-octyloxy, 2-ethylhexyloxy, isononyloxy and isodecyloxy, preferably a C3-C10 alkoxy group; and a cyclic alkoxy group such as cyclopropoxy, cyclobutoxy, cyclopentoxy, cyclohexyloxy and cycloheptoxy, preferably a C3-C7 cyclic alkoxy group. Preferred examples thereof include a linear or branched alkoxy group.

Examples of the aryloxy group preferably include a C6-C12 aryloxy group. Specific examples thereof include phenoxy, naphthyloxy and biphenyloxy.

Examples of the linear, branched or cyclic alkylcarbonylamino group preferably include a C1-C10 alkylcarbonylamino group. Specific examples thereof include: a linear alkylcarbonylamino group such as methylcarbonylamino, ethylcarbonylamino, n-propylcarbonylamino, n-butylcarbonylamino, n-pentylcarbonylamino, n-hexylcarbonylamino, n-heptylcarbonylamino, n-octylcarbonylamino, n-nonylcarbonylamino and n-decylcarbonylamino; a branched alkylcarbonylamino group such as isopropylcarbonylamino, isobutylcarbonylamino, sec-butylcarbonylamino, t-butylcarbonylamino, isoamylcarbonylamino, t-amylcarbonylamino, isohexylcarbonylamino, t-hexylcarbonylamino, isoheptylcarbonylamino, t-heptylcarbonylamino, isooctylcarbonylamino, t-octylcarbonylamino, 2-ethylhexylcarbonylamino, isononylcarbonylamino and isodecylcarbonylamino, preferably a C3-C10 branched alkylcarbonylamino group; and a cyclic alkylcarbonylamino group such as cyclopropylcarbonylamino, cyclobutylcarbonylamino, cyclopentylcarbonylamino, cyclohexylcarbonylamino and cycloheptylcarbonylamino, preferably a C3-C7 cyclic alkylcarbonylamino group. Preferred examples thereof include a linear or branched alkylcarbonylamino group, more preferably a linear alkylcarbonylamino group.

Examples of the arylcarbonylamino group preferably include a C6-C12 arylcarbonylamino group. Specific examples thereof include phenylcarbonylamino, naphthylcarbonylamino and biphenylcarbonylamino.

Examples of the linear, branched or cyclic alkylcarbonyloxy group preferably include a C1-C10 alkylcarbonyloxy group. Specific examples thereof include: a linear alkylcarbonyloxy group such as methylcarbonyloxy, ethylcarbonyloxy, n-propylcarbonyloxy, n-butylcarbonyloxy, n-pentylcarbonyloxy, n-hexylcarbonyloxy, n-heptylcarbonyloxy, n-octylcarbonyloxy, n-nonylcarbonyloxy and n-decylcarbonyloxy; a branched alkylcarbonyloxy group such as isopropylcarbonyloxy, isobutylcarbonyloxy, sec-butylcarbonyloxy, t-butylcarbonyloxy, isoamylcarbonyloxy, t-amylcarbonyloxy, isohexylcarbonyloxy, t-hexylcarbonyloxy, isoheptylcarbonyloxy, t-heptylcarbonyloxy, isooctylcarbonyloxy, t-octylcarbonyloxy, 2-ethylhexylcarbonyloxy, isononylcarbonyloxy and isodecylcarbonyloxy, preferably a C3-C10 branched alkylcarbonyloxy group; and a cyclic alkylcarbonyloxy group such as cyclopropylcarbonyloxy, cyclobutylcarbonyloxy, cyclopentylcarbonyloxy, cyclohexylcarbonyloxy and cycloheptylcarbonyloxy, preferably a C3-C7 cyclic alkylcarbonyloxy group. Preferred examples thereof include a linear or branched alkylcarbonyloxy group, more preferably a linear alkylcarbonyloxy group.

Examples of the arylcarbonyloxy group preferably include a C6-C12 arylcarbonyloxy group. Specific examples thereof include phenylcarbonyloxy, naphthylcarbonyloxy and biphenylcarbonyloxy.

Examples of the linear, branched or cyclic alkylcarbonyl group preferably include a C1-C10 alkylcarbonyl group. Specific examples thereof include: a linear alkylcarbonyl group such as methylcarbonyl, ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl and n-decylcarbonyl; a branched alkylcarbonyl group such as isopropylcarbonyl, isobutylcarbonyl, sec-butylcarbonyl, t-butylcarbonyl, isoamylcarbonyl, t-amylcarbonyl, isohexylcarbonyl, t-hexylcarbonyl, isoheptylcarbonyl, t-heptylcarbonyl, isooctylcarbonyl, t-octylcarbonyl, 2-ethylhexylcarbonyl, isononylcarbonyl and isodecylcarbonyl, preferably a C3-C10 branched alkylcarbonyl group; and a cyclic alkylcarbonyl group such as cyclopropylcarbonyl, cyclobutylcarbonyl, cyclopentylcarbonyl, cyclohexylcarbonyl and cycloheptylcarbonyl, preferably a C3-C7 cyclic alkylcarbonyl group. Preferred examples thereof include a linear or branched alkylcarbonyl group, more preferably a linear alkylcarbonyl group.

Examples of the arylcarbonyl group preferably include a C6-C12 arylcarbonyl group. Specific examples thereof include phenylcarbonyl (benzoyl), naphthylcarbonyl and biphenylcarbonyl.

Examples of the linear, branched or cyclic monoalkylcarbamoyl group preferably include a mono-C1-C10 alkylcarbamoyl group. Specific examples thereof include: a linear monoalkylcarbamoyl group such as methylcarbamoyl, ethylcarbamoyl, n-propylcarbamoyl, n-butylcarbamoyl, n-pentylcarbamoyl, n-hexylcarbamoyl, n-heptylcarbamoyl, n-octylcarbamoyl, n-nonylcarbamoyl and n-decylcarbamoyl; a branched monoalkylcarbamoyl group such as isopropylcarbamoyl, isobutylcarbamoyl, sec-butylcarbamoyl, t-butylcarbamoyl, isoamylcarbamoyl, t-amylcarbamoyl, isohexylcarbamoyl, t-hexylcarbamoyl, isoheptylcarbamoyl, t-heptylcarbamoyl, isooctylcarbamoyl, t-octylcarbamoyl, 2-ethylhexylcarbamoyl, isononylcarbamoyl and isodecylcarbamoyl, preferably a C3-C10 branched monoalkylcarbamoyl group; and a cyclic monoalkylcarbamoyl group such as cyclopropylcarbamoyl, cyclobutylcarbamoyl, cyclopentylcarbamoyl, cyclohexylcarbamoyl and cycloheptylcarbamoyl, preferably a C3-C7 cyclic monoalkylcarbamoyl group. Preferred examples thereof include a linear or branched monoalkylcarbamoyl group, more preferably a linear monoalkylcarbamoyl group.

Examples of the linear, branched or cyclic dialkylcarbamoyl group preferably include a di-C1-C10 alkylcarbamoyl group. Specific examples thereof include: a linear dialkylcarbamoyl group such as dimethylcarbamoyl, diethylcarbamoyl, di-n-propylcarbamoyl, di-n-butylcarbamoyl, di-n-pentylcarbamoyl, di-n-hexylcarbamoyl, di-n-heptylcarbamoyl, di-n-octylcarbamoyl, di-n-nonylcarbamoyl and di-n-decylcarbamoyl; a branched dialkylcarbamoyl group such as diisopropylcarbamoyl, diisobutylcarbamoyl, di-sec-butylcarbamoyl, di-t-butylcarbamoyl, diisoamylcarbamoyl, di-t-amylcarbamoyl, diisohexylcarbamoyl, di-t-hexylcarbamoyl, diisoheptylcarbamoyl, di-t-heptylcarbamoyl, diisooctylcarbamoyl, di-t-octylcarbamoyl, di-(2-ethylhexyl)carbamoyl, diisononylcarbamoyl and diisodecylcarbamoyl, preferably a carbamoyl group having two C3-C10 branched alkyl groups; and a cyclic dialkylcarbamoyl group such as dicyclopropylcarbamoyl, dicyclobutylcarbamoyl, dicyclopentylcarbamoyl, dicyclohexylcarbamoyl and dicycloheptylcarbamoyl, preferably a carbamoyl group having two C3-C7 cyclic alkyl groups. Preferred examples thereof include a linear or branched dialkylcarbamoyl group, more preferably a linear dialkylcarbamoyl group.

Examples of the monoarylcarbamoyl group preferably include a mono-C6-C12 arylcarbamoyl group. Specific examples thereof include phenylcarbamoyl, naphthylcarbamoyl and biphenylcarbamoyl.

Examples of the diarylcarbamoyl group preferably include a di-C6-C12 arylcarbamoyl group. Specific examples thereof include diphenylcarbamoyl, dinaphthylcarbamoyl and di(biphenyl)carbamoyl.

Examples of the linear, branched or cyclic alkoxycarbonyl group preferably include a C1-C10 alkoxycarbonyl group. Specific examples thereof include: a linear alkoxycarbonyl group such as methoxycarbonyl, ethoxycarbonyl, n-propoxycarbonyl, n-butoxycarbonyl, n-pentoxycarbonyl, n-hexyloxycarbonyl, n-heptoxycarbonyl, n-octyloxycarbonyl, n-nonyloxycarbonyl and n-decyloxycarbonyl; a branched alkoxycarbonyl group such as isopropoxycarbonyl, isobutoxycarbonyl, sec-butoxycarbonyl, t-butoxycarbonyl, isoamyloxycarbonyl, t-amyloxycarbonyl, isohexyloxycarbonyl, t-hexyloxycarbonyl, isoheptoxycarbonyl, t-heptoxycarbonyl, isooctyloxycarbonyl, t-octyloxycarbonyl, 2-ethylhexyloxycarbonyl, isononyloxycarbonyl and isodecyloxycarbonyl, preferably a C3-C10 branched alkoxycarbonyl group; and a cyclic alkoxycarbonyl group such as cyclopropoxycarbonyl, cyclobutoxycarbonyl, cyclopentoxycarbonyl, cyclohexyloxycarbonyl and cycloheptoxycarbonyl, preferably a C3-C7 cyclic alkoxycarbonyl group. Preferred examples thereof include a linear or branched alkoxycarbonyl group, more preferably a linear alkoxycarbonyl group.

Examples of the aryloxycarbonyl group preferably include a C6-C12 aryloxycarbonyl group. Specific examples thereof include phenoxycarbonyl, naphthyloxycarbonyl and biphenyloxycarbonyl.

Examples of the linear, branched or cyclic alkylsulfonylamino group preferably include a C1-C10 alkylsulfonylamino group. Specific examples thereof include: a linear alkylsulfonylamino group such as methylsulfonylamino, ethylsulfonylamino, n-propylsulfonylamino, n-butylsulfonylamino, n-pentylsulfonylamino, n-hexylsulfonylamino, n-heptylsulfonylamino, n-octylsulfonylamino, n-nonylsulfonylamino and n-decylsulfonylamino; a branched alkylsulfonylamino group such as isopropylsulfonylamino, isobutylsulfonylamino, sec-butylsulfonylamino, t-butylsulfonylamino, isoamylsulfonylamino, t-amylsulfonylamino, isohexylsulfonylamino, t-hexylsulfonylamino, isoheptylsulfonylamino, t-heptylsulfonylamino, isooctylsulfonylamino, t-octylsulfonylamino, 2-ethylhexylsulfonylamino, isononylsulfonylamino and isodecylsulfonylamino, preferably a C3-C10 branched alkylsulfonylamino group; and a cyclic alkylsulfonylamino group such as cyclopropylsulfonylamino, cyclobutylsulfonylamino, cyclopentylsulfonylamino, cyclohexylsulfonylamino and cycloheptylsulfonylamino, preferably a C3-C7 cyclic alkylsulfonylamino group. Preferred examples thereof include a linear or branched alkylsulfonylamino group, more preferably a linear alkylsulfonylamino group.

Examples of the arylsulfonylamino group preferably include a C6-C12 arylsulfonylamino group. Specific examples thereof include phenylsulfonylamino, toluenesulfonylamino, naphthylsulfonylamino and biphenylsulfonylamino.

Examples of the linear, branched or cyclic monoalkylsulfamoyl group preferably include a mono-C1-C10 alkylsulfamoyl group. Specific examples thereof include: a linear monoalkylsulfamoyl group such as methylsulfamoyl, ethylsulfamoyl, n-propylsulfamoyl, n-butylsulfamoyl, n-pentylsulfamoyl, n-hexylsulfamoyl, n-heptylsulfamoyl, n-octylsulfamoyl, n-nonylsulfamoyl and n-decylsulfamoyl; a branched monoalkylsulfamoyl group such as isopropylsulfamoyl, isobutylsulfamoyl, sec-butylsulfamoyl, t-butylsulfamoyl, isoamylsulfamoyl, t-amylsulfamoyl, isohexylsulfamoyl, t-hexylsulfamoyl, isoheptylsulfamoyl, t-heptylsulfamoyl, isooctylsulfamoyl, t-octylsulfamoyl, 2-ethylhexylsulfamoyl, isononylsulfamoyl and isodecylsulfamoyl, preferably a C3-C10 branched monoalkylsulfamoyl group; and a cyclic monoalkylsulfamoyl group such as cyclopropylsulfamoyl, cyclobutylsulfamoyl, cyclopentylsulfamoyl, cyclohexylsulfamoyl and cycloheptylsulfamoyl, preferably a C3-C7 cyclic monoalkylsulfamoyl group. Preferred examples thereof include a linear or branched monoalkylsulfamoyl group, more preferably a linear monoalkylsulfamoyl group.

Examples of the linear, branched or cyclic dialkylsulfamoyl group preferably include a di-C1-C10 alkylsulfamoyl group. Specific examples thereof include: a linear dialkylsulfamoyl group such as dimethylsulfamoyl, diethylsulfamoyl, di-n-propylsulfamoyl, di-n-butylsulfamoyl, di-n-pentylsulfamoyl, di-n-hexylsulfamoyl, di-n-heptylsulfamoyl, di-n-octylsulfamoyl, di-n-nonylsulfamoyl and di-n-decylsulfamoyl; a branched dialkylsulfamoyl group such as diisopropylsulfamoyl, diisobutylsulfamoyl, di-sec-butylsulfamoyl, di-t-butylsulfamoyl, diisoamylsulfamoyl, di-t-amylsulfamoyl, diisohexylsulfamoyl, di-t-hexylsulfamoyl, diisoheptylsulfamoyl, di-t-heptylsulfamoyl, diisooctylsulfamoyl, di-t-octylsulfamoyl, di-(2-ethylhexyl)sulfamoyl, diisononylsulfamoyl and diisodecylsulfamoyl, preferably a sulfamoyl group having two C3-C10 branched alkyl groups; and a cyclic dialkylsulfamoyl group such as dicyclopropylsulfamoyl, dicyclobutylsulfamoyl, dicyclopentylsulfamoyl, dicyclohexylsulfamoyl and dicycloheptylsulfamoyl, preferably a sulfamoyl group having two C3-C7 cyclic alkyl groups. Preferred examples thereof include a linear or branched dialkylsulfamoyl group, more preferably a linear dialkylsulfamoyl group.

Examples of the monoarylsulfamoyl group preferably include a mono-C6-C12 arylsulfamoyl group. Specific examples thereof include phenylsulfamoyl, naphthylsulfamoyl and biphenylsulfamoyl.

Examples of the diarylsulfamoyl group preferably include a di-C6-C12 arylsulfamoyl group. Specific examples thereof include diphenylsulfamoyl, dinaphthylsulfamoyl and di(biphenyl)sulfamoyl.

Examples of the linear, branched or cyclic alkylsulfonyl group preferably include a C1-C12 alkylsulfonyl group. Specific examples thereof include: a linear alkylsulfonyl group such as methylsulfonyl, ethylsulfonyl, n-propylsulfonyl, n-butylsulfonyl, n-pentylsulfonyl, n-hexylsulfonyl, n-heptylsulfonyl, n-octylsulfonyl, n-nonylsulfonyl, n-decylsulfonyl, n-undecylsulfonyl and n-dodecylsulfonyl; a branched alkylsulfonyl group such as isopropylsulfonyl, isobutylsulfonyl, sec-butylsulfonyl, t-butylsulfonyl, isoamylsulfonyl, t-amylsulfonyl, isohexylsulfonyl, t-hexylsulfonyl, isoheptylsulfonyl, t-heptylsulfonyl, isooctylsulfonyl, t-octylsulfonyl, 2-ethylhexylsulfonyl, isononylsulfonyl, isodecylsulfonyl, isoundecylsulfonyl, t-undecylsulfonyl, isododecylsulfonyl and t-dodecylsulfonyl, preferably a C3-C12 branched alkylsulfonyl group; and a cyclic alkylsulfonyl group such as cyclopropylsulfonyl, cyclobutylsulfonyl, cyclopentylsulfonyl, cyclohexylsulfonyl and cycloheptylsulfonyl, preferably a C3-C7 cyclic alkylsulfonyl group. Preferred examples thereof include a linear or branched alkylsulfonyl group, more preferably a linear alkylsulfonyl group.

Examples of the arylsulfonyl group preferably include a C6-C12 arylsulfonyl group. Specific examples thereof include phenylsulfonyl, naphthylsulfonyl and biphenylsulfonyl.

Examples of the linear, branched or cyclic alkylthio group preferably include a C1-C10 alkylthio group. Specific examples thereof include: a linear alkylthio group such as methylthio, ethylthio, n-propylthio, n-butylthio, n-pentylthio, n-hexylthio, n-heptylthio, n-octylthio, n-nonylthio and n-decylthio; a branched alkylthio group such as isopropylthio, isobutylthio, sec-butylthio, t-butylthio, isoamylthio, t-amylthio, isohexylthio, t-hexylthio, isoheptylthio, t-heptylthio, isooctylthio, t-octylthio, 2-ethylhexylthio, isononylthio and isodecylthio, preferably a C3-C10 branched alkylthio group; and a cyclic alkylthio group such as cyclopropylthio, cyclobutylthio, cyclopentylthio, cyclohexylthio and cycloheptylthio, preferably a C3-C7 cyclic alkylthio group. Preferred examples thereof include a linear or branched alkylthio group, more preferably a linear alkylthio group.

Examples of the arylthio group preferably include a C6-C12 arylthio group. Specific examples thereof include phenylthio, naphthylthio and biphenylthio.

Examples of the linear, branched or cyclic monoalkylureido group preferably include a mono-C1-C10 alkylureido group. Specific examples thereof include: a linear monoalkylureido group such as methylureido, ethylureido, n-propylureido, n-butylureido, n-pentylureido, n-hexylureido, n-heptylureido, n-octylureido, n-nonylureido and n-decylureido; a branched monoalkylureido group such as isopropylureido, isobutylureido, sec-butylureido, t-butylureido, isoamylureido, t-amylureido, isohexylureido, t-hexylureido, isoheptylureido, t-heptylureido, isooctylureido, t-octylureido, 2-ethylhexylureido, isononylureido and isodecylureido, preferably a C3-C10 branched monoalkylureido group; and a cyclic monoalkylureido group such as cyclopropylureido, cyclobutylureido, cyclopentylureido, cyclohexylureido and cycloheptylureido, preferably a C3-C7 cyclic monoalkylureido group. Preferred examples thereof include a linear or branched monoalkylureido group, more preferably a linear monoalkylureido group.

Examples of the linear, branched or cyclic dialkylureido group preferably include a di-C1-C10 alkylureido group. Specific examples thereof include: a linear dialkylureido group such as dimethylureido, diethylureido, di-n-propylureido, di-n-butylureido, di-n-pentylureido, di-n-hexylureido, di-n-heptylureido, di-n-octylureido, di-n-nonylureido and di-n-decylureido; a branched dialkylureido group such as diisopropylureido, diisobutylureido, di-sec-butylureido, di-t-butylureido, diisoamylureido, di-t-amylureido, diisohexylureido, di-t-hexylureido, diisoheptylureido, di-t-heptylureido, diisooctylureido, di-t-octylureido, di-(2-ethylhexyl)ureido, diisononylureido and diisodecylureido, preferably an ureido group having two C3-C10 branched alkyl groups; and a cyclic dialkylureido group such as dicyclopropylureido, dicyclobutylureido, dicyclopentylureido, dicyclohexylureido and dicycloheptylureido, preferably an ureido group having two C3-C7 cyclic alkyl groups. Preferred examples thereof include a linear or branched dialkylureido group, more preferably a linear dialkylureido group.

Examples of the monoarylureido group preferably include a mono-C6-C12 arylureido group. Specific examples thereof include phenylureido, naphthylureido and biphenylureido.

Examples of the diarylureido group preferably include a di-C6-C12 arylureido group. Specific examples thereof include diphenylureido, dinaphthylureido and di(biphenyl)ureido.

Examples of the linear, branched or cyclic alkoxycarbonylamino group preferably include a C1-C10 alkoxycarbonylamino group. Specific examples thereof include: a linear alkoxycarbonylamino group such as methoxycarbonylamino, ethoxycarbonylamino, n-propoxycarbonylamino, n-butoxycarbonylamino, n-pentoxycarbonylamino, n-hexyloxycarbonylamino, n-heptoxycarbonylamino, n-octyloxycarbonylamino, n-nonyloxycarbonylamino and n-decyloxycarbonylamino; a branched alkoxycarbonylamino group such as isopropoxycarbonylamino, isobutoxycarbonylamino, sec-butoxycarbonylamino, t-butoxycarbonylamino, isoamyloxycarbonylamino, t-amyloxycarbonylamino, isohexyloxycarbonylamino, t-hexyloxycarbonylamino, isoheptoxycarbonylamino, t-heptoxycarbonylamino, isooctyloxycarbonylamino, t-octyloxycarbonylamino, 2-ethylhexyloxycarbonylamino, isononyloxycarbonylamino and isodecyloxycarbonylamino, preferably a C3-C10 branched alkoxycarbonylamino group; and a cyclic alkoxycarbonylamino group such as cyclopropoxycarbonylamino, cyclobutoxycarbonylamino, cyclopentoxycarbonylamino, cyclohexyloxycarbonylamino and cycloheptoxycarbonylamino, preferably a C3-C7 cyclic alkoxycarbonylamino group. Preferred examples thereof include a linear or branched alkoxycarbonylamino group, more preferably a linear alkoxycarbonylamino group.

Examples of the aryloxycarbonylamino group preferably include a C6-C12 aryloxycarbonylamino group. Specific examples thereof include phenylcarbonylamino, naphthylcarbonylamino and biphenylcarbonylamino.

Examples of the linear, branched or cyclic monoalkylamino group preferably include a mono-C1-C10 alkylamino group. Specific examples thereof include: a linear monoalkylamino group such as methylamino, ethylamino, n-propylamino, n-butylamino, n-pentylamino, n-hexylamino, n-heptylamino, n-octylamino, n-nonylamino and n-decylamino; a branched monoalkylamino group such as isopropylamino, isobutylamino, sec-butylamino, t-butylamino, isoamylamino, t-amylamino, isohexylamino, t-hexylamino, isoheptylamino, t-heptylamino, isooctylamino, t-octylamino, 2-ethylhexylamino, isononylamino and isodecylamino, preferably a C3-C10 branched monoalkylamino group; and a cyclic monoalkylamino group such as cyclopropylamino, cyclobutylamino, cyclopentylamino, cyclohexylamino and cycloheptylamino, preferably a C3-C7 cyclic monoalkylamino group. Preferred examples thereof include a linear or branched monoalkylamino group, more preferably a linear monoalkylamino group.

Examples of the linear, branched or cyclic dialkylamino group preferably include a di-C1-C10 alkylamino group. Specific examples thereof include: a linear dialkylamino group such as dimethylamino, diethylamino, di-n-propylamino, di-n-butylamino, di-n-pentylamino, di-n-hexylamino, di-n-heptylamino, di-n-octylamino, di-n-nonylamino and di-n-decylamino; a branched dialkylamino group such as diisopropylamino, diisobutylamino, di-sec-butylamino, di-t-butylamino, diisoamylamino, di-t-amylamino, diisohexylamino, di-t-hexylamino, diisoheptylamino, di-t-heptylamino, diisooctylamino, di-t-octylamino, di-(2-ethylhexyl)amino, diisononylamino and diisodecylamino, preferably an amino group having two C3-C10 branched alkyl groups; and a cyclic dialkylamino group such as dicyclopropylamino, dicyclobutylamino, dicyclopentylamino, dicyclohexylamino and dicycloheptylamino, preferably an amino group having two C3-C7 cyclic alkyl groups. Preferred examples thereof include a linear or branched dialkylamino group, more preferably a linear dialkylamino group.

Examples of the arylamino group preferably include a monoarylamino group and a diarylamino group. Examples of the mono-C6-C12 arylamino group preferably include a mono-C6-C12 arylamino group. Specific examples thereof include phenylamino (anilino), naphthylamino and biphenylamino. Likewise, examples of the diarylamino group include a di-C6-C12 arylamino group. Specific examples thereof include diphenylamino, dinaphthylamino and di(biphenyl)amino.

Examples of the halogen atom include a fluorine atom, a chlorine atom, a bromine atom and an iodine atom and preferably include a fluorine atom, a chlorine atom and a bromine atom.

These substituents of $R_2$ to $R_6$ may each be further substituted, and the substituent therefor may be also one or two groups, preferably one group, selected from the aforementioned substituents.

Each of $R^2$ to $R^6$ is preferably a group selected from the group consisting of a hydrogen atom, an alkyl group, an arylalkyl group, a 5- or 6-membered heterocyclylamino group containing 1 to 3 atoms selected from a nitrogen atom, an oxygen atom and a sulfur atom as ring-constituting atoms, a ring-fused heterocyclylamino group in which one benzene ring is fused with a 5- or 6-membered heterocyclic group containing 1 to 3 atoms selected from a nitrogen atom, an oxygen atom and a sulfur atom as ring-constituting atoms, an alkoxy group, an aryloxy group, an alkylcarbonylamino group, a carbamoyl group, a hydroxy group, a carboxy group, an alkylsulfonyl group, an arylthio group, a cyano group, an amino group, an arylamino group and a halogen atom, particularly preferably a hydrogen atom or an alkyl group.

Specific examples of the compound of the formula (2) can include, but are not limited to, compounds described in Table 2 below.

TABLE 2

| Compound No. | Structural formula |
|---|---|
| 64 | 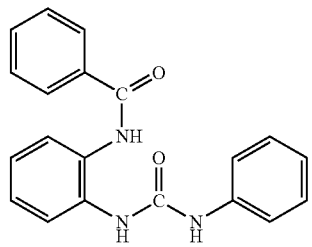 [SMILES: O=C(Nc1ccccc1)Nc1ccccc1NC(=O)c1ccccc1] |

TABLE 2-continued

| Compound No. | Structural formula |
|---|---|
| 65 | *[structure: N-phenyl-N'-(3-benzamidophenyl)urea]* |
| 66 | *[structure: N-phenyl-N'-(4-benzamidophenyl)urea]* |
| 67 | *[structure: N-phenyl-N'-(2-(4-methylbenzamido)phenyl)urea]* |
| 68 | *[structure: N-phenyl-N'-(4-(4-methylbenzamido)phenyl)urea]* |
| 69 | *[structure: N-phenyl-N'-(3-(4-methylbenzamido)phenyl)urea]* |
| 70 | *[structure: N-phenyl-N'-(2-(2-methylbenzamido)phenyl)urea]* |
| 71 | *[structure: N-phenyl-N'-(4-(2-methylbenzamido)phenyl)urea]* |

TABLE 2-continued

| Compound No. | Structural formula |
| --- | --- |
| 72 | |
| 73 | |
| 74 | |
| 75 | |
| 76 | |
| 77 | |

TABLE 2-continued

| Compound No. | Structural formula |
|---|---|
| 78 | 2,4-dimethylbenzamide linked to 3-(3-phenylureido)aniline |
| 79 | 4-chlorobenzamide linked to 2-(3-phenylureido)aniline |
| 80 | 4-chlorobenzamide linked to 4-(3-phenylureido)aniline |
| 81 | 4-chlorobenzamide linked to 3-(3-phenylureido)aniline |
| 82 | 2-chlorobenzamide linked to 2-(3-phenylureido)aniline |
| 83 | 2-chlorobenzamide linked to 4-(3-phenylureido)aniline |

TABLE 2-continued

| Compound No. | Structural formula |
|---|---|
| 84 | |
| 85 | |
| 86 | |
| 87 | |
| 88 | |
| 89 | |

TABLE 2-continued

| Compound No. | Structural formula |
| --- | --- |
| 90 | (4-carboxyphenyl)-C(=O)-NH-(3-substituted phenyl)-NH-C(=O)-NH-phenyl |
| 91 | (4-ethylphenyl)-C(=O)-NH-(2-substituted phenyl)-NH-C(=O)-NH-phenyl |
| 92 | (4-ethylphenyl)-C(=O)-NH-(4-substituted phenyl)-NH-C(=O)-NH-phenyl |
| 93 | (4-ethylphenyl)-C(=O)-NH-(3-substituted phenyl)-NH-C(=O)-NH-phenyl |
| 94 | (4-isopropylphenyl)-C(=O)-NH-(2-substituted phenyl)-NH-C(=O)-NH-phenyl |
| 95 | (4-isopropylphenyl)-C(=O)-NH-(4-substituted phenyl)-NH-C(=O)-NH-phenyl |

TABLE 2-continued

| Compound No. | Structural formula |
|---|---|
| 96 | 4-isopropyl-N-(3-(3-phenylureido)phenyl)benzamide |
| 97 | 4-methoxy-N-(2-(3-phenylureido)phenyl)benzamide |
| 98 | 4-methoxy-N-(4-(3-phenylureido)phenyl)benzamide |
| 99 | 4-methoxy-N-(3-(3-phenylureido)phenyl)benzamide |
| 100 | 4-(phenylthio)-N-(2-(3-phenylureido)phenyl)benzamide |
| 101 | 4-(phenylthio)-N-(4-(3-phenylureido)phenyl)benzamide |

TABLE 2-continued

| Compound No. | Structural formula |
| --- | --- |
| 102 | 4-(phenylthio)-N-(3-(3-phenylureido)phenyl)benzamide |
| 103 | 4-phenoxy-N-(2-(3-phenylureido)phenyl)benzamide |
| 104 | 4-phenoxy-N-(4-(3-phenylureido)phenyl)benzamide |
| 105 | 4-phenoxy-N-(3-(3-phenylureido)phenyl)benzamide |
| 106 | 4-vinyl-N-(2-(3-phenylureido)phenyl)benzamide |

TABLE 2-continued

| Compound No. | Structural formula |
| --- | --- |
| 107 | |
| 108 | |
| 109 | |
| 110 | |
| 111 | |
| 112 | |

TABLE 2-continued

| Compound No. | Structural formula |
|---|---|
| 113 | |
| 114 | |
| 115 | |

Examples of the alkyl group represented by $R^7$, $R^8$ or $R^9$ in the formula (3) include a linear, branched or cyclic alkyl group. Among them, a linear or branched alkyl group is preferred, and a linear alkyl group is more preferred. The range of the number of carbon atoms in each of these alkyl groups is usually C1 to C12, preferably C1 to C8, more preferably C1 to C6, further preferably C1 to C4. Specific examples thereof include: a linear alkyl group such as methyl, ethyl, n-propyl, n-butyl, n-pentyl, n-hexyl, n-octyl, n-nonyl, n-decyl, n-undecyl and n-dodecyl; a branched alkyl group such as isopropyl, isobutyl, sec-butyl, t-butyl, isopentyl, isohexyl and isooctyl; and a cyclic alkyl group such as cyclopropyl, cyclobutyl, cyclopentyl and cyclohexyl.

The range of the number of carbon atoms in the aryl group represented by $R^7$, $R^8$ or $R^9$ in the formula (3) is preferably C6 to C12. Specific examples thereof include a phenyl group and a naphthyl group. Among them, a phenyl group is particularly preferred.

In the present invention, each of $R^7$, $R^8$ and $R^9$ in the formula (3) is preferably a hydrogen atom, a methyl group or a phenyl group.

Examples of the substituent that may be added to the alkyl group or the aryl group of $R^7$, $R^8$ or $R^9$ in the formula (3) include, but are not limited to, an aryl group, a 5- or 6-membered heterocyclic group containing 1 to 3 atoms selected from a nitrogen atom, an oxygen atom and a sulfur atom as ring-constituting atoms, a 5- or 6-membered heterocyclylamino group containing 1 to 3 atoms selected from a nitrogen atom, an oxygen atom and a sulfur atom as ring-constituting atoms, a ring-fused heterocyclylamino group in which one benzene ring is fused with a 5- or 6-membered heterocyclic ring containing 1 to 3 atoms selected from a nitrogen atom, an oxygen atom and a sulfur atom as ring-constituting atoms, a linear, branched or cyclic alkoxy group, an aryloxy group, an arylcarbonylamino group, a linear, branched or cyclic alkylcarbonyloxy group, an arylcarbonyloxy group, a linear, branched or cyclic alkylcarbonyl group, an arylcarbonyl group, a carbamoyl group, a linear, branched or cyclic monoalkylcarbamoyl group, a linear, branched or cyclic dialkylcarbamoyl group, a monoarylcarbamoyl group, a diarylcarbamoyl group, a linear, branched or cyclic alkoxycarbonyl group, an aryloxycarbonyl group, a linear, branched or cyclic alkylsulfonylamino group, an arylsulfonylamino group, a sulfamoyl group, a linear, branched or cyclic monoalkylsulfamoyl group, a linear, branched or cyclic dialkylsulfamoyl group, a monoarylsulfamoyl group, a diarylsulfamoyl group, a linear, branched or cyclic alkylsulfonyl group, an arylsulfonyl group, a linear, branched or cyclic alkylthio group, an arylthio group, an ureido group, a linear, branched or cyclic monoalkylureido group, a linear, branched or cyclic dialkylureido group, a monoarylureido group, a diarylureido group, a linear, branched or cyclic alkoxycarbonylamino group, an aryloxycarbonylamino group, a linear, branched or cyclic monoalkylamino group, a linear, branched or cyclic dialkylamino group, an arylamino group, a mercapto group which means a group represented by "—SH" in the present specification, a halogen atom, a hydroxy group, a cyano group, a nitro group, an amino group and a carboxy group.

Examples of the aryl group preferably include a C6-C12 aryl group. Specific examples thereof include phenyl, naphthyl and biphenyl.

The 5- or 6-membered heterocyclic group containing 1 to 3 atoms selected from a nitrogen atom, an oxygen atom and a sulfur atom as ring-constituting atoms preferably has an aromatic ring as its heterocyclic moiety. Specific examples thereof include: a 5-membered alicyclic heterocyclic group such as pyrrolidinyl, tetrahydrofuryl, tetrahydrothiophen-2-yl and tetrahydrothiophen-3-yl; a 6-membered alicyclic heterocyclic group such as piperidinyl, piperazinyl, dioxan-2-yl, morpholinyl and thiomorpholinyl; a 5-membered aromatic heterocyclic group such as pyrrole, pyrazole, imidazole, triazole, furyl, thiophen-2-yl, thiophen-3-yl, oxazole and thiazole; and a 6-membered aromatic heterocyclic group such as pyridine, pyrazine, pyridazine and triazine. The ring-constituting atom is preferably selected from a nitrogen atom and a sulfur atom.

The 5- or 6-membered heterocyclylamino group containing 1 to 3 atoms selected from a nitrogen atom, an oxygen atom and a sulfur atom as ring-constituting atoms preferably has an aromatic ring as its heterocyclic moiety. Specific examples thereof include: a 5-membered alicyclic heterocyclylamino group such as pyrrolidinylamino, tetrahydrofurylamino, tetrahydrothiophen-2-ylamino and tetrahydrothiophen-3-ylamino; a 6-membered alicyclic heterocyclylamino group such as piperidinylamino, piperazinylamino, dioxan-2-ylamino, morpholinylamino and thiomorpholinylamino; a 5-membered aromatic heterocyclylamino group such as pyrrolamino, pyrazolamino, imidazolamino, triazolamino, furylamino, thiophen-2-ylamino, thiophen-3-ylamino, oxazolamino and thiazolamino; and a 6-membered aromatic heterocyclylamino group such as pyridylamino, pyrazylamino, pyridazinylamino and triazinylamino. The ring-constituting atom is preferably selected from a nitrogen atom and a sulfur atom.

The ring-fused heterocyclylamino group in which one benzene ring is fused with a 5- or 6-membered heterocyclic ring containing 1 to 3 atoms selected from a nitrogen atom, an oxygen atom and a sulfur atom as ring-constituting atoms preferably has an aromatic ring as its heterocyclic moiety. Specific examples thereof include: a heterocyclylamino group having a 5-membered alicyclic heterocyclic ring as its heterocyclic moiety, such as phthalanylamino; a heterocyclylamino group having a 6-membered alicyclic heterocyclic ring as its heterocyclic moiety, such as benzopyranylamino; a heterocyclylamino group having a 5-membered aromatic heterocyclic ring as its heterocyclic moiety, such as benzopyrrolamino, benzopyrazolamino, benzimidazolamino, benzotriazolamino, benzofuranylamino, benzothiophen-2-ylamino, benzothiophen-3-ylamino, benzoxazolamino and benzothiazolamino; and a heterocyclylamino group having a 6-membered aromatic heterocyclic ring as its heterocyclic moiety, such as quinolinylamino, cinnolinylamino, phthalazinylamino, quinazolinylamino and quinoxalinylamino. The ring-constituting atom is preferably selected from a nitrogen atom and a sulfur atom.

Examples of the linear, branched or cyclic alkoxy group preferably include a C1-C10 alkoxy group. Specific examples thereof include: a linear alkoxy group such as methoxy, ethoxy, n-propoxy, n-butoxy, n-pentoxy, n-hexyloxy, n-heptoxy, n-octyloxy, n-nonyloxy and n-decyloxy; a branched alkoxy group such as isopropoxy, isobutoxy, sec-butoxy, t-butoxy, isoamyloxy, t-amyloxy, isohexyloxy, t-hexyloxy, isoheptoxy, t-heptoxy, isooctyloxy, t-octyloxy, 2-ethylhexyloxy, isononyloxy and isodecyloxy, preferably a C3-C10 branched alkoxy group; and a cyclic alkoxy group such as cyclopropoxy, cyclobutoxy, cyclopentoxy, cyclohexyloxy and cycloheptoxy, preferably a C3-C7 cyclic alkoxy group. Preferred examples thereof include a linear or branched alkoxy group.

Examples of the aryloxy group preferably include a C6-C12 aryloxy group. Specific examples thereof include phenoxy, naphthyloxy and biphenyloxy.

Examples of the linear, branched or cyclic alkylcarbonylamino group preferably include a C1-C10 alkylcarbonylamino group. Specific examples thereof include: a linear alkylcarbonylamino group such as methylcarbonylamino, ethylcarbonylamino, n-propylcarbonylamino, n-butylcarbonylamino, n-pentylcarbonylamino, n-hexylcarbonylamino, n-heptylcarbonylamino, n-octylcarbonylamino, n-nonylcarbonylamino, and n-decylcarbonylamino; a branched alkylcarbonylamino group such as isopropylcarbonylamino, isobutylcarbonylamino, sec-butylcarbonylamino, t-butylcarbonylamino, isoamylcarbonylamino, t-amylcarbonylamino, isohexylcarbonylamino, t-hexylcarbonylamino, isoheptylcarbonylamino, t-heptylcarbonylamino, isooctylcarbonylamino, t-octylcarbonylamino, 2-ethylhexylcarbonylamino, isononylcarbonylamino and isodecylcarbonylamino, preferably a C3-C10 branched alkylcarbonylamino group; and a cyclic alkylcarbonylamino group such as cyclopropylcarbonylamino, cyclobutylcarbonylamino, cyclopentylcarbonylamino, cyclohexylcarbonylamino and cycloheptylcarbonylamino, preferably a C3-C7 cyclic alkylcarbonylamino group. Preferred examples thereof include a linear or branched alkylcarbonylamino group, more preferably a linear alkylcarbonylamino group.

Examples of the arylcarbonylamino group preferably include a C6-C12 arylcarbonylamino group. Specific examples thereof include phenylcarbonylamino, naphthylcarbonylamino and biphenylcarbonylamino.

Examples of the linear, branched or cyclic alkylcarbonyloxy group preferably include a C1-C10 alkylcarbonyloxy group. Specific examples thereof include: a linear alkylcarbonyloxy group such as methylcarbonyloxy, ethylcarbonyloxy, n-propylcarbonyloxy, n-butylcarbonyloxy, n-pentylcarbonyloxy, n-hexylcarbonyloxy, n-heptylcarbonyloxy, n-octylcarbonyloxy, n-nonylcarbonyloxy and n-decylcarbonyloxy; a branched alkylcarbonyloxy group such as isopropylcarbonyloxy, isobutylcarbonyloxy, sec-butylcarbonyloxy, t-butylcarbonyloxy, isoamylcarbonyloxy, t-amylcarbonyloxy, isohexylcarbonyloxy, t-hexylcarbonyloxy, isoheptylcarbonyloxy, t-heptylcarbonyloxy, isooctylcarbonyloxy, t-octylcarbonyloxy, 2-ethylhexylcarbonyloxy, isononylcarbonyloxy and isodecylcarbonyloxy, preferably a C3-C10 branched alkylcarbonyloxy group; and a cyclic alkylcarbonyloxy group such as cyclopropylcarbonyloxy, cyclobutylcarbonyloxy, cyclopentylcarbonyloxy, cyclohexylcarbonyloxy and cycloheptylcarbonyloxy, preferably a C3-C7 cyclic alkylcarbonyloxy group. Among them, a linear or branched alkylcarbonyloxy group is preferred, and a linear alkylcarbonyloxy group is more preferred.

Examples of the arylcarbonyloxy group preferably include a C6-C12 arylcarbonyloxy group. Specific examples thereof include phenylcarbonyloxy, naphthylcarbonyloxy and biphenylcarbonyloxy.

Examples of the linear, branched or cyclic alkylcarbonyl group preferably include a C1-C10 alkylcarbonyl group. Specific examples thereof include: a linear alkylcarbonyl group such as methylcarbonyl, ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl and n-decylcarbonyl; a branched alkylcarbonyl group such as isopropylcarbonyl, isobutylcarbonyl, sec-butylcarbonyl, t-butylcarbonyl, isoamylcarbonyl, t-amylcarbonyl, isohexylcarbonyl, t-hexylcarbonyl, isoheptylcarbonyl, t-heptylcarbonyl, isooctylcarbonyl, t-octylcarbonyl, 2-ethylhexylcarbonyl, isononylcarbonyl and isodecylcarbonyl, preferably a C3-C10 branched alkylcarbonyl group; and a cyclic alkylcarbonyl group such as cyclopropylcarbonyl, cyclobutylcarbonyl, cyclopentylcarbonyl, cyclohexylcarbonyl and cycloheptylcarbonyl, preferably a C3-C7 cyclic alkylcarbonyl group. Among them, a linear or branched alkylcarbonyl group is preferred, and a linear alkylcarbonyl group is more preferred.

Examples of the arylcarbonyl group preferably include a C6-C12 arylcarbonyl group. Specific examples thereof include phenylcarbonyl (benzoyl), naphthylcarbonyl and biphenylcarbonyl.

Examples of the linear, branched or cyclic monoalkylcarbamoyl group preferably include a mono-C1-C10 alkylcarbamoyl group. Specific examples thereof include: a linear monoalkylcarbamoyl group such as methylcarbamoyl, ethylcarbamoyl, n-propylcarbamoyl, n-butylcarbamoyl, n-pentylcarbamoyl, n-hexylcarbamoyl, n-heptylcarbamoyl, n-octylcarbamoyl, n-nonylcarbamoyl and n-decylcarbamoyl; a branched monoalkylcarbamoyl group such as isopropylcarbamoyl, isobutylcarbamoyl, sec-butylcarbamoyl, t-butylcarbamoyl, isoamylcarbamoyl, t-amylcarbamoyl, isohexylcarbamoyl, t-hexylcarbamoyl, isoheptylcarbamoyl, t-heptylcarbamoyl, isooctylcarbamoyl, t-octylcarbamoyl, 2-ethylhexylcarbamoyl, isononylcarbamoyl and isodecylcarbamoyl, preferably a C3-C10 branched monoalkylcarbamoyl group; and a cyclic monoalkylcarbamoyl group such as cyclopropylcarbamoyl, cyclobutylcarbamoyl, cyclopentylcarbamoyl, cyclohexylcarbamoyl and cycloheptylcarbamoyl, preferably a C3-C7 cyclic monoalkylcarbamoyl group. Preferred examples thereof include a linear or branched monoalkylcarbamoyl group, more preferably a linear monoalkylcarbamoyl group.

Examples of the linear, branched or cyclic dialkylcarbamoyl group preferably include a di-C1-C10 alkylcarbamoyl group. Specific examples thereof include: a linear dialkylcarbamoyl group such as dimethylcarbamoyl, diethylcarbamoyl, di-n-propylcarbamoyl, di-n-butylcarbamoyl, di-n-pentylcarbamoyl, di-n-hexylcarbamoyl, di-n-heptylcarbamoyl, di-n-octylcarbamoyl, di-n-nonylcarbamoyl and di-n-decylcarbamoyl; a branched dialkylcarbamoyl group such as diisopropylcarbamoyl, diisobutylcarbamoyl, di-sec-butylcarbamoyl, di-t-butylcarbamoyl, diisoamylcarbamoyl, di-t-amylcarbamoyl, diisohexylcarbamoyl, di-t-hexylcarbamoyl, diisoheptylcarbamoyl, di-t-heptylcarbamoyl, diisooctylcarbamoyl, di-t-octylcarbamoyl, di-(2-ethylhexyl)carbamoyl, diisononylcarbamoyl and diisodecylcarbamoyl, preferably a carbamoyl group having two C3-C10 branched alkyl groups; and a cyclic dialkylcarbamoyl group such as dicyclopropylcarbamoyl, dicyclobutylcarbamoyl, dicyclopentylcarbamoyl, dicyclohexylcarbamoyl and dicycloheptylcarbamoyl, preferably a carbamoyl group having two C3-C7 cyclic alkyl groups. Preferred examples thereof include a linear or branched dialkylcarbamoyl group, more preferably a linear dialkylcarbamoyl group.

Examples of the monoarylcarbamoyl group preferably include a mono-C6-C12 arylcarbamoyl group. Specific examples thereof include phenylcarbamoyl, naphthylcarbamoyl and biphenylcarbamoyl.

Examples of the diarylcarbamoyl group preferably include a di-C6-C12 arylcarbamoyl group. Specific examples thereof include diphenylcarbamoyl, dinaphthylcarbamoyl and di(biphenyl)carbamoyl.

Examples of the linear, branched or cyclic alkoxycarbonyl group preferably include a C1-C10 alkoxycarbonyl group. Specific examples thereof include: a linear alkoxycarbonyl group such as methoxycarbonyl, ethoxycarbonyl, n-propoxycarbonyl, n-butoxycarbonyl, n-pentoxycarbonyl, n-hexyloxycarbonyl, n-heptoxycarbonyl, n-octyloxycarbonyl, n-nonyloxycarbonyl and n-decyloxycarbonyl; a branched alkoxycarbonyl group such as isopropoxycarbonyl, isobutoxycarbonyl, sec-butoxycarbonyl, t-butoxycarbonyl, isoamyloxycarbonyl, t-amyloxycarbonyl, isohexyloxycarbonyl, t-hexyloxycarbonyl, isoheptoxycarbonyl, t-heptoxycarbonyl, isooctyloxycarbonyl, t-octyloxycarbonyl, 2-ethylhexyloxycarbonyl, isononyloxycarbonyl and isodecyloxycarbonyl, preferably a C3-C10 branched alkoxycarbonyl group; and a cyclic alkoxycarbonyl group such as cyclopropoxycarbonyl, cyclobutoxycarbonyl, cyclopentoxycarbonyl, cyclohexyloxycarbonyl and cycloheptoxycarbonyl, preferably a C3-C7 cyclic alkoxycarbonyl group. Preferred examples thereof include a linear or branched alkoxycarbonyl group, more preferably a linear alkoxycarbonyl group.

Examples of the aryloxycarbonyl group preferably include a C6-C12 aryloxycarbonyl group. Specific examples thereof include phenoxycarbonyl, naphthyloxycarbonyl and biphenyloxycarbonyl.

Examples of the linear, branched or cyclic alkylsulfonylamino group preferably include a C1-C10 alkylsulfonylamino group. Specific examples thereof include: a linear alkylsulfonylamino group such as methylsulfonylamino, ethylsulfonylamino, n-propylsulfonylamino, n-butylsulfonylamino, n-pentylsulfonylamino, n-hexylsulfonylamino, n-heptylsulfonylamino, n-octylsulfonylamino, n-nonylsulfonylamino and n-decylsulfonylamino; a branched alkylsulfonylamino group such as isopropylsulfonylamino, isobutylsulfonylamino, sec-butylsulfonylamino, t-butylsulfonylamino, isoamylsulfonylamino, t-amylsulfonylamino, isohexylsulfonylamino, t-hexylsulfonylamino, isoheptylsulfonylamino, t-heptylsulfonylamino, isooctylsulfonylamino, t-octylsulfonylamino, 2-ethylhexylsulfonylamino, isononylsulfonylamino and isodecylsulfonylamino, preferably a C3-C10 branched alkylsulfonylamino group; and a cyclic alkylsulfonylamino group such as cyclopropylsulfonylamino, cyclobutylsulfonylamino, cyclopentylsulfonylamino, cyclohexylsulfonylamino and cycloheptylsulfonylamino, preferably a C3-C7 cyclic alkylsulfonylamino group. Preferred examples thereof include a linear or branched alkylsulfonylamino group, more preferably a linear alkylsulfonylamino group.

Examples of the arylsulfonylamino group preferably include a C6-C12 arylsulfonylamino group. Specific examples thereof include phenylsulfonylamino, toluenesulfonylamino, naphthylsulfonylamino and biphenylsulfonylamino.

Examples of the linear, branched or cyclic monoalkylsulfamoyl group preferably include a mono-C1-C10 alkylsulfamoyl group. Specific examples thereof include: a linear monoalkylsulfamoyl group such as methylsulfamoyl, ethylsulfamoyl, n-propylsulfamoyl, n-butylsulfamoyl, n-pentylsulfamoyl, n-hexylsulfamoyl, n-heptylsulfamoyl, n-octylsulfamoyl, n-nonylsulfamoyl and n-decylsulfamoyl; a branched monoalkylsulfamoyl group such as isopropylsulfamoyl, isobutylsulfamoyl, sec-butylsulfamoyl, t-butylsulfamoyl, isoamylsulfamoyl, t-amylsulfamoyl, isohexylsulfamoyl, t-hexylsulfamoyl, isoheptylsulfamoyl, t-heptylsulfamoyl, isooctylsulfamoyl, t-octylsulfamoyl, 2-ethylhexylsulfamoyl, isononylsulfamoyl and isodecylsulfamoyl, preferably a C3-C10 branched monoalkylsulfamoyl group; and a cyclic monoalkylsulfamoyl group such as cyclopropylsulfamoyl, cyclobutylsulfamoyl, cyclopentylsulfamoyl, cyclohexylsulfamoyl and cycloheptylsulfamoyl, preferably a C3-C7 cyclic monoalkylsulfamoyl group. Preferred examples thereof include a linear or branched monoalkylsulfamoyl group, more preferably a linear monoalkylsulfamoyl group.

Examples of the linear, branched or cyclic dialkylsulfamoyl group preferably include a di-C1-C10 alkylsulfamoyl group. Specific examples thereof include: a linear dialkylsulfamoyl group such as dimethylsulfamoyl, diethylsulfamoyl, di-n-propylsulfamoyl, di-n-butylsulfamoyl, di-n-pentylsulfamoyl, di-n-hexylsulfamoyl, di-n-heptylsulfamoyl, di-n-octylsulfamoyl, di-n-nonylsulfamoyl and di-n-decylsulfamoyl; a branched dialkylsulfamoyl group such as diisopropylsulfamoyl, diisobutylsulfamoyl, di-sec-butylsulfamoyl, di-t-butylsulfamoyl, diisoamylsulfamoyl, di-t-amylsulfamoyl, diisohexylsulfamoyl, di-t-hexylsulfamoyl, diisoheptylsulfamoyl, di-t-heptylsulfamoyl, diisooctylsulfamoyl, di-t-octylsulfamoyl, di-(2-ethylhexyl)sulfamoyl, diisononylsulfamoyl and diisodecylsulfamoyl, preferably a sulfamoyl group having two C3-C10 branched alkyl groups; and a cyclic dialkylsulfamoyl group such as dicyclopropylsulfamoyl, dicyclobutylsulfamoyl, dicyclopentylsulfamoyl, dicyclohexylsulfamoyl and dicycloheptylsulfamoyl, preferably a sulfamoyl group having two C3-C7 cyclic alkyl groups. Preferred examples thereof include a linear or branched dialkylsulfamoyl group, more preferably a linear dialkylsulfamoyl group.

Examples of the monoarylsulfamoyl group preferably include a mono-C6-C12 arylsulfamoyl group. Specific examples thereof include phenylsulfamoyl, naphthylsulfamoyl and biphenylsulfamoyl.

Examples of the diarylsulfamoyl group preferably include a di-C6-C12 arylsulfamoyl group. Specific examples thereof include diphenylsulfamoyl, dinaphthylsulfamoyl and di(biphenyl)sulfamoyl.

Examples of the linear, branched or cyclic alkylsulfonyl group preferably include a C1-C12 alkylsulfonyl group. Specific examples thereof include: a linear alkylsulfonyl group such as methylsulfonyl, ethylsulfonyl, n-propylsulfonyl, n-butylsulfonyl, n-pentylsulfonyl, n-hexylsulfonyl, n-heptylsulfonyl, n-octylsulfonyl, n-nonylsulfonyl, n-decylsulfonyl, n-undecylsulfonyl and n-dodecylsulfonyl; a branched alkylsulfonyl group such as isopropylsulfonyl, isobutylsulfonyl, sec-butylsulfonyl, t-butylsulfonyl, isoamylsulfonyl, t-amylsulfonyl, isohexylsulfonyl, t-hexylsulfonyl, isoheptylsulfonyl, t-heptylsulfonyl, isooctylsulfonyl, t-octylsulfonyl, 2-ethylhexylsulfonyl, isononylsulfonyl, isodecylsulfonyl, isoundecylsulfonyl, t-undecylsulfonyl, isododecylsulfonyl and t-dodecylsulfonyl, preferably a C3-C12 branched alkylsulfonyl group; and a cyclic alkylsulfonyl group such as cyclopropylsulfonyl, cyclobutylsulfonyl, cyclopentylsulfonyl, cyclohexylsulfonyl and cycloheptylsulfonyl, preferably a C3-C7 cyclic alkylsulfonyl group. Preferred examples thereof include a linear or branched alkylsulfonyl group, more preferably a linear alkylsulfonyl group.

Examples of the arylsulfonyl group include a C6-C12 arylsulfonyl group. Specific examples thereof include phenylsulfonyl, naphthylsulfonyl and biphenylsulfonyl.

Examples of the linear, branched or cyclic alkylthio group preferably include a C1-C10 alkylthio group. Specific examples thereof include: a linear alkylthio group such as methylthio, ethylthio, n-propylthio, n-butylthio, n-pentylthio, n-hexylthio, n-heptylthio, n-octylthio, n-nonylthio and n-decylthio; a branched alkylthio group such as isopropylthio, isobutylthio, sec-butylthio, t-butylthio, isoamylthio, t-amylthio, isohexylthio, t-hexylthio, isoheptylthio, t-heptylthio, isooctylthio, t-octylthio, 2-ethylhexylthio, isononylthio and isodecylthio, preferably a C3-C10 branched alkylthio group; and a cyclic alkylthio group such as cyclopropylthio, cyclobutylthio, cyclopentylthio, cyclohexylthio and cycloheptylthio, preferably a C3-C7 cyclic alkylthio group. Preferred examples thereof include a linear or branched alkylthio group, more preferably a linear alkylthio group.

Examples of the arylthio group preferably include a C6-C12 arylthio group. Specific examples thereof include phenylthio, naphthylthio and biphenylthio.

Examples of the linear, branched or cyclic monoalkylureido group preferably include a mono-C1-C10 alkylureido group. Specific examples thereof include: a linear monoalkylureido group such as methylureido, ethylureido, n-propylureido, n-butylureido, n-pentylureido, n-hexylureido, n-heptylureido, n-octylureido, n-nonylureido and n-decylureido; a branched monoalkylureido group such as isopropylureido, isobutylureido, sec-butylureido, t-butylureido, isoamylureido, t-amylureido, isohexylureido, t-hexylureido, isoheptylureido, t-heptylureido, isooctylureido, t-octylureido, 2-ethylhexylureido, isononylureido and isodecylureido, preferably a C3-C10 branched monoalkylureido group; and a cyclic monoalkylureido group such as cyclopropylureido, cyclobutylureido, cyclopentylureido, cyclohexylureido and cycloheptylureido, preferably a C3-C7 cyclic monoalkylureido group. Preferred examples thereof include a linear or branched monoalkylureido group, more preferably a linear monoalkylureido group.

Examples of the linear, branched or cyclic dialkylureido group preferably include a di-C1-C10 alkylureido group. Specific examples thereof include: a linear dialkylureido group such as dimethylureido, diethylureido, di-n-propylureido, di-n-butylureido, di-n-pentylureido, di-n-hexylureido, di-n-heptylureido, di-n-octylureido, di-n-nonylureido and di-n-decylureido; a branched dialkylureido group such as diisopropylureido, diisobutylureido, di-sec-butylureido, di-t-butylureido, diisoamylureido, di-t-amylureido, diisohexylureido, di-t-hexylureido, diisoheptylureido, di-t-heptylureido, diisooctylureido, di-t-octylureido, di-(2-ethylhexyl)ureido, diisononylureido and diisodecylureido, preferably an ureido group having two C3-C10 branched alkyl groups; and a cyclic dialkylureido group such as dicyclopropylureido, dicyclobutylureido, dicyclopentylureido, dicyclohexylureido and dicycloheptylureido, preferably an ureido group having two C3-C7 cyclic alkyl groups. Preferred examples thereof include a linear or branched dialkylureido group, more preferably a linear dialkylureido group.

Examples of the monoarylureido group preferably include a mono-C6-C12 arylureido group. Specific examples thereof include phenylureido, naphthylureido and biphenylureido.

Examples of the diarylureido group preferably include a di-C6-C12 arylureido group. Specific examples thereof include diphenylureido, dinaphthylureido and di(biphenyl)ureido.

Examples of the linear, branched or cyclic alkoxycarbonylamino group preferably include a C1-C10 alkoxycarbonylamino group. Specific examples thereof include: a linear alkoxycarbonylamino group such as methoxycarbonylamino, ethoxycarbonylamino, n-propoxycarbonylamino, n-butoxycarbonylamino, n-pentoxycarbonylamino, n-hexyloxycarbonylamino, n-heptoxycarbonylamino, n-octyloxycarbonylamino, n-nonyloxycarbonylamino and n-decyloxycarbonylamino; a branched alkoxycarbonylamino group such as isopropoxycarbonylamino, isobutoxycarbonylamino, sec-butoxycarbonylamino, t-butoxycarbonylamino, isoamyloxycarbonylamino, t-amyloxycarbonylamino, isohexyloxycarbonylamino, t-hexyloxycarbonylamino, isoheptoxycarbonylamino, t-heptoxycarbonylamino, isooctyloxycarbonylamino, t-octyloxycarbonylamino, 2-ethylhexyloxycarbonylamino, isononyloxycarbonylamino and isodecyloxycarbonylamino, preferably a C3-C10 branched alkoxycarbonylamino group; and a cyclic alkoxycarbonylamino group such as cyclopropoxycarbonylamino, cyclobutoxycarbonylamino, cyclopentoxycarbonylamino, cyclohexyloxycarbonylamino and cycloheptoxycarbonylamino, preferably a C3-C7 cyclic alkoxycarbonylamino group. Preferred examples thereof include a linear or branched alkoxycarbonylamino group, more preferably a linear alkoxycarbonylamino group.

Examples of the aryloxycarbonylamino group preferably include a C6-C12 aryloxycarbonylamino group. Specific examples thereof include phenylcarbonylamino, naphthylcarbonylamino and biphenylcarbonylamino.

Examples of the linear, branched or cyclic monoalkylamino group preferably include a mono-C1-C10 alkylamino group. Specific examples thereof include: a linear monoalkylamino group such as methylamino, ethylamino, n-propylamino, n-butylamino, n-pentylamino, n-hexylamino, n-heptylamino, n-octylamino, n-nonylamino and n-decylamino; a branched monoalkylamino group such as isopropylamino, isobutylamino, sec-butylamino, t-butylamino, isoamylamino, t-amylamino, isohexylamino, t-hexylamino, isoheptylamino, t-heptylamino, isooctylamino, t-octylamino, 2-ethylhexylamino, isononylamino and isodecylamino, preferably a C3-C10 branched monoalkylamino group; and a cyclic monoalkylamino group such as cyclopropylamino, cyclobutylamino, cyclopentylamino, cyclohexylamino and cycloheptylamino, preferably a C3-C7 cyclic monoalkylamino group. Preferred examples thereof include a linear or branched monoalkylamino group, more preferably a linear monoalkylamino group.

Examples of the linear, branched or cyclic dialkylamino group preferably include a di-C1-C10 alkylamino group. Specific examples thereof include: a linear dialkylamino group such as dimethylamino, diethylamino, di-n-propylamino, di-n-butylamino, di-n-pentylamino, di-n-hexylamino, di-n-heptylamino, di-n-octylamino, di-n-nonylamino and di-n-decylamino; a branched dialkylamino group such as diisopropylamino, diisobutylamino, di-sec-butylamino, di-t-butylamino, diisoamylamino, di-t-amylamino, diisohexylamino, di-t-hexylamino, diisoheptylamino, di-t-heptylamino, diisooctylamino, di-t-octylamino, di-(2-ethylhexyl)amino, diisononylamino and diisodecylamino, preferably an amino group having two C3-C10 branched alkyl groups; and a cyclic dialkylamino group such as dicyclopropylamino, dicyclobutylamino, dicyclopentylamino, dicyclohexylamino and dicycloheptylamino, preferably an amino group having two C3-C7 cyclic alkyl groups. Preferred examples thereof include a linear or branched dialkylamino group, more preferably a linear dialkylamino group.

Examples of the arylamino group preferably include a monoarylamino group and a diarylamino group. Examples of the monoarylamino group preferably include a mono-C6-C12 arylamino group. Specific examples thereof include phenylamino (anilino), naphthylamino and biphenylamino. Likewise, examples of the diarylamino group preferably include a di-C6-C12 arylamino group. Specific examples thereof include diphenylamino, dinaphthylamino and di(biphenyl)amino.

Examples of the halogen atom include a fluorine atom, a chlorine atom, a bromine atom and an iodine atom and preferably include a fluorine atom, a chlorine atom and a bromine atom.

These substituents on each of $R^7$, $R^8$ and $R^9$ may each be further substituted, and the substituent therefor may be one or two, preferably one, of the aforementioned groups. However, an unsubstituted alkyl group or aryl group is preferred.

In the formula (3), examples of the position of substitution with the substituent —NHCOCR$^7$═CR$^8$R$^9$ on the benzene ring include an ortho position, a meta position and a para position. An ortho position is preferred.

Specific examples of the compound represented by the formula (3) according to the present invention can include, but are not limited to, compounds described in Table 3 below.

TABLE 3

| Compound No. | Structural formula |
|---|---|
| 116 | |
| 117 | |

TABLE 3-continued

| Compound No. | Structural formula |
|---|---|
| 118 | (acrylamide-C6H4-NHC(O)NH-phenyl, para) |
| 119 | (ortho-phenylene with crotonamide and NHC(O)NH-phenyl) |
| 120 | (meta-phenylene with crotonamide and NHC(O)NH-phenyl) |
| 121 | (para-phenylene with crotonamide and NHC(O)NH-phenyl) |
| 122 | (ortho-phenylene with methacrylamide and NHC(O)NH-phenyl) |
| 123 | (meta-phenylene with methacrylamide and NHC(O)NH-phenyl) |
| 124 | (para-phenylene with methacrylamide and NHC(O)NH-phenyl) |

TABLE 3-continued

| Compound No. | Structural formula |
|---|---|
| 125 | (structure: 2-substituted phenyl with NH-C(=O)-C(CH₃)=CH-CH₃ and NH-C(=O)-NH-phenyl) |
| 126 | (structure: 1,3-substituted phenyl with NH-C(=O)-C(CH₃)=CH-CH₃ and NH-C(=O)-NH-phenyl) |
| 127 | (structure: 1,4-substituted phenyl with NH-C(=O)-C(CH₃)=CH-CH₃ and NH-C(=O)-NH-phenyl) |
| 128 | (structure: 1,2-substituted phenyl with NH-C(=O)-CH=CH-phenyl (cinnamoyl) and NH-C(=O)-NH-phenyl) |
| 129 | (structure: 1,3-substituted phenyl with NH-C(=O)-CH=CH-phenyl (cinnamoyl) and NH-C(=O)-NH-phenyl) |
| 130 | (structure: 1,4-substituted phenyl with NH-C(=O)-CH=CH-phenyl (cinnamoyl) and NH-C(=O)-NH-phenyl) |
| 131 | (structure: 1,2-substituted phenyl with NH-C(=O)-CH=CH-OEt and NH-C(=O)-NH-phenyl) |

TABLE 3-continued
| Compound No. | Structural formula |
|---|---|
| 132 | 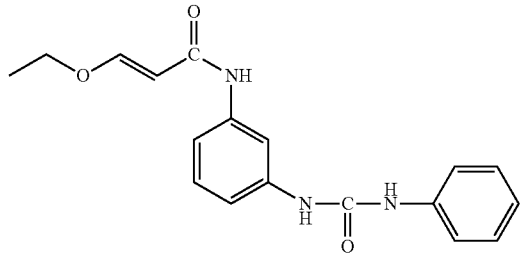 [SMILES: CCO/C=C/C(=O)Nc1cccc(NC(=O)Nc2ccccc2)c1] |
| 133 | 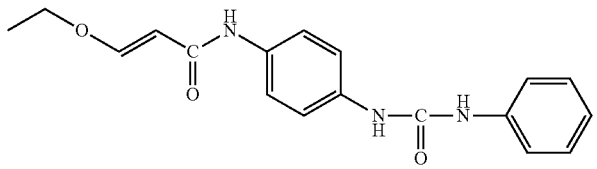 [SMILES: CCO/C=C/C(=O)Nc1ccc(NC(=O)Nc2ccccc2)cc1] |
| 134 | 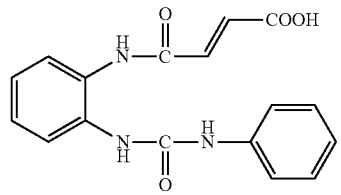 [SMILES: O=C(O)/C=C/C(=O)Nc1ccccc1NC(=O)Nc1ccccc1] |
| 135 | 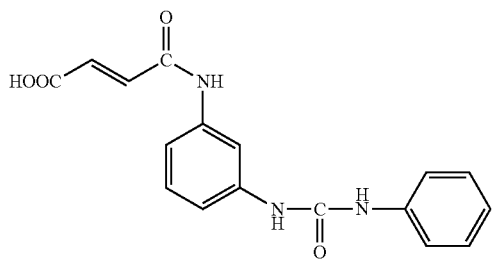 [SMILES: O=C(O)/C=C/C(=O)Nc1cccc(NC(=O)Nc2ccccc2)c1] |
| 136 | 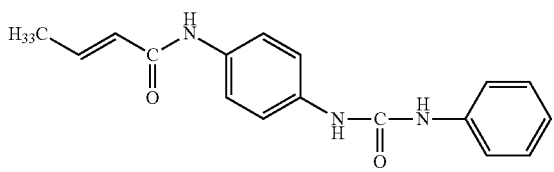 |
| 137 | 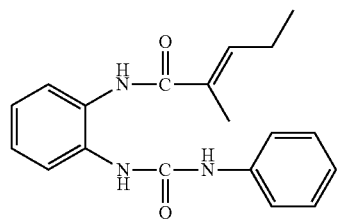 [SMILES: CC/C=C(\C)C(=O)Nc1ccccc1NC(=O)Nc1ccccc1] |
| 138 | 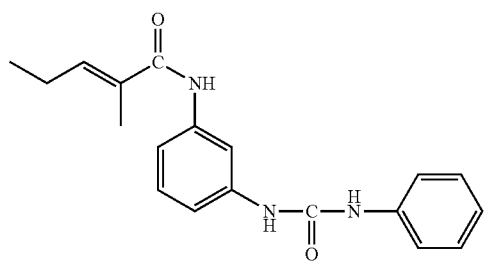 [SMILES: CC/C=C(\C)C(=O)Nc1cccc(NC(=O)Nc2ccccc2)c1] |

TABLE 3-continued

| Compound No. | Structural formula |
|---|---|
| 139 | |
| 140 | |
| 141 | |
| 142 | |

Next, a method for producing the compound of the present invention will be described.

The compound of the formula (1) can be produced according to, for example, a production process given below. However, the production method is not limited thereto.

[Production process 1]

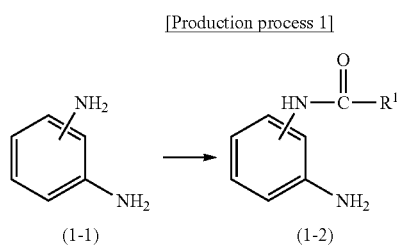

wherein $R^1$ is as defined above.

The compound of the formula (1-2) can be produced by reacting the compound of the formula (1-1) with an acid halide or an acid anhydride in the presence or absence of a base.

The solvent for use in this reaction is not particularly limited as long as the solvent has no influence on the reaction. Examples thereof include: amides such as N,N-dimethylformamide, N,N-dimethylacetamide and N-methylpyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; sulfones such as sulfolane; and sulfoxides such as dimethyl sulfoxide. These solvents may be used each alone or as a mixture.

Examples of the acid halide for use in this reaction include acetyl chloride, propinoyl chloride, isobutyryl chloride, propionyl chloride, pivaloyl chloride, butyryl chloride, 2,2-dimethylbutyryl chloride and isovaleryl chloride. The amount of the acid halide used is usually 0.1 to 50 mol, preferably 0.1 to 5 mol, with respect to 1 mol of the compound of the formula (1-1).

In general, the acid halide can be produced by reacting a compound represented by the following formula (1-3) with thionyl chloride or oxanyl chloride, etc.

wherein $R^1$ is as defined above.

Examples of the acid anhydride for use in this reaction include acetic anhydride. The amount of the acid anhydride used is 0.1 to 50 mol, preferably 1 to 5 mol, with respect to 1 mol of the compound of the formula (1-1).

Examples of the base that is used, if desired, in this reaction include: inorganic bases such as sodium bicarbonate, sodium carbonate, potassium carbonate and cesium carbonate; and organic bases such as triethylamine, pyridine and diisopropylethylamine. The amount of the base used can be usually 0.1 to 50 mol, preferably 1 to 5 mol, with respect to 1 mol of the compound of the formula (1-1).

The reaction temperature of this reaction is usually −78 to 100° C., preferably 0 to 80° C. The reaction can be carried out for 10 minutes to 24 hours.

[Production process 2]

![structure 1-2 and product 1]

(1-2)

(1)

wherein R¹ is as defined above.

The compound of the formula (1) can be produced by reacting the compound of the formula (1-2) with phenyl isocyanate in the presence or absence of a base. The solvent for use in this reaction is not particularly limited as long as the solvent has no influence on the reaction. Examples thereof include: amides such as N,N-dimethylformamide, N,N-dimethylacetamide and N-methylpyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; sulfones such as sulfolane; and sulfoxides such as dimethyl sulfoxide. These solvents may be used as a mixture.

The amount of the phenyl isocyanate used in this reaction is usually 0.1 to 50 mol, preferably 0.1 to 5 mol, with respect to 1 mol of the compound of the formula (1-2).

Examples of the base that is used, if desired, in this reaction include: inorganic bases such as sodium bicarbonate, sodium carbonate, potassium carbonate and cesium carbonate; and organic bases such as triethylamine and diisopropylethylamine. The amount of the base used is usually 0.1 to 50 mol, preferably 1 to 5 mol, with respect to 1 mol of the compound of the general formula (1-2).

The reaction temperature of this reaction is usually −78 to 100° C., preferably 0 to 80° C. The reaction can be carried out for 10 minutes to 24 hours.

The compound of the formula (2) can also be produced according to, for example, a production process given below. However, the production method is not limited thereto.

[Production Process 3]

First, the compound of the formula (2-2) can be produced by reacting the compound of the formula (2-1) with phenyl isocyanate in the presence or absence of a base.

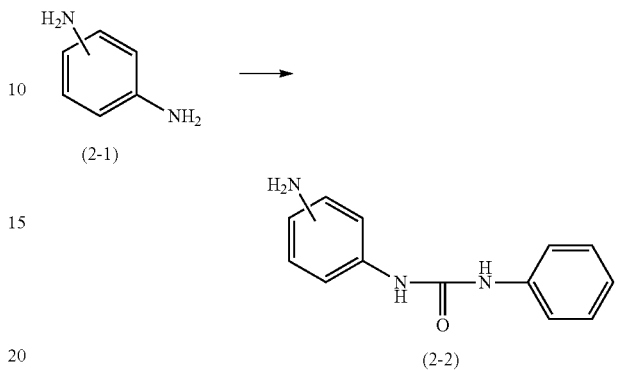

(2-1)

(2-2)

The solvent for use in this reaction is not particularly limited as long as the solvent has no influence on the reaction. Examples thereof include: amides such as N,N-dimethylformamide, N,N-dimethylacetamide and N-methylpyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; sulfones such as sulfolane; and sulfoxides such as dimethyl sulfoxide. These solvents may be used each alone or as a mixture.

The amount of the phenyl isocyanate used in this reaction can be usually 0.1 to 50 mol, preferably 0.1 to 5 mol, with respect to 1 mol of the compound of the formula (2-1).

Examples of the base that is used, if desired, in this reaction include: inorganic bases such as sodium bicarbonate, sodium carbonate, potassium carbonate and cesium carbonate; and organic bases such as triethylamine and diisopropylethylamine. The amount of the base used can be 0.1 to 50 mol, preferably 1 to 5 mol, with respect to 1 mol of the compound of the formula (2-1).

This reaction can usually be carried out at −78 to 100° C., preferably 0 to 80° C., for 10 minutes to 24 hours.

[Production Process 4]

The compound of the formula (2) can be produced by reacting the compound of the formula (2-2) with an acid halide in the presence or absence of a base.

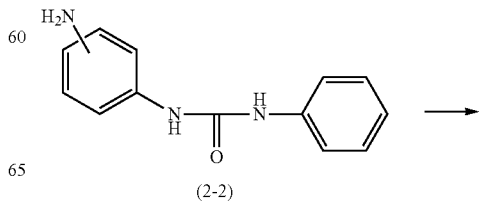

(2-2)

-continued

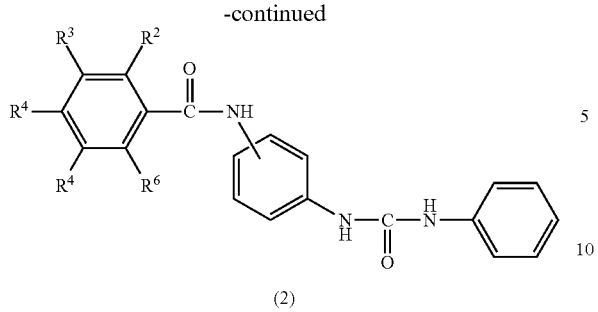

(2)

wherein $R^2$ to $R^6$ are as defined above.

The solvent for use in this reaction is not particularly limited as long as the solvent has no influence on the reaction. Examples thereof include: amides such as N,N-dimethylformamide, N,N-dimethylacetamide and N-methylpyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; sulfones such as sulfolane; and sulfoxides such as dimethyl sulfoxide. These solvents may be used each alone or as a mixture.

Examples of the acid halide for use in this reaction include benzoyl chloride, 4-methylbenzoyl chloride, 3-methylbenzoyl chloride, 2-methylbenzoyl chloride, 4-chlorobenzoyl chloride, 3,5-dimethylbenzoyl chloride and 3,5-dichlorobenzoyl chloride.

The acid halide can be produced by reacting a compound represented by the formula (2-3) with thionyl chloride or oxanyl chloride, etc.

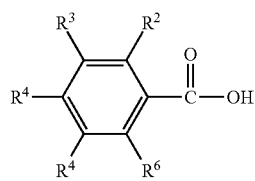

(2-3)

wherein $R^2$ to $R^6$ are as defined above.

The amount of the acid halide used can be 0.1 to 50 mol, preferably 1 to 5 mol, with respect to 1 mol of the compound of the formula (2-2).

Examples of the acid anhydride for use in this reaction include acetic anhydride. The amount of the acid anhydride used can be 0.1 to 50 mol, preferably 1 to 5 mol, with respect to 1 mol of the compound of the formula (2-2).

Examples of the base that is used, if desired, in this reaction include: inorganic bases such as sodium bicarbonate, sodium carbonate, potassium carbonate and cesium carbonate; and organic bases such as triethylamine, pyridine and diisopropylethylamine. The amount of the base used can be 0.1- to 50-fold mol, preferably 1- to 5-fold mol, with respect to 1 mol of the compound of the formula (2-2).

This reaction can usually be carried out at −78 to 100° C., preferably 0 to 80° C., for 10 minutes to 24 hours.

Next, the compound of the formula (3) can be produced according to, for example, a production process given below. However, the production method is not limited thereto.

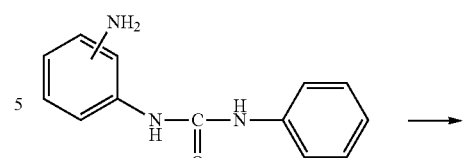

(2-2)

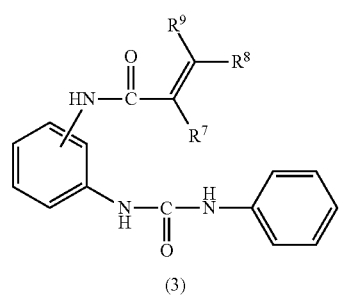

(3)

wherein $R^7$, $R^8$ and $R^9$ are as defined above.

The compound of the formula (3) can be produced by reacting the compound of the formula (3-2) with an acid halide in the presence or absence of a base. The solvent for use in this reaction is not particularly limited as long as the solvent has no influence on the reaction. Examples thereof include: amides such as N,N-dimethylformamide, N,N-dimethylacetamide and N-methylpyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; sulfones such as sulfolane; and sulfoxides such as dimethyl sulfoxide. These solvents may be used each alone or as a mixture.

Examples of the acid halide for use in this reaction include acetyl chloride, propinoyl chloride, isobutyryl chloride, propionyl chloride, pivaloyl chloride, butyryl chloride, 2,2-dimethylbutyryl chloride and isovaleryl chloride. The amount of the acid halide used is 0.1 to 50 mol, preferably 1 to 5 mol, with respect to 1 mol of the compound of the formula (3-2).

In general, the acid halide can be produced by reacting a compound represented by the following formula (3-3) with thionyl chloride or oxanyl chloride, etc.

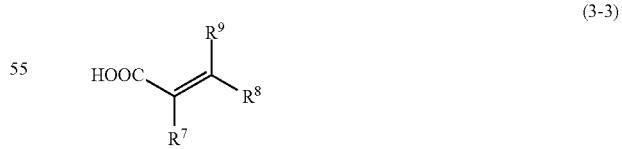

(3-3)

wherein $R^7$, $R^8$ and $R^9$ are as defined in the formula (3).

Examples of the base that is used, if desired, in this reaction include: inorganic bases such as sodium bicarbonate, sodium carbonate, potassium carbonate and cesium carbonate; and organic bases such as triethylamine, pyridine and diisopropylethylamine. The amount of the base used can be 0.1 to 50 mol, preferably 1 to 5 mol, with respect to 1 mol of the compound of the formula (3-2).

The reaction temperature of this reaction is usually −78 to 100° C., preferably 0 to 80° C. The reaction can be carried out for 10 minutes to 24 hours.

The thermosenstive recording material according to the present invention usually contains a color-forming compound, in addition to at least one compound represented by any of the formulas (1) to (3). Also, the thermosensitive recording material according to the present invention may optionally contain a sensitizer and/or a preservation stabilizer and may further contain a binder, a filler and/or other additives.

The thermosenstive recording material according to one embodiment of the present invention usually contains 1 to 50% by weight, preferably 5 to 30% by weight, of the color-forming compound. The compound represented by any of the formulas (1) to (3) is usually contained at 1 to 70% by weight, preferably 10 to 50% by weight. The sensitizer is usually contained at 1 to 80% by weight. The preservation stabilizer is usually contained at 0 to 30% by weight. The binder is usually contained at 1 to 90% by weight. The filler is usually contained at 0 to 80% by weight. Other additives, such as a lubricant, a surfactant, an antifoaming agent and a UV absorber, are contained at their respective arbitrary ratios, for example, 0 to 30% by weight, respectively. % by weight of each component is the weight ratio of the component to the thermal color recording material.

In a preferred embodiment, the compound represented by any of the formulas (1) to (3) in the composition described above is contained in the range of preferably 0.5 to 20, more preferably 1 to 5 with respect to 1 of the color-forming compound in terms of a weight ratio. The thermosensitive recording material of the present invention may contain an additional color developing compound known in the art and may contain additives other than those described above.

The color-forming compound used in the present invention is not particularly limited as long as the color-forming compound is generally used in a pressure-sensitive recording paper or a thermosenstive recording paper. Examples of the color-forming compound used include fluoran compounds, triarylmethane compounds, spiro compounds, diphenylmethane compounds, thiazine compounds, lactam compounds and fluorene compounds. Fluoran compounds are preferred.

Specific examples of the fluoran compounds include 3-diethylamino-6-methyl-7-anilinofluoran, 3-dibutylamino-6-methyl-7-anilinofluoran, 3-(N-methyl-N-cyclohexylamino)-6-methyl-7-anilinofluoran, 3-(N-ethyl-N-isopentylamino)-6-methyl-7-anilinofluoran, 3-(N-ethyl-N-isobutylamino)-6-methyl-7-anilinofluoran, 3-[N-ethyl-N-(3-ethoxypropyl)amino]-6-methyl-7-anilinofluoran, 3-(N-ethyl-N-hexylamino)-6-methyl-7-anilinofluoran, 3-dipentylamino-6-methyl-7-anilinofluoran, 3-(N-methyl-N-propylamino)-6-methyl-7-anilinofluoran, 3-(N-ethyl-N-tetrahydrofurylamino)-6-methyl-7-anilinofluoran, 3-diethylamino-6-methyl-7-(p-chloroanilino)fluoran, 3-diethylamino-6-methyl-7-(p-fluoroanilino)fluoran, 3-[N-ethyl-N-(p-tolyl)amino]-6-methyl-7-anilinofluoran, 3-diethylamino-6-methyl-7-(p-toluidino)fluoran, 3-diethylamino-7-(o-chloroanilino)fluoran, 3-dibutylamino-7-(o-chloroanilino)fluoran, 3-diethylamino-7-(o-fluoroanilino)fluoran, 3-dibutylamino-7-(o-fluoroanilino)fluoran, 3-diethylamino-7-(3,4-dichloroanilino)fluoran, 3-pyrrolidino-6-methyl-7-anilinofluoran, 3-diethylamino-6-chloro-7-ethoxyethylaminofluoran, 3-diethylamino-6-chloro-7-anilinofluoran, 3-diethylamino-7-chlorofluoran, 3-diethylamino-7-methylfluoran, 3-diethylamino-7-octylfluoran and 3-[N-ethyl-N-(p-tolyl)amino]-6-methyl-7-phenethylfluoran. 3-Dibutylamino-6-methyl-7-anilinofluoran is preferred.

Specific examples of the triarylmethane compounds include 3,3-bis(p-dimethylaminophenyl)-6-dimethylaminophthalide (also called crystal violet lactone or CVL), 3,3-bis(p-dimethylaminophenyl)phthalide, 3-(p-dimethylaminophenyl)-3-(1,2-dimethylaminoindol-3-yl)phthalide, 3-(p-dimethylaminophenyl)-3-(2-methylindol-3-yl)phthalide, 3-(p-dimethylaminophenyl)-3-(2-phenylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-5-dimethylaminophthalide, 3,3-(2-phenylindol-3-yl)-5-dimethylaminophthalide and 3-p-dimethylaminophenyl-3-(1-methylpyrrol-2-yl)-6-dimethylaminophthalide.

Specific examples of the spiro compounds include 3-methylspirodinaphthopyran, 3-ethylspirodinaphthopyran, 3,3'-dichlorospirodinaphthopyran, 3-benzylspirodinaphthopyran, 3-propylspirobenzopyran, 3-methylnaphtho-(3-methoxybenzo)spiropyran and 1,3,3-trimethyl-6-nitro-8'-methoxyspiro(indoline-2,2'-benzopyran). Specific examples of the diphenylmethane compounds include N-halophenylleucoauramine, 4,4-bis-dimethylaminophenylbenzhydryl benzyl ether and N-2,4,5-trichlorophenylleucoauramine. Specific examples of the thiazine compounds include benzoyl leucomethylene blue and p-nitrobenzoyl leucomethylene blue. Specific examples of the lactam compounds include rhodamine B anilinolactam and rhodamine B-p-chloroanilinolactam. Specific examples of the fluorene compounds include 3,6-bis(dimethylamino)fluorenespiro(9,3')-6'-dimethylaminophthalide, 3,6-bis(dimethylamino)fluorenespiro(9,3')-6'-pyrrolidinophthalide and 3-dimethylamino-6-diethylaminofluorenespiro(9,3')-6'-pyrrolidinophthalide.

These color-forming compounds are used each alone or as a mixture.

The color developing compound that may be used in combination is not particularly limited and can be a color developing compound generally used in a pressure-sensitive recording paper or a thermosenstive recording paper. Examples thereof include: phenolic compounds such as α-naphthol, β-naphthol, p-octylphenol, 4-t-octylphenol, p-t-butylphenol, p-phenylphenol, 1,1-bis(p-hydroxyphenyl)propane, 2,2-bis(p-hydroxyphenyl)propane (also called bisphenol A or BPA), 2,2-bis(p-hydroxyphenyl)butane, 1,1-bis(p-hydroxyphenyl)cyclohexane, 4,4'-thiobisphenol, 4,4'-cyclohexylidene diphenol, 2,2'-bis(2,5-dibromo-4-hydroxyphenyl)propane, 4,4'-isopropylidenebis(2-t-butylphenol), 2,2'-methylenebis(4-chlorophenol), 4,4'-dihydroxydiphenylsulfone, 4-hydroxy-4'-methoxydiphenylsulfone, 2,4'-dihydroxydiphenylsulfone, 4-hydroxy-4'-isopropoxydiphenylsulfone, 4-hydroxy-4'-ethoxydiphenylsulfone, 4-hydroxy-4'-butoxydiphenylsulfone, 4-hydroxy-4'-benzyloxydiphenylsulfone, methyl bis(4-hydroxyphenyl)acetate, butyl bis(4-hydroxyphenyl)butyl acetate, benzyl bis(4-hydroxyphenyl)acetate and 2,4-dihydroxy-2'-methoxybenzanilide; and aromatic carboxylic acid derivatives, aromatic carboxylic acids or polyvalent metal salts thereof, such as benzyl p-hydroxybenzoate, ethyl p-hydroxybenzoate, dibenzyl 4-hydroxyphthalate, dimethyl 4-hydroxyphthalate, ethyl 5-hydroxyisophthalate, 3,5-di-t-butylsalicylic acid and 3,5-di-α-methylbenzylsalicylic acid.

Specific examples of the sensitizer (thermally fusible compound) used in the present invention include waxes (e.g., animal- or plant-derived waxes and synthetic waxes), higher fatty acids, higher fatty acid amides, higher fatty acid anilides, naphthalene derivatives, aromatic ethers, aromatic carboxylic acid derivatives, aromatic sulfonic acid ester derivatives, carbonic acid or oxalic acid diester derivatives, biphenyl derivatives, terphenyl derivatives and sulfone derivatives. Among them, a sensitizer that is solid at ordinary temperature and has a melting point of 60° C. or higher is preferably used.

Specific examples of the waxes include Japan tallow, carnauba wax, shellac, paraffin, montan wax, paraffin oxide, polyethylene wax and polyethylene oxide. Specific examples of the higher fatty acids include stearic acid and behenic acid. Specific examples of the higher fatty acid amides include stearic acid amide, oleic acid amide, N-methyl stearic acid amide, erucic acid amide, methylol behenic acid amide, methylenebisstearic acid amide and ethylenebisstearic acid amide. Specific examples of the higher fatty acid anilides include stearic acid anilide and linoleic acid anilide. Specific examples of the naphthalene derivatives include 1-benzyloxynaphthalene, 2-benzyloxynaphthalene and 1-hydroxynaphthoic acid phenyl ester. Specific examples of the aromatic ethers include 1,2-diphenoxyethane, 1,4-diphenoxybutane, 1,2-bis(3-methylphenoxy)ethane, 1,2-bis(4-methoxyphenoxy)ethane, 1,2-bis(3,4-dimethylphenyl)ethane, 1-phenoxy-2-(4-chlorophenoxy)ethane, 1-phenoxy-2-(4-methoxyphenoxy)ethane and 1,2-diphenoxymethylbenzene. Specific examples of the aromatic carboxylic acid derivatives include p-hydroxybenzoic acid benzyl ester, p-benzyloxybenzoic acid benzyl ester and terephthalic acid dibenzyl ester. Specific examples of the aromatic sulfonic acid ester derivatives include p-toluenesulfonic acid phenyl ester, phenyl mesitylenesulfonate and 4-methylphenyl mesitylenesulfonate. Specific examples of the carbonic acid or oxalic acid diester derivatives include diphenyl carbonate, oxalic acid dibenzyl ester, oxalic acid di(4-chlorobenzyl) ester and oxalic acid di(4-methylbenzyl) esters. Specific examples of the biphenyl derivatives include p-benzylbiphenyl and p-allyloxybiphenyl. Specific examples of the terphenyl derivatives include m-terphenyl. Specific examples of the sulfone derivatives include diphenylsulfone.

Specific examples of the preservation stabilizer used in the present invention include: hindered phenol compounds such as 2,2'-methylenebis(4-methyl-6-tert-butylphenol), 2,2'-methylenebis(4-ethyl-6-tert-butylphenol), 2,2'-ethylidenebis(4,6-di-tert-butylphenol), 4,4'-thiobis(2-methyl-6-tert-butylphenol), 4,4'-butylidenebis(6-tert-butyl-m-cresol), 1-[α-methyl-α-(4'-hydroxyphenyl)ethyl]-4-[α',α'-bis(4'-hydroxyphenyl)ethyl]benzene, 1,1,3-tris(2-methyl-4-hydroxy-5-cyclohexylphenyl)butane, 1,1,3-tris(2-methyl-4-hydroxy-5-tert-butylphenyl)butane, tris(2,6-dimethyl-4-tertiary butyl-3-hydroxybenzyl)isocyanurate, 4,4'-thiobis(3-methylphenol), 4,4'-dihydroxy-3,3',5,5'-tetrabromodiphenylsulfone, 4,4'-dihydroxy-3,3',5,5'-tetramethyldiphenylsulfone, 2,2-bis(4-hydroxy-3,5-dibromophenyl)propane, 2,2-bis(4-hydroxy-3,5-dichlorophenyl)propane and 2,2-bis(4-hydroxy-3,5-dimethylphenyl)propane; epoxy compounds such as 1,4-diglycidyloxybenzene, 4,4'-diglycidyloxydiphenylsulfone, 4-benzyloxy-4'-(2-methylglycidyloxy)diphenylsulfone, diglycidyl terephthalate, cresol novolac-type epoxy resins, phenol novolac-type epoxy resins and bisphenol A-type epoxy resins; and N,N'-di-2-naphthyl-p-phenylenediamine, sodium or polyvalent metal salts of 2,2'-methylenebis(4,6-di-tert-butylphenyl)phosphate, and bis(4-ethyleniminocarbonylaminophenyl)methane, UU (developer manufactured by Chemipro Kasei Kaisha, Ltd.) and a diphenylsulfone-cross-linked compound represented by the following formula (15), and mixtures thereof.

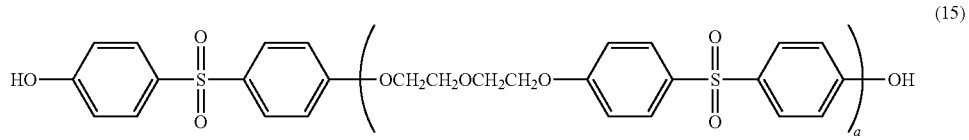

(15)

wherein a is an integer of 0 to 6.

Specific examples of the binder used in the present invention include: water-soluble binders such as methylcellulose, methoxycellulose, hydroxyethylcellulose, carboxymethylcellulose, sodium carboxymethylcellulose, cellulose, polyvinyl alcohol (PVA), carboxyl group-modified polyvinyl alcohol, sulfonic acid group-modified polyvinyl alcohol, silyl group-modified polyvinyl alcohol, polyvinylpyrrolidone, polyacrylamide, polyacrylic acid, starch and its derivatives, casein, gelatin, water-soluble isoprene rubber, alkali salts of styrene/maleic anhydride copolymers and alkali salts of iso (or diiso) butylene/maleic anhydride copolymers; and hydrophobic polymer emulsions such as (meth)acrylic acid ester copolymers, styrene/(meth)acrylic acid ester copolymers, polyurethane, polyester polyurethane, polyether polyurethane, polyvinyl acetate, ethylene/vinyl acetate copolymers, polyvinyl chloride, vinyl chloride/vinyl acetate copolymers, polyvinylidene chloride, polystyrene, styrene/butadiene (SB) copolymers, carboxylated styrene/butadiene (SB) copolymers, styrene/butadiene/acrylic acid copolymers, acrylonitrile/butadiene (NB) copolymers, carboxylated acrylonitrile/butadiene (NB) copolymers and composite particles of colloidal silica and a (meth)acrylic resin.

Specific examples of the filler used in the present invention include calcium carbonate, magnesium carbonate, magnesium oxide, silica, white carbon, talc, clay, alumina, magnesium hydroxide, aluminum hydroxide, aluminum oxide, barium sulfate, polystyrene resins and urea-formalin resins.

In the present invention, various additives other than those described above can be further used. Examples thereof include: higher fatty acid metal salts such as zinc stearate and calcium stearate, for the purpose of preventing the abrasion of thermal heads or preventing sticking; UV absorbers such as phenol derivatives, benzophenone compounds and benzotriazole compounds, for conferring an antioxidative or antiaging effect; and various surfactants and antifoaming agents.

Next, examples of methods for preparing the thermosenstive recording material of the present invention and a thermosenstive recording paper using the thermosenstive recording material will be described. However, the method for producing the thermosenstive recording material of the present invention is not limited to the examples below. For example, the color-forming compound and compound represented by any of the formulas (1) to (3) are separately pulverized and dispersed, together with a binder or other optional additives, etc., in a dispersing machine such as a ball mill, an attritor or a sand mill to prepare respective dispersions (usually, water is used as a medium for wet pulverization or dispersion). Then, the dispersions are mixed to prepare a thermosenstive recording material coating liquid, which can then be applied at usually 1 to 20 g/m² in terms of a dry weight, using a bar coater, a blade coater or the like, onto a support such as paper (regular paper, high-quality paper, coat paper or the like can be used), a plastic sheet or synthetic paper and dried to prepare a thermosenstive recording paper having a layer made of the thermosenstive recording material of the present invention.

If necessary, an intermediate layer may be disposed between the thermosenstive recording layer and the support, or an overcoat layer (protective layer) may be disposed on the thermosenstive recording layer. The intermediate layer or the overcoat layer (protective layer) is disposed, for example, by pulverizing and dispersing a component as needed, together with the binder or other optional additives, in the same way as in the preparation of the thermosenstive recording material coating liquid to prepare a coating liquid for the intermediate layer or a coating liquid for the overcoat layer (protective layer), which is then applied at usually approximately 0.1 to 10 g/m² in terms of a dry weight and dried.

EXAMPLES

Hereinafter, the present invention will be described further specifically with reference to Examples. However, the present invention is not intended to be limited by Examples below by any means. In Examples, the unit "part" means part by weight, and the unit "%" in the description of solutions means % by weight.

1. Synthesis of Compound of Formula (1), and Preparation and Evaluation of Thermosenstive Recording Material Containing the Compound

[Example 1] Synthesis of Compound 4 of Table 1

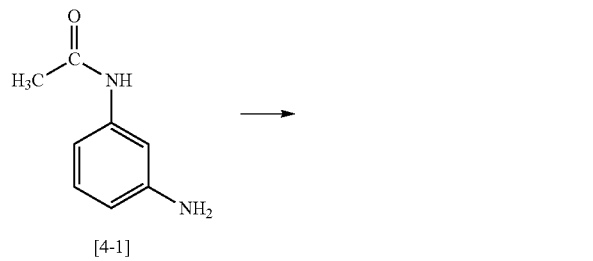

To a solution of 3.0 parts of 3'-aminoacetanilide of the formula [4-1] (manufactured by Tokyo Chemical Industry Co., Ltd.) in 100 parts of chloroform, 2.6 parts of phenyl isocyanate (manufactured by Tokyo Chemical Industry Co., Ltd.) were added dropwise at room temperature, and the mixture was stirred at the same temperature as above for 30 minutes. After the completion of the reaction, deposits were filtered off, and the cake was washed with ethyl acetate and water in this order and dried in vacuum to obtain compound 4 described in Table 1 as a white solid (4.2 parts).

$^1$H NMR (DMSO-d$_6$): δ9.92 (1H), 8.78 (1H), 8.64 (1H), 7.76 (1H), 7.45 (2H), 7.27 (2H), 7.17 (3H), 6.96 (1H), 2.03 (3H)

[Example 2] Synthesis of Compound 1 of Table 1

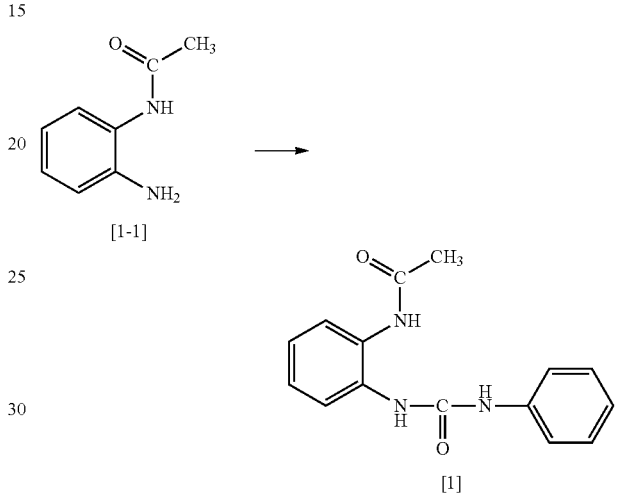

To 964 parts of chloroform, 22.2 parts of 2'-aminoacetanilide of the formula [1-1] (manufactured by Tokyo Chemical Industry Co., Ltd.) were added, and the mixture was stirred. Subsequently, 19.3 parts of phenyl isocyanate (manufactured by Tokyo Chemical Industry Co., Ltd.) were added dropwise thereto at room temperature, and the mixture was stirred at the same temperature as above for 2 hours. After the completion of the reaction, deposits were filtered off, and the cake was washed with ethyl acetate and water in this order and dried in vacuum to obtain compound 1 described in Table 1 as a white solid (33.5 parts).

MS(ESI): [M−H]$^-$: cal.: 268.1, found: 268.1.

[Example 3] Synthesis of Compound 57 of Table 1

[Step 3-1]

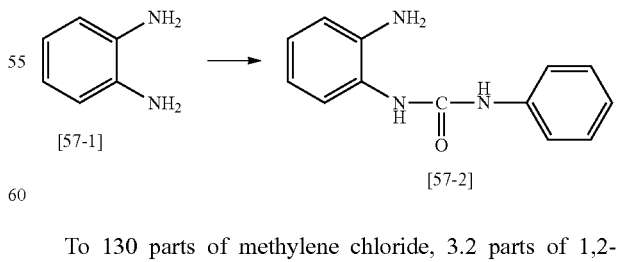

To 130 parts of methylene chloride, 3.2 parts of 1,2-diaminobenzene (manufactured by Tokyo Chemical Industry Co., Ltd.) [57-1] were added, and the mixture was stirred. Subsequently, 3.6 parts of phenyl isocyanate (manufactured by Tokyo Chemical Industry Co., Ltd.) were added dropwise thereto at room temperature, and the mixture was stirred at the same temperature as above for 2 hours. Then, deposits were filtered off, and the cake was washed with hexane and water in this order and dried in vacuum to obtain a compound of the formula [57-2] as a pale yellow solid (2.8 parts).

MS(ESI): [M−H]⁻: cal.: 226.1, found: 226.1.

[Step 3-2]

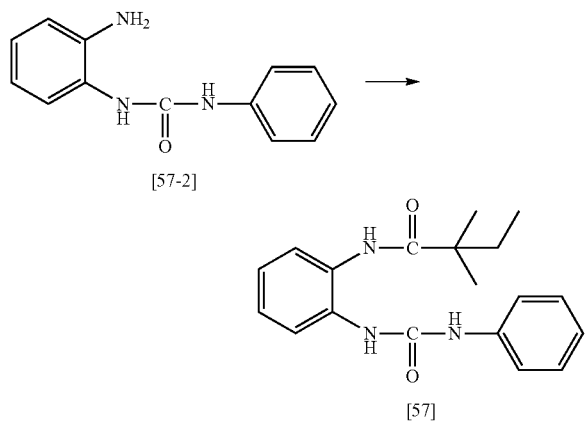

To 117 parts of methylene chloride, 2.0 parts of the compound of the formula [57-2] were added, and the mixture was stirred. Subsequently, 1.23 parts of 2,2-dimethylbutyl chloride were added dropwise thereto at room temperature, then 0.92 parts of triethylamine were added dropwise thereto at the same temperature as above, and the mixture was stirred for 1 hour. After the completion of the reaction, the reaction mixture was washed with a 10% aqueous HCl solution and a saturated aqueous solution of sodium bicarbonate in this order, and methylene chloride was distilled off under reduced pressure. The residue was washed with ethyl acetate and water in this order and dried in vacuum to obtain compound 57 described in Table 1-9 as a white solid (2.3 parts).

MS(ESI): [M−H]⁻: cal.: 324.1, found: 324.1.

[Example 4] Synthesis of Compound 63 of Table 1

[Step 4-1]

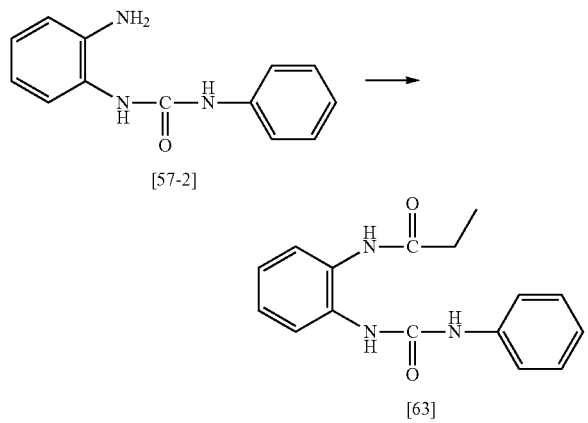

To 175 parts of methylene chloride, 3.0 parts of the compound of the formula [57-2] were added, and the mixture was stirred. Subsequently, 1.3 parts of propionyl chloride (manufactured by Tokyo Chemical Industry Co., Ltd.) were added dropwise thereto at room temperature, then 1.4 parts of triethylamine (Wako Pure Chemical Industries, Ltd.) were added dropwise thereto at the same temperature as above, and the mixture was stirred for 1 hour. After the completion of the reaction, the reaction mixture was washed with a 10% aqueous HCl solution and a saturated aqueous solution of sodium bicarbonate in this order, and methylene chloride was distilled off under reduced pressure. The residue was washed with ethyl acetate and water in this order and dried in vacuum to obtain compound 63 described in Table 1 as a white solid (2.5 parts).

MS(ESI): [M−H]⁻: cal.: 282.1, found: 282.1.

[Example 5] Synthesis of Compound 3 of Table 1

[Step 5-1]

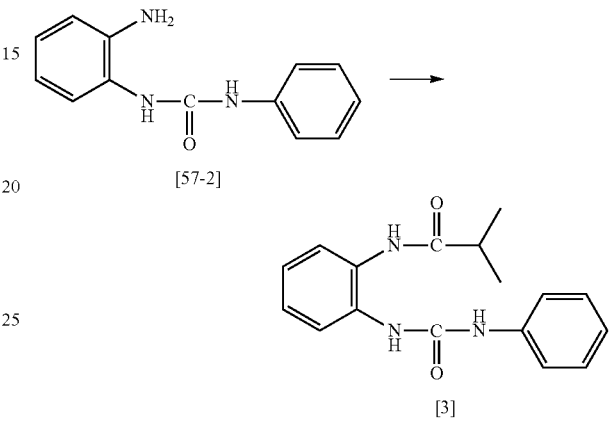

To 175 parts of methylene chloride, 3.0 parts of the compound of the formula [57-2] were added, and the mixture was stirred. Subsequently, 1.5 parts of isobutyryl chloride (manufactured by Tokyo Chemical Industry Co., Ltd.) were added dropwise thereto at room temperature, then 1.4 parts of triethylamine (Wako Pure Chemical Industries, Ltd.) were added dropwise thereto at the same temperature as above, and the mixture was stirred for 1 hour. After the completion of the reaction, the reaction mixture was washed with a 10% aqueous HCl solution and a saturated aqueous solution of sodium bicarbonate in this order, and methylene chloride was distilled off under reduced pressure. The residue was washed with ethyl acetate and water in this order and dried in vacuum to obtain compound 3 described in Table 1 as a white solid (2.6 parts).

MS(ESI): [M−H]⁻: cal.: 296.1, found: 296.1.

[Example 6] Preparation of Thermosenstive Recording Material and Thermosenstive Recording Paper Compound 4 of Table 1 obtained in Example 1 was pulverized and dispersed for 1 hour according to the composition given below using Multi Beads Shocker (model: PV1001(S)) manufactured by Yasui Kikai Corp. to prepare liquid [A].

| Liquid [A]: | |
| --- | --- |
| Compound 4 described in Table 1 | 15 parts |
| 25% aqueous PVA solution | 20 parts |
| Water | 65 parts |

A mixture having the composition given below was pulverized and dispersed into an average particle size of 1 μm or smaller using a sand grinder to prepare dispersion [B] of the color-forming compound.

| Liquid [B]: | |
|---|---|
| 3-Dibutylamino-6-methyl-7-anilinofluoran | 35 parts |
| 15% aqueous PVA solution | 40 parts |
| Water | 25 parts |

Subsequently, the liquids thus obtained and the agents given below were mixed according to the composition given below to prepare a thermosenstive recording material coating liquid, which was then applied at 5 g/m² in terms of a dry weight onto high-quality paper having a basis weight of 50 g/m² and dried to prepare a thermosenstive recording paper having the thermosenstive recording layer of the present invention.

| Liquid [A] | 40.0 parts |
|---|---|
| Liquid [B] | 8.6 parts |
| 67% aqueous calcium carbonate dispersion | 9.0 parts |
| 48% modified styrene-butadiene copolymer latex | 6.3 parts |
| Water | 36.1 parts |

(Formation of Protective Layer)

Next, a protective layer coating liquid having the composition given below was applied at 2 g/m² in terms of a dry weight onto the thermosenstive recording layer and dried to prepare a thermosenstive recording paper having the thermosenstive recording layer covered with the protective layer.

| 40% styrene/acrylic acid ester copolymer emulsion | 115 parts |
|---|---|
| 5% aqueous bentonite dispersion | 17 parts |
| 45% aqueous styrene-acryl copolymer emulsion | 44 parts |
| 39% aqueous zinc stearate dispersion | 103 parts |
| 67% aqueous calcium carbonate dispersion | 15 parts |

Example 7

A thermosenstive recording paper having the thermosenstive recording layer of the present invention was obtained in the same way as in Example 6 except that compound 1 of Table 1 was used instead of compound 4 of Table 1.

Example 8

A thermosenstive recording paper having the thermosenstive recording layer of the present invention was obtained in the same way as in Example 6 except that compound 57 of Table 1 was used instead of compound 4 of Table 1.

Example 9

A thermosenstive recording paper having the thermosenstive recording layer of the present invention was obtained in the same way as in Example 6 except that compound 63 of Table 1 was used instead of compound 4 of Table 1.

Example 10

A thermosenstive recording paper having the thermosenstive recording layer of the present invention was obtained in the same way as in Example 6 except that compound 3 of Table 1 was used instead of compound 4 of Table 1.

Comparative Example 1

A mixture having the composition given below was pulverized and dispersed into an average particle size of 1 µm or smaller using a sand grinder to prepare liquid [C]. A thermosenstive recording paper for comparison was obtained in the same way as in Example 6 except that: liquid [A] in the composition of the thermosenstive recording layer coating liquid described in Example 1 was changed to liquid [C]; and the composition in the preparation of the thermosenstive recording material was changed to 24.0 parts of liquid [C] and 52.1 parts of water.

| Liquid [C]: | |
|---|---|
| Bisphenol S | 25 parts |
| 25% aqueous PVA solution | 20 parts |
| Water | 55 parts |

[Water Resistance Test]

The thermosenstive recording paper having the thermosenstive recording layer, obtained in each of Examples 6, 7, 8, 9 and 10 and Comparative Example 1 was printed at a pulse width of 1.2 msec using a thermal printer (TH-M2/PP) manufactured by Okura Engineering Co., Ltd., and then dipped in water at 25° C. for 24 hours. The Macbeth reflection density of a colored part in the thermosenstive recording paper was measured before and after the test using a colorimeter (trade name "SpectroEye") manufactured by GretagMacbeth. All of the color measurements were performed under conditions involving illuminant C as a light source, ANSI A as a density reference and a view angle of 2 degrees. The results are shown in Table 4 below. A higher residual rate means better water resistance. The residual rate was determined according to the following expression (I):

Residual rate (%)=(Macbeth reflection density of the colored part in the sample after the test)/(Macbeth reflection density of the colored part in the sample before the test)×100     (I)

TABLE 4

| | Example 6 | Example 7 | Example 8 | Example 9 | Example 10 | Comparative Example 1 |
|---|---|---|---|---|---|---|
| Residual rate (%) | 81 | 78 | 90 | 87 | 91 | 67 |

As is evident from Table 4, the thermosenstive recording papers obtained in Examples 6 to 10 using the compound of the present invention had a higher residual rate than that of the thermosenstive recording paper obtained in Comparative Example 1 using bisphenol S as a color developing compound as described in Patent Literature 2, demonstrating that the present invention is superior in the water resistance of recorded images to conventional techniques.

[Heat Resistance of Background]

The thermosenstive recording paper obtained in each of Examples 6, 7, 8, 9 and 10 and Comparative Example 1 was kept at 90° C. for 1 hour using an air-blowing constant-temperature thermostat (trade name "DKN402") manufactured by Yamato Scientific Co., Ltd. The ISO whiteness of the background was measured before and after the test using a colorimeter (trade name "SpectroEye") manufactured by GretagMacbeth. All of the color measurements were performed under conditions involving illuminant C as a light source, ANSI A as a density reference and a view angle of 2 degrees. The results are shown in Table 5 below. A smaller amount of change in ISO whiteness between before and after the test means better heat resistance of the background.

TABLE 5

| Measurement of background part | Example 6 | Example 7 | Example 8 | Example 9 | Example 10 | Comparative Example 1 |
|---|---|---|---|---|---|---|
| Before test | 72.7 | 74.7 | 73.7 | 73.5 | 76.2 | 67.0 |
| After test | 69.3 | 72.8 | 71.3 | 68.6 | 71.8 | 45.0 |
| Amount of change | 3.4 | 1.9 | 2.4 | 4.9 | 4.4 | 22.0 |

As is evident from Table 5, the thermosenstive recording papers obtained in Examples 6 to 10 using the compound of the present invention exhibited a small amount of change in ISO whiteness between before and after the heat resistance test. Therefore, their backgrounds exhibited very high stability against heat, as compared with the thermosenstive recording paper obtained in Comparative Example 1 using bisphenol S as described in Patent Literature 2.

2. Synthesis of Compound of Formula (2), and Preparation and Evaluation of Thermosenstive Recording Material Containing the Compound

[Example 11] Synthesis of Compound 64 of Table 2

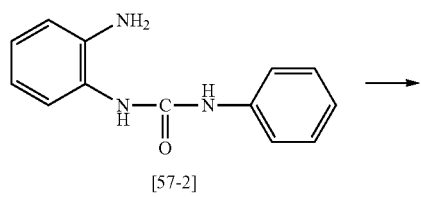

[57-2]

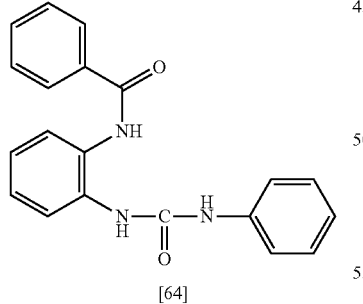

[64]

To 130 parts of methylene chloride, 2.0 parts of N-(2-aminophenyl)-N"-phenylurea of the formula [57-2], 1.2 parts of benzoyl chloride (manufactured by Tokyo Chemical Industry Co., Ltd.) and 0.9 parts of triethylamine (manufactured by Tokyo Chemical Industry Co., Ltd.) were added, and the mixture was stirred at room temperature for 4 hours. The deposited solid was collected by filtration, washed with hexane and water and then dried in vacuum to obtain compound 64 of Table 2 as a white solid (1.8 parts).

MS(ESI): [M−H]$^+$: cal.: 332.1, found: 332.3.

[Example 12] Synthesis of Compound 67 of Table 2

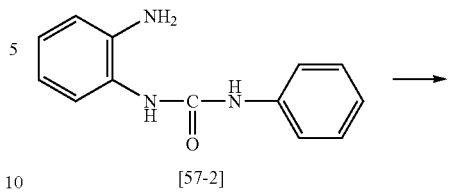

[57-2]

-continued

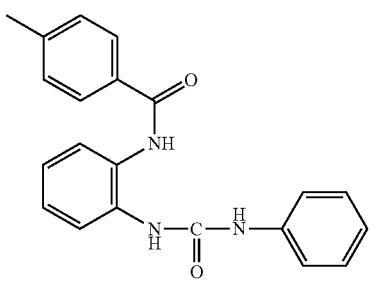

[67]

Compound 67 of Table 2 was obtained as a white solid (1.9 parts) in the same way as in Example 11 except that 1.3 parts of 4-methylbenzoyl chloride were added instead of benzoyl chloride of Example 11.

MS(ESI): [M−H]$^-$: cal.: 344.1, found: 344.1.

[Example 13] Synthesis of Compound 70 of Table 2

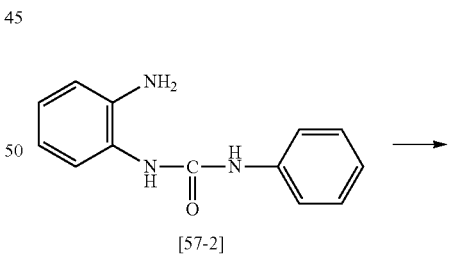

[57-2]

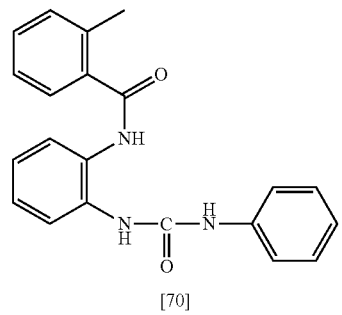

[70]

Compound 70 of Table 2 was obtained as a white solid (1.9 parts) in the same way as in Example 11 except that 1.3 parts of 2-methylbenzoyl chloride were added instead of benzoyl chloride of Example 11.

MS(ESI): [M−H]⁻: cal.: 344.1, found: 344.1.

[Example 14] Synthesis of Compound 73 of Table 2

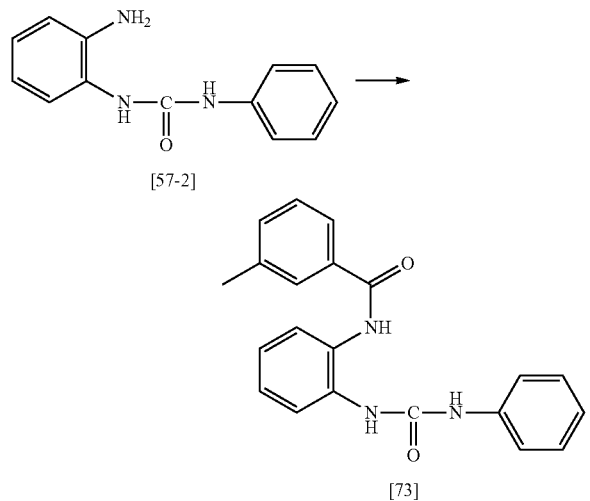

Compound 73 of Table 2 was obtained as a white solid (1.4 parts) in the same way as in Example 11 except that 1.3 parts of 3-methylbenzoyl chloride were added instead of benzoyl chloride of Example 11.

MS(ESI): [M−H]⁻: cal.: 344.1, found: 344.1.

[Example 15] Synthesis of Compound 97 of Table 2

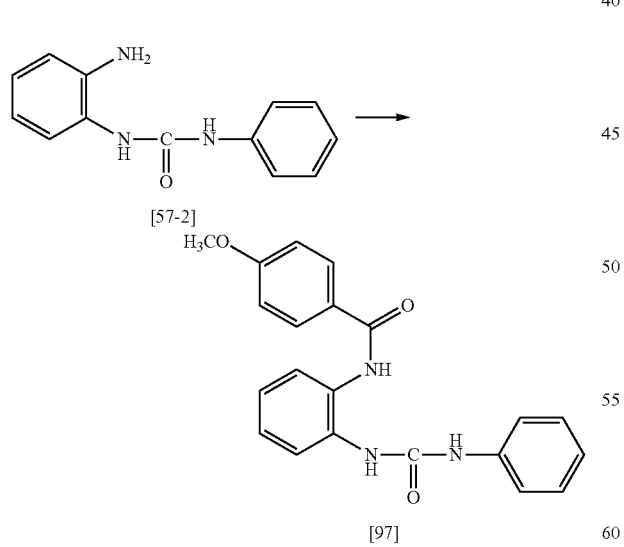

Compound 97 of Table 2 was obtained as a white solid (1.8 parts) in the same way as in Example 11 except that 1.5 parts of 4-methoxybenzoyl chloride were added instead of benzoyl chloride of Example 11.

MS(ESI): [M−H]⁻: cal.: 360.1, found: 360.1.

[Example 16] Synthesis of Compound 114 of Table 2

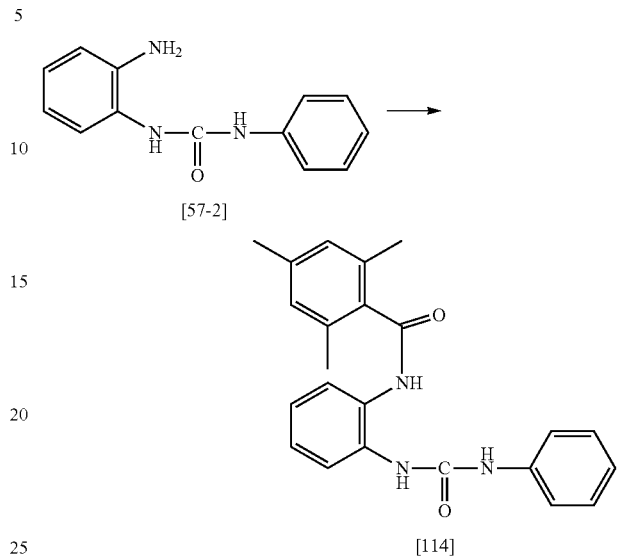

Compound 114 of Table 2 was obtained as a white solid (1.4 parts) in the same way as in Example 11 except that 1.8 parts of 2,4,6-trimethylbenzoyl chloride were added instead of benzoyl chloride of Example 11.

MS(ESI): [M−H]⁻: cal.: 372.1, found: 372.1.

[Example 17] Synthesis of Compound 115 of Table 2

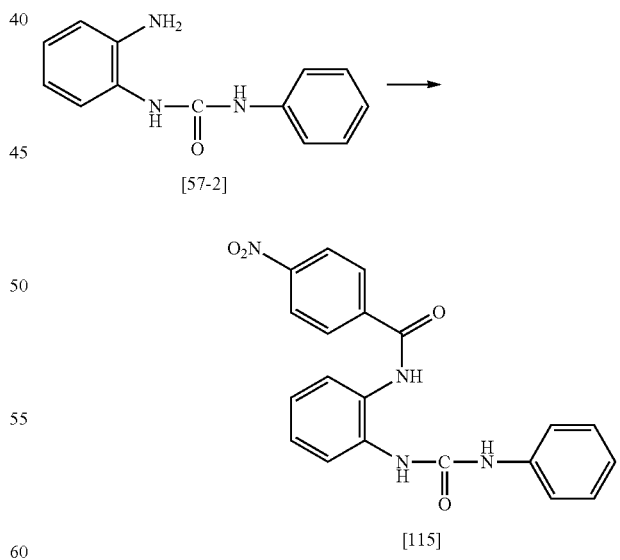

Compound 115 of Table 2 was obtained as a white solid (1.9 parts) in the same way as in Example 11 except that 1.8 parts of 4-nitrobenzoyl chloride were added instead of benzoyl chloride of Example 11.

MS(ESI): [M−H]⁻: cal.: 375.1, found: 375.1.

[Example 18] Preparation of Thermosenstive Recording Material and Thermosenstive Recording Paper The compound obtained in Example 11 was pulverized and dispersed for 1 hour using Multi Beads Shocker (model: PV1001(S)) manufactured by Yasui Kikai Corp. to prepare liquid [A]:

| Liquid [A]: | |
| --- | --- |
| Compound 64 of Table 2 | 15 parts |
| 25% aqueous PVA solution | 20 parts |
| Water | 65 parts |

A mixture having the composition given below was pulverized and dispersed into an average particle size of 1 µm or smaller using a sand grinder to prepare liquid [B].

| Liquid [B]: | |
| --- | --- |
| 3-Dibutylamino-6-methyl-7-anilinofluoran | 35 parts |
| 15% aqueous PVA solution | 40 parts |
| Water | 25 parts |

Subsequently, the liquids thus obtained and the agents given below were mixed at the ratio given below to prepare a thermosenstive recording material coating liquid, which was then applied at 5 g/m² in terms of a dry weight onto high-quality paper having a basis weight of 50 g/m² and dried to prepare a thermosenstive recording paper having the thermosenstive recording layer of the present invention.

| | |
| --- | --- |
| Liquid [A] | 40.0 parts |
| Liquid [B] | 8.6 parts |
| 67% aqueous calcium carbonate dispersion | 9.0 parts |
| 48% modified styrene-butadiene copolymer latex | 6.3 parts |
| Water | 36.1 parts |

(Formation of Protective Layer)

Next, a protective layer coating liquid having the composition given below was applied at 2 g/m² in terms of a dry weight onto the thermosenstive recording layer and dried to prepare a thermosenstive recording paper having the thermosenstive recording layer covered with the protective layer.

| | |
| --- | --- |
| 40% styrene/acrylic acid ester copolymer emulsion | 115 parts |
| 5% aqueous bentonite dispersion | 17 parts |
| 45% aqueous styrene-acryl copolymer emulsion | 44 parts |
| 39% aqueous zinc stearate dispersion | 103 parts |
| 67% aqueous calcium carbonate dispersion | 15 parts |

Example 19

A thermosenstive recording paper having the thermosenstive recording layer of the present invention was obtained in the same way as in Example 18 except that compound 67 of Table 2 was used instead of compound 64 of Table 2.

Example 20

A thermosenstive recording paper having the thermosenstive recording layer of the present invention was obtained in the same way as in Example 18 except that compound 70 of Table 2 was used instead of compound 64 of Table 2.

Example 21

A thermosenstive recording paper having the thermosenstive recording layer of the present invention was obtained in the same way as in Example 18 except that compound 73 of Table 2 was used instead of compound 64 of Table 2.

Example 22

A thermosenstive recording paper having the thermosenstive recording layer of the present invention was obtained in the same way as in Example 18 except that compound 97 of Table 2 was used instead of compound 64 of Table 2.

Example 23

A thermosenstive recording paper having the thermosenstive recording layer of the present invention was obtained in the same way as in Example 18 except that compound 114 of Table 2 was used instead of compound 64 of Table 2.

Example 24

A thermosenstive recording paper having the thermosenstive recording layer of the present invention was obtained in the same way as in Example 18 except that compound 115 of Table 2 was used instead of compound 64 of Table 2.

Comparative Example 2

A mixture having the composition given below was pulverized and dispersed into an average particle size of 1 µm or smaller using a sand grinder to prepare liquid [C]. A thermosenstive recording paper having a thermosenstive recording layer for comparison was obtained in the same way as in Example 18 except that liquid [A] in the composition of the thermal color-forming layer coating liquid described in Example 18 was changed to liquid [C].

| Liquid [C]: | |
| --- | --- |
| Bisphenol S | 25 parts |
| 25% aqueous PVA solution | 20 parts |
| Water | 55 parts |

[Water Resistance Test]

The thermosenstive recording paper obtained in each of Examples 18 to 24 and Comparative Example 2 was printed at a pulse width of 1.2 msec using a thermal printer (TH-M2/PP) manufactured by Okura Engineering Co., Ltd., and then dipped in water at 25° C. for 24 hours. The Macbeth reflection density of a colored part in the thermosenstive recording paper was measured before and after the test using a colorimeter (trade name "SpectroEye") manufactured by GretagMacbeth. All of the color measurements were performed under conditions involving illuminant C as a light source, ANSI A as a density reference and a view angle of 2 degrees. The results are shown in Table 6. A higher residual rate means better water resistance. The residual rate was determined according to the following expression:

Residual rate (%)=(Macbeth reflection density of the colored part in the sample after the test)/(Macbeth reflection density of the colored part in the sample before the test)×100

TABLE 6

| | Residual rate (%) | Chromogenic compound |
|---|---|---|
| Example 18 | 82 | Compound No. 64 of Table 2 |
| Example 19 | 79 | Compound No. 67 of Table 2 |
| Example 20 | 85 | Compound No. 70 of Table 2 |
| Comparative Example 2 | 67 | Bisphenol S |
| Example 21 | 83 | Compound No. 73 of Table 2 |
| Example 22 | 83 | Compound No. 97 of Table 2 |
| Example 23 | 95 | Compound No. 114 of Table 2 |
| Example 24 | 92 | Compound No. 115 of Table 2 |

As is evident from Table 6, the thermosenstive recording material of the present invention had a higher residual rate of the colored part than that of the thermosenstive recording material of Comparative Example 2 using bisphenol S as described in Patent Literature 2, demonstrating excellent water resistance of recorded images.

[Heat Resistance of Background]

Each obtained thermosenstive recording paper was kept at 90° C. for 1 hour using an air-blowing constant-temperature thermostat (trade name "DKN402") manufactured by Yamato Scientific Co., Ltd. The ISO whiteness of the background was measured before and after the test using a colorimeter (trade name "SpectroEye") manufactured by GretagMacbeth. All of the color measurements were performed under conditions involving illuminant C as a light source, ANSI A as a density reference and a view angle of 2 degrees. The results are shown in Table 7. A smaller amount of change in ISO whiteness between before and after the test means better heat resistance of the background.

TABLE 7

| | Background part | | | |
|---|---|---|---|---|
| | Before test | After test | Amount of change | Chromogenic compound |
| Example 18 | 76.3 | 76.3 | 0 | Compound No. 64 of Table 2 |
| Example 19 | 74.9 | 74.9 | 0 | Compound No. 67 of Table 2 |
| Example 20 | 75.3 | 76.3 | 1.0 | Compound No. 70 of Table 2 |
| Comparative Example 2 | 67.0 | 45.0 | 22.0 | Bisphenol S |
| Example 21 | 72.5 | 70.4 | 2.1 | Compound No. 73 of Table 2 |
| Example 22 | 74.8 | 72.4 | 2.4 | Compound No. 97 of Table 2 |
| Example 23 | 74.7 | 71.7 | 3.0 | Compound No. 114 of Table 2 |
| Example 24 | 74.4 | 71.8 | 2.6 | Compound No. 115 of Table 2 |

As is evident from Table 7, the thermosenstive recording material of the present invention exhibited a small amount of change in ISO whiteness between before and after the heat resistance test. Therefore, their backgrounds exhibited very high stability against heat, as compared with the thermosenstive recording material of Comparative Example 2 using bisphenol S as a color developing compound as described in Patent Literature 2.

3. Synthesis of Compound of Formula (3), and Preparation and Evaluation of Thermosenstive Recording Material Containing the Compound

[Example 25] Synthesis of Compound 116 of Table 3

[Step 1]

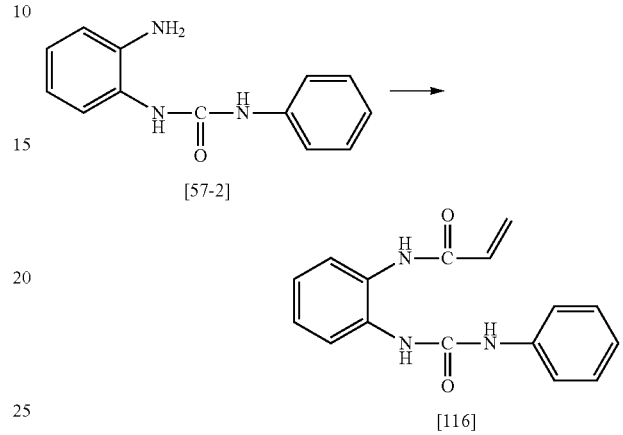

To 175 parts of methylene chloride, 3.0 parts of the compound of the formula [57-2] were added, and the mixture was stirred. Subsequently, 1.2 parts of acryloyl chloride (Wako Pure Chemical Industries, Ltd.) were added dropwise thereto at room temperature, then 1.38 parts of triethylamine (manufactured by Tokyo Chemical Industry Co., Ltd.) were added dropwise thereto at the same temperature as above, and the mixture was stirred for 1 hour. After the completion of the reaction, deposits were filtered off, and n-hexane was added to the filtrate. The resulting yellow oil substance was isolated, and ethyl acetate was added thereto. The resulting white solid was filtered off, washed with water, and dried in vacuum to obtain compound 116 as a white solid (1.6 parts).

MS(ESI): [M+Na]$^+$: cal.: 304.1, found: 304.1.

[Example 26] Synthesis of Compound 128 of Table 3

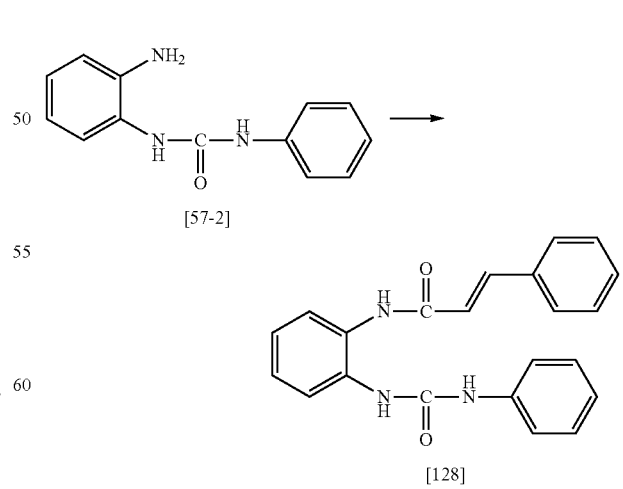

To 146 parts of methylene chloride, 5.0 parts of the compound of the formula [57-2] were added, and the mixture was stirred. Subsequently, 3.9 parts of cinnamoyl chloride (manufactured by Tokyo Chemical Industry Co., Ltd.) were added dropwise thereto at room temperature, then 2.3 parts of triethylamine (manufactured by Tokyo Chemical Industry Co., Ltd.) were added dropwise thereto at the same temperature as above, and the mixture was stirred for 1 hour. After the completion of the reaction, deposits were filtered off, and n-hexane was added to the filtrate. The resulting yellow oil substance was isolated, and ethyl acetate was added thereto. The resulting white solid was filtered off, washed with water, and dried in vacuum to obtain compound 128 as a white solid (1.5 parts).

MS(ESI): [M−H]⁻: cal.: 356.1, found: 356.1.

[Example 27] Synthesis of Compound 119 of Table 3

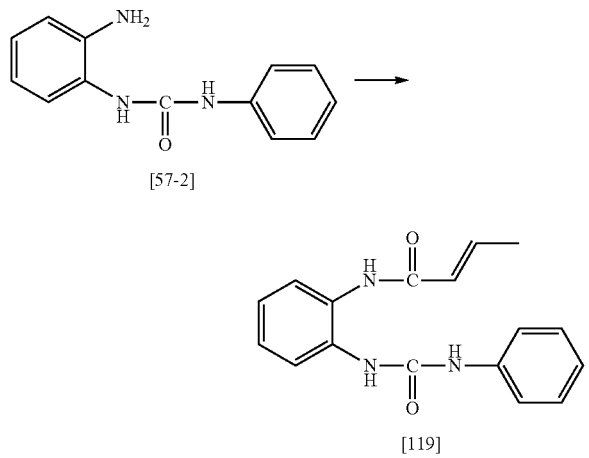 [SMILES: Nc1ccccc1NC(=O)Nc1ccccc1 ; C=CC(=O)Nc1ccccc1NC(=O)Nc1ccccc1]

To 133 parts of methylene chloride, 6.0 parts of the compound of the formula [57-2] were added, and the mixture was stirred. Subsequently, 2.9 parts of crotonoyl chloride (manufactured by Tokyo Chemical Industry Co., Ltd.) were added dropwise thereto at room temperature, then 2.8 parts of triethylamine (manufactured by Tokyo Chemical Industry Co., Ltd.) were added dropwise thereto at the same temperature as above, and the mixture was stirred for 1 hour. After the completion of the reaction, deposits were filtered off, and n-hexane was added to the filtrate. The resulting yellow oil substance was isolated, and ethyl acetate was added thereto. The resulting white solid was filtered off, washed with water, and dried in vacuum to obtain compound 119 as a white solid (4.2 parts).

MS(ESI): [M−H]⁻: cal.: 294.1, found: 294.1.

[Example 28] Preparation of Thermosenstive Recording Material and Thermosenstive Recording Paper Compound 116 of Table 3 obtained in Example 25 was pulverized and dispersed for 1 hour according to the composition given below using Multi Beads Shocker (model: PV1001(S)) manufactured by Yasui Kikai Corp. to prepare liquid [A].

| Liquid [A]: | |
| --- | --- |
| Compound 116 of Table 3 | 15 parts |
| 25% aqueous PVA solution | 20 parts |
| Water | 65 parts |

A mixture having the composition given below was pulverized and dispersed into a median size of 1 µm or smaller using a sand grinder to prepare dispersion [B] of the color-forming compound.

| Liquid [B]: | |
| --- | --- |
| 3-Dibutylamino-6-methyl-7-anilinofluoran | 35 parts |
| 15% aqueous PVA solution | 40 parts |
| Water | 25 parts |

Subsequently, the liquids thus obtained and the agents given below were mixed according to the composition given below to prepare a thermosenstive recording material coating liquid, which was then applied at 5 g/m² in terms of a dry weight onto high-quality paper having a basis weight of 50 g/m² and dried to prepare a thermosenstive recording paper having the thermosenstive recording layer of the present invention.

| | |
| --- | --- |
| Liquid [A] | 40.0 parts |
| Liquid [B] | 8.6 parts |
| 67% aqueous calcium carbonate dispersion | 9.0 parts |
| 48% modified styrene-butadiene copolymer latex | 6.3 parts |
| Water | 36.1 parts |

(Formation of Protective Layer)

Next, a protective layer coating liquid having the composition given below was applied at 2 g/m² in terms of a dry weight onto the thermosenstive recording layer and dried to prepare a thermosenstive recording paper having the thermosenstive recording layer covered with the protective layer.

| | |
| --- | --- |
| 40% styrene/acrylic acid ester copolymer emulsion | 115 parts |
| 5% aqueous bentonite dispersion | 17 parts |
| 45% aqueous styrene-acryl copolymer emulsion | 44 parts |
| 39% aqueous zinc stearate dispersion | 103 parts |
| 67% aqueous calcium carbonate dispersion | 15 parts |

Example 29

A thermosenstive recording paper having the thermosenstive recording layer of the present invention was obtained in the same way as in Example 28 except that compound 128 of Table 3 was used instead of compound 116 of Table 3.

Example 30

A thermosenstive recording paper having the thermosenstive recording layer of the present invention was obtained in the same way as in Example 28 except that compound 119 of Table 3 was used instead of compound 116 of Table 3.

Comparative Example 3

A mixture having the composition given below was pulverized and dispersed into a median size of 1 µm or smaller using a sand grinder to prepare liquid [C]. A thermosenstive recording paper having a thermosenstive recording layer for comparison was obtained in the same way as in Example 28 except that: liquid [A] in the composition of the thermosenstive recording layer coating liquid described in Example 28 was changed to liquid [C]; and the composition in the preparation of the thermosenstive recording material was changed to 24.0 parts of liquid [C] and 52.1 parts of water.

| Liquid [C]: | |
|---|---|
| Bisphenol S | 25 parts |
| 25% aqueous PVA solution | 20 parts |
| Water | 55 parts |

[Alcohol Resistance Test]

The thermosenstive recording paper obtained in each of Examples 28, 29 and 30 and Comparative Example 3 was printed at a pulse width of 1.4 msec using a thermal printer (TH-M2/PP) manufactured by Okura Engineering Co., Ltd., and then dipped in a 20% aqueous ethanol solution at 25° C. for 2 hours. The Macbeth reflection density of a colored part in the sample was measured before and after the test using a colorimeter (trade name "SpectroEye") manufactured by GretagMacbeth. All of the color measurements were performed under conditions involving illuminant C as a light source, ANSI A as a density reference and a view angle of 2 degrees. The results are shown in Table 8 below. A higher residual rate of the colored part means better alcohol resistance. The residual rate of the colored part was determined according to the following expression (I):

Residual rate (%)=(Macbeth reflection density of the colored part in the sample after the test)/(Macbeth reflection density of the colored part in the sample before the test)×100   (I)

TABLE 8

| | Example 28 | Example 29 | Example 30 | Comparative Example 3 |
|---|---|---|---|---|
| Residual rate (%) | 61 | 86 | 65 | 54 |

As is evident from Table 8, the samples obtained in Examples 28, 29 and 30 using the compound of the present invention had a higher residual rate than that of the sample obtained in Comparative Example 3 using bisphenol S as a color developing compound as described in Patent Literature 2, demonstrating that the present invention is superior in the alcohol resistance of colored parts to conventional techniques.

[Heat Resistance of Background]

The thermosenstive recording paper obtained in each of Examples 28, 29 and 30 and Comparative Example 3 was kept at 90° C. for 1 hour using an air-blowing constant-temperature thermostat (trade name "DKN402") manufactured by Yamato Scientific Co., Ltd. The ISO whiteness of the background was measured before and after the test using a colorimeter (trade name "SpectroEye") manufactured by GretagMacbeth. All of the color measurements were performed under conditions involving illuminant C as a light source, ANSI A as a density reference and a view angle of 2 degrees. The results are shown in Table 9 below. A smaller amount of change in ISO whiteness between before and after the test means better heat resistance of the background.

TABLE 9

| Measurement of background part | Example 28 | Example 29 | Example 30 | Comparative Example 3 |
|---|---|---|---|---|
| Before test | 70.8 | 73.6 | 71.9 | 67.2 |
| After test | 65.9 | 69.2 | 67.8 | 52.6 |
| Amount of change | 4.9 | 4.4 | 4.1 | 14.6 |

As is evident from Table 9, the samples obtained in Examples 28, 29 and 30 using the compound of the present invention exhibited a small amount of change in ISO whiteness between before and after the heat resistance test. Therefore, their backgrounds exhibited very high stability against heat, as compared with the sample obtained in Comparative Example 3 using bisphenol S as described in Patent Literature 2.

The invention claimed is:

1. A thermosensitive recording material comprising a compound represented by any of the following formulas (1) to (3):

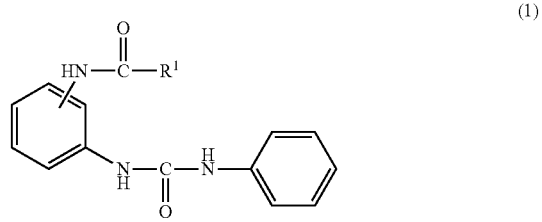

(1)

wherein $R^1$ represents an alkyl group optionally having a substituent;

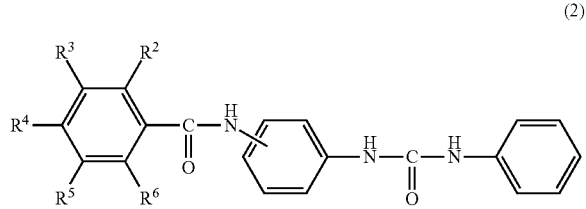

(2)

wherein $R^2$ to $R^6$ each independently represent a hydrogen atom, an alkyl group, an arylalkyl group, an aryl group, a 5- or 6-membered heterocyclic group containing 1 to 3 atoms selected from a nitrogen atom, an oxygen atom and a sulfur atom as ring-constituting atoms, a 5- or 6-membered heterocyclylamino group containing 1 to 3 atoms selected from a nitrogen atom, an oxygen atom and a sulfur atom as ring-constituting atoms, a ring-fused heterocyclylamino group in which one benzene ring is fused with a 5- or 6-membered heterocyclic group containing 1 to 3 atoms selected from a nitrogen atom, an oxygen atom and a sulfur atom as ring-constituting atoms, an alkoxy group, an aryloxy group, an alkylcarbonylamino group, an arylcarbonylamino group, an alkylcarbonyloxy group, an arylcarbonyloxy group, an alkylcarbonyl group, an arylcarbonyl group, a carbamoyl group, a monoalkylcarbamoyl group, a dialkylcarbamoyl group, a monoarylcarbamoyl group, a diarylcarbamoyl group, an alkoxycarbonyl group, an aryloxycarbonyl group, an alkylsulfonylamino group, an arylsulfonylamino group, a sulfamoyl group, a monoalkylsulfamoyl group, a dialkylsulfamoyl group, a monoarylsulfamoyl group, a diarylsulfamoyl group, a hydroxy group, an alkylsulfonyl group, an arylsulfonyl group, an alkylthio group, an arylthio group, an ureido group, a dialkylureido group, a monoarylureido group, a diarylureido group, an alkoxycarbonylamino group, a cyano group, a nitro group, an amino group, a monoalkylamino group, a dialkylamino group, an arylamino group which may be a monoarylamino group or a diarylamino group, a mercapto group, a carboxy group, a sulfone group or a halogen atom; and (3)

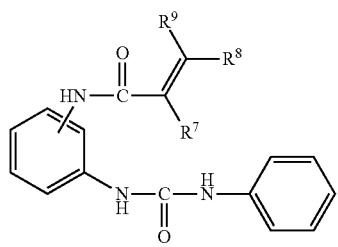

wherein $R^7$, $R^8$ and $R^9$ each represent a hydrogen atom, or an alkyl group or an aryl group optionally having a substituent.

2. The thermosensitive recording material according to claim 1, wherein in the formula (1), $R^1$ is an unsubstituted alkyl group or an alkyl group substituted with an aryl group.

3. The thermosensitive recording material according to claim 1, wherein in the formula (1), $R^1$ is an unsubstituted alkyl group.

4. The thermosensitive recording material according to claim 1, wherein in the formula (1), $R^1$ is a methyl group or an ethyl group.

5. The thermosensitive recording material according to claim 1, wherein the compound of the formula (1) is a compound represented by any of the following formulas (4) to (7):

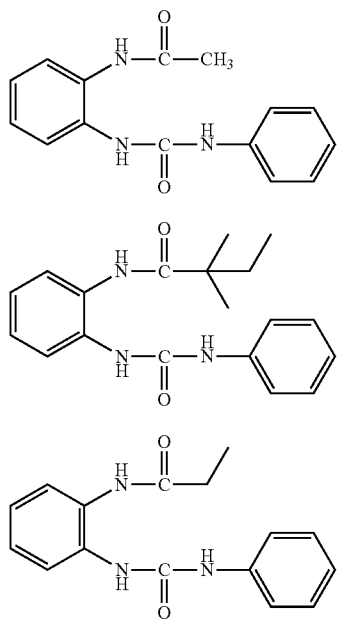

(4)

(5)

(6)

(7)

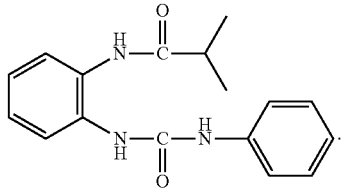

6. The thermosensitive recording material according to claim 1, wherein in the formula (2), $R^2$ to $R^6$ are each independently a group selected from the group consisting of a hydrogen atom, an alkyl group, an arylalkyl group, a 5- or 6-membered heterocyclylamino group containing 1 to 3 atoms selected from a nitrogen atom, an oxygen atom and a sulfur atom as ring-constituting atoms, a ring-fused heterocyclylamino group in which one benzene ring is fused with a 5- or 6-membered heterocyclic group containing 1 to 3 atoms selected from a nitrogen atom, an oxygen atom and a sulfur atom as ring-constituting atoms, an alkoxy group, an aryloxy group, an alkylcarbonylamino group, a carbamoyl group, a hydroxy group, a carboxy group, an alkylsulfonyl group, an arylthio group, a cyano group, an amino group, an arylamino group, a halogen atom and a nitro group.

7. The thermosensitive recording material according to claim 6, wherein in the formula (2), $R^2$ is a methyl group, and each of $R^3$ to $R^6$ is a hydrogen atom, or each of $R^2$, $R^3$, $R^5$ and $R^6$ is a hydrogen atom, and $R^4$ is a methyl group.

8. The thermosensitive recording material according to claim 1, wherein in the formula (2), $R^2$ to $R^6$ are each independently a hydrogen atom or an alkyl group.

9. The thermosensitive recording material according to claim 1, wherein in the formula (2), $R^2$ is a methyl group, and each of $R^3$ to $R^6$ is a hydrogen atom, or each of $R^2$, $R^3$, $R^5$ and $R^6$ is a hydrogen atom, and $R^4$ is a methyl group.

10. The thermosensitive recording material according to claim 1, wherein the compound of the formula (2) is a compound represented by any of the following formulas (8) to (11):

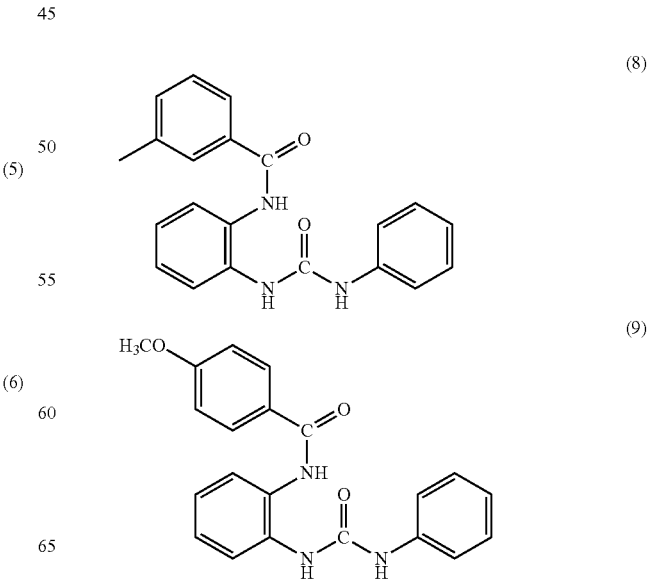

(8)

(9)

-continued

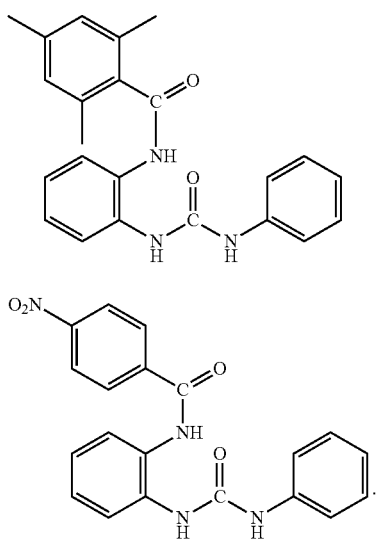

(10)

(11)

11. The thermosensitive recording material according to claim 1, wherein in the formula (3), each of $R^7$, $R^8$ and $R^9$ is a hydrogen atom, a methyl group or a phenyl group.

12. The thermosensitive recording material according to claim 11, wherein in the formula (3), all of $R^7$, $R^8$ and $R^9$ are hydrogen atoms; or $R^7$ is a methyl group, and each of $R^8$ and $R^9$ is a hydrogen atom; or $R^8$ is a methyl group or a phenyl group, and each of $R^7$ and $R^9$ is a hydrogen atom.

13. The thermosensitive recording material according to claim 1, wherein in the formula (3), all of $R^7$, $R^8$ and $R^9$ are hydrogen atoms; or $R^7$ is a methyl group, and each of $R^8$ and $R^9$ is a hydrogen atom; or $R^8$ is a methyl group or a phenyl group, and each of $R^7$ and $R^9$ is a hydrogen atom.

14. A compound represented by the following formula (3):

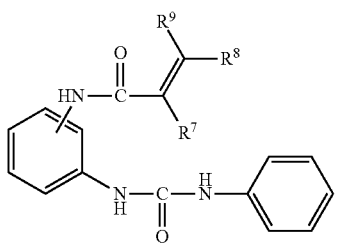

wherein $R^7$, $R^8$ and $R^9$ each represent a hydrogen atom, or an alkyl group or an aryl group optionally having a substituent, with the proviso that $R^7$, $R^8$ and $R^9$ are not each a hydrogen atom, and with the proviso that when $R^7$ and one of $R^8$ and $R^9$ are each a hydrogen atom, the other of $R^8$ and $R^9$ is not an aryl group substituted by an alkoxy group.

15. The compound according to claim 14, wherein the compound is represented by any of the following formulas (13) to (14):

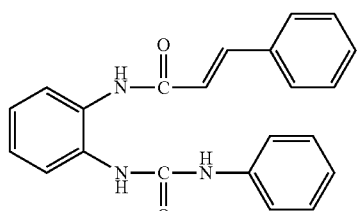

(13)

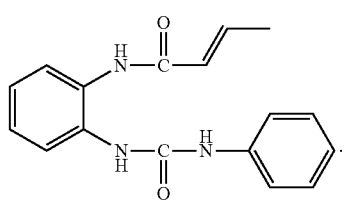

(14)

16. A compound represented by any of the following formulas (4) to (7):

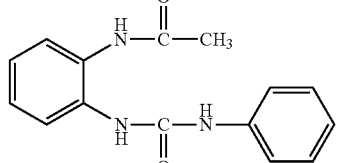

(4)

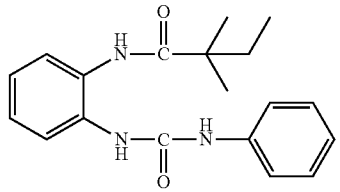

(5)

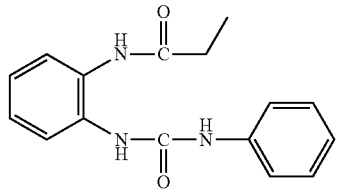

(6)

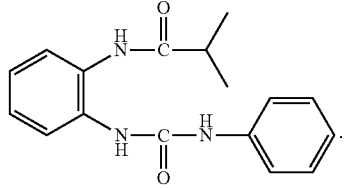

(7)

17. A compound represented by any of the following formulas (8) to (11):

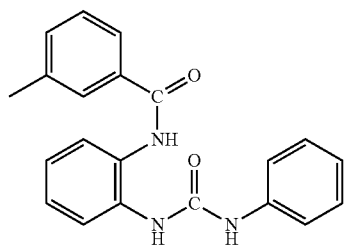

(8)

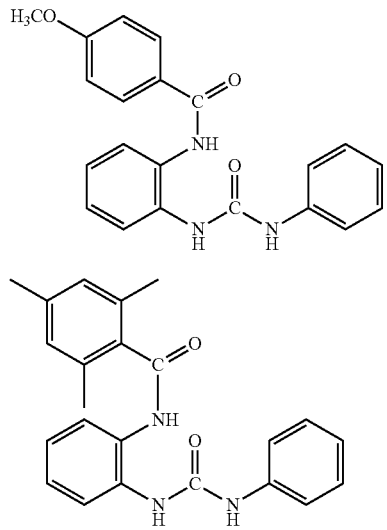
(9)
(10)
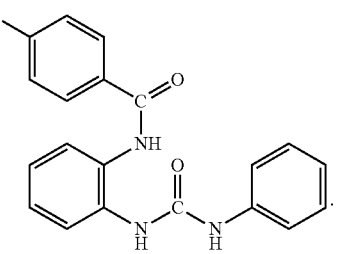
(11)
18. A thermosensitive recording layer comprising a thermosensitive recording material according to claim 1.
19. A thermosensitive recording paper comprising a thermosensitive recording layer according to claim 18.
* * * * *